United States Patent
Ji et al.

(10) Patent No.: US 7,241,773 B2
(45) Date of Patent: Jul. 10, 2007

(54) 3-QUINUCLIDINYL HETEROATOM BRIDGED BIARYL DERIVATIVES

(75) Inventors: Jianguo Ji, Libertyville, IL (US); Tao Li, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/015,157

(22) Filed: Dec. 17, 2004

(65) Prior Publication Data

US 2005/0137226 A1    Jun. 23, 2005

Related U.S. Application Data

(60) Provisional application No. 60/531,862, filed on Dec. 22, 2003.

(51) Int. Cl.
C07D 453/02 (2006.01)
A61K 31/439 (2006.01)

(52) U.S. Cl. ............. 514/305; 514/183; 514/299; 540/471; 546/133; 546/135

(58) Field of Classification Search ............ 546/133, 546/135; 540/471; 514/183, 299, 305
See application file for complete search history.

(56) References Cited

FOREIGN PATENT DOCUMENTS

| EP | 0 709 381 | 5/1996 |
|---|---|---|
| EP | 0 774 256 | 11/1996 |
| EP | 0773027 | 5/1997 |
| WO | 92/04333 | 3/1992 |
| WO | 94/18201 | 8/1994 |
| WO | 95/03302 | 2/1995 |
| WO | 96/12711 | 5/1996 |
| WO | 98/27983 | 7/1998 |
| WO | 2004/016608 | 2/2004 |
| WO | 2004/022556 | 3/2004 |

OTHER PUBLICATIONS

U.S. Appl. No. 10/744484, filed Dec. 2003, Tao.*
Conejo-Garcia, et al., "A prodrug system for hydroxylamines based on esterase catalysis", Bioorganic and Medicinal Chemistry Letters, 15 (2005), 4004-4009.*
Sriram, et., "Synthesis of stavudine amino acid ester prodrugs...", Bioorganic and Medicinal Chemistry Letters, 14, 2004, 1085-1087.*
Bader et al, Journal of Medicinal Chemistry, vol. 12, No. 5, pp. 1108-1109, 1969.*
Adler et al, "Schizophrenia, sensory gating, and nicotinic receptors," Schizophrenia Bulletin 24(2):189-202 (1998).
Cordero-Erausquin et al., "Tonic nicotinic modulation of serotoninergic transmission in the spinal cord," PNAS 98(5):2803-2807 (2001).
Friedman et al., "A double blind placebo controlled trial of donepezil adjunctive treatment to risperidone for the cognitive impairment of schizophrenia," Biol. Psychiatry 51:349-357 (2002).

Heeschen et al., "Nicotine stimulates angiogenesis and promotes tumor growth and athersclerosis," Nature Medicine 7(7):833-839 (2001).
Heeschen et al., "A novel angiogenic pathway mediated by non-neuronal nicotinic acetycholine receptors," Journal of Clinical Investigation 110(4):527-536 (2002).
Jonnala et al., "Relationship between the increased cell surface α7 nicotinic receptor expression and neuroprotection induced by several nicotinic receptor agonists," Journal of Neuroscience Research 66:565-572 (2001).
Kihara et al., "α7 Nicotinic receptor transduces signals to phosphatidylinositol 3- kinase to block A β-amyloid-induced neurotoxicity," Journal of Biological Chemistry 276(17):13541-13546 (2001).
Leonard et al., "Smoking and schizophrenia: abnormal nicotinic receptor expression," European Journal of Pharamcology 393:237-242 (2000).
Levin, "Nicotinic receptor subtypes and cognitive function," J. Neurobiol. 53:633-640 (2002).
Liu et al., "β-Amyloid peptide blocks the response of α7-containing nicotinic receptors on hippocampal neurons," PNAS 98(8):4734-4739 (2001).
Rowley et al., Current and novel approaches to the drug treatment of schizophrenia, Journal of Medicinal Chemistry 44(4):477-501 (2001).
Shimohama et al., "Nicotinic α7 receptors protect against glutamate neurotoxicity and neuronal ischemic damage," Brain Research 779:359-363 (1998).

(Continued)

*Primary Examiner*—Zinna N. Davis
(74) *Attorney, Agent, or Firm*—Portia Chen

(57) ABSTRACT

Compounds of formula:

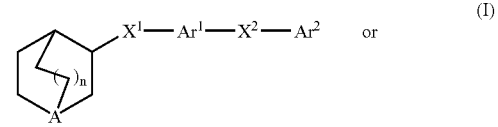

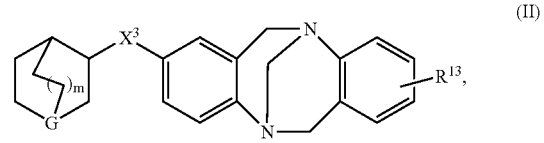

or pharmaceutically acceptable salts, esters, amides, or prodrugs thereof, wherein: A and G are each independently N or $N^+$—$O^-$; m and n are each independently 0, 1, or 2; $X^1$ and $X^3$ are each independently O, S, and —$N(R^1)$—; $X^2$ is O, S, —$N(R^1)$—, —$N(Ar^2)$—and —$N(R^2)C(O)$—; $Ar^1$ is a six-membered aromatic ring; $Ar^2$ is cyclohexyl or a mono- or bicyclic aromatic ring, and $R^{13}$ is hydrogen, alkyl, or halogen, as defined herein. The compounds are useful in treating conditions or disorders prevented by or ameliorated by nAChR ligands. Also disclosed are pharmaceutical compositions having compounds of formulas (I) and (II) and methods for using such compounds and compositions.

12 Claims, No Drawings

OTHER PUBLICATIONS

Son et al., "Evidence suggesting that the mouse sperm acrosome reaction initiated by the zona pellucida involves an α7 nicotinic acetylcholine receptor," Biology of Reproduction 68:1348-1353 (2003).

Stevens et al., "Selective $\alpha_7$-nicotinic agonists normalize inhibition of auditory response in DBA mice," Psychopharmacology 136:320-327 (1998).

Torii et al., "A versatile cycloaddition for the generation of pyrrolidine derivatives via C-N-C 1,3-dipoles," Chemistry Letters 747-748 (1996).

Wang et al., "Nicotinic acetylcholine receptor α7 subunit is an essential regulator of inflammation," Nature 421:384-388 (2003).

* cited by examiner

3-QUINUCLIDINYL HETEROATOM BRIDGED BIARYL DERIVATIVES

This application claims priority to U.S. Provisional Patent Application Ser. No. 60/531,862, filed Dec. 22, 2003, which is incorporated herein by reference.

TECHNICAL FIELD

The invention relates to 3-quinuclidinyl heteroatom bridged biaryl derivatives, compositions comprising such compounds, and methods of treating conditions and disorders using such compounds and compositions.

DESCRIPTION OF RELATED TECHNOLOGY

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to acetylcholine, norepinephrine, dopamine, serotonin, and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood, and emotion, among others.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, α2-α10 and β2-β4, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the α4β2 subtype), while another major population of receptors is comprised of the homomeric $(\alpha 7)_5$ (the α7 subtype).

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The α7 nAChRs have been shown to play a significant role in enhancing cognitive function, including aspects of learning, memory and attention (Levin, E. D., J. Neurobiol. 53: 633–640, 2002). For example, α7 nAChRs have been linked to conditions and disorders related to attention deficit disorder, attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities. The activity at the α7 nAChRs can be modified or regulated by the administration of α7 nAChR ligands. The ligands can exhibit antagonist, agonist, partial agonist, or inverse agonist properties. Thus, α7 ligands have potential in treatment of various cognitive disorders.

Although various classes of compounds demonstrating α7 nAChR-modulating activity exist, it would be beneficial to provide additional compounds demonstrating activity at the α7 nAChRs that can be incorporated into pharmaceutical compositions useful for therapeutic methods. Specifically, it would be beneficial to provide compounds that interact selectively with α7-containing neuronal nAChRs compared to other subtypes.

SUMMARY OF THE INVENTION

The invention is directed to 3-quinuclidinyl heteroatom bridged biaryl compounds as well as compositions comprising such compounds, and method of using the same. Compounds of the invention have the formula:

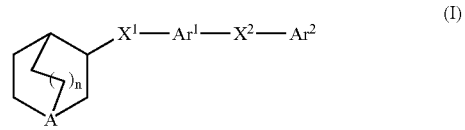

(I)

or a pharmaceutically acceptable salt, ester, amide, or prodrug thereof, wherein:

A is N or $N^+$—$O^-$;

n is 0, 1, or 2;

$X^1$ is selected from the group consisting of O, S, and —N($R^1$)—

—$X^2$ is selected from the group consisting of O, S, —N($R^1$)—, —N($Ar^2$)—, and —N($R^2$)C(O)—;

$Ar^1$ is a group of the formula:

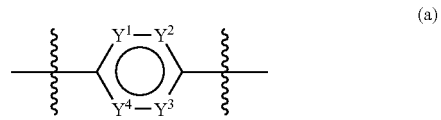

(a)

$Ar^2$ is cycloalkyl, or $Ar^2$ is a group of the formula:

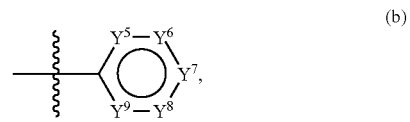

(b)

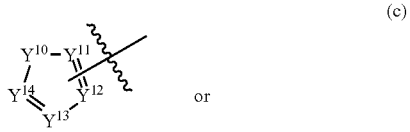

(c)

or

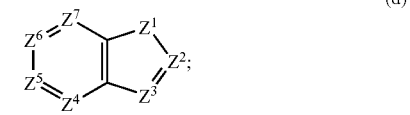

(d)

$Y^1$, $Y^2$, $Y^3$, and $Y^4$ are each independently selected from the group consisting of N and —C($R^3$);

$Y^5$, $Y^6$, $Y^7$, $Y^8$, and $Y^9$ are each independently selected from the group consisting of N and —C($R^6$);

$Y^{10}$ is selected from the group consisting of —N($R^9$), O and S;

$Y^{11}$ $Y^{12}$, $Y^{13}$, and $Y^{14}$ are each independently selected from the group consisting of N, C and —C($R^6$); provided that one of $Y^{11}$, $Y^{12}$, $Y^{13}$, and $Y^{14}$ is C and formula (c) is attached to $X^2$ or the nitrogen atom of —N(Ar$^2$)— through one of $Y^{11}$, $Y^{12}$, $Y^{13}$, and $Y^{14}$ that is represented by C;

$Z^1$ is independently selected from O, S, —N($R^9$), —C($R^{10}$) and —C($R^{10}$)($R^{10a}$);

$Z^2$ and $Z^3$ are each independently selected from the group consisting of N, C and —C($R^{12}$); provided that zero or one of $Z^2$ and $Z^3$ is C; and provided that when $Z^1$ is —C($R^{10}$), then $Z^2$ and $Z^3$ are other than C; and further provided that when one of $Z^2$ or $Z^3$ is C, then $Z^1$ is other than —C($R^{10}$);

$Z^4$, $Z^5$, $Z^6$ and $Z^7$ are independently selected from the group consisting of C and —C($R^{11}$); provided that zero or one of $Z^4$, $Z^5$, $Z^6$ and $Z^7$ is C; wherein when one of $Z^4$, $Z^5$, $Z^6$ and $Z^7$ is C, then formula (d) is attached to $X^2$ or the nitrogen atom of —N(Ar$^2$)— through one of $Z^4$, $Z^5$, $Z^6$ and $Z^7$ that is represented by C; $Z^1$ is other than —C($R^{10}$); and $Z^2$ and $Z^3$ are other than C; or when $Z^1$ is —C($R^{10}$), then formula (d) is attached to $X^2$ or the nitrogen atom of —N(Ar$^2$)— through the C atom of —C($R^{10}$),\; $Z^4$, $Z^5$, $Z^6$, and $Z^7$ are —C($R^{11}$); an are other than C; or when one of $Z^2$ or $Z^3$ is C, then formula (d) is attached to $X^2$ or the nitrogen atom of —N(Ar$^2$)— through $Z^2$ or $Z^3$ represented by C; $Z^1$ is other than —C($R^{10}$); and $Z^4$, $Z^5$, $Z^6$, and $Z^7$ are —C($R^{11}$);

$R^1$ and $R^2$ at each occurrence are each independently selected from the group consisting of hydrogen and alkyl;

$R^3$ at each occurrence is independently selected from the group consisting of hydrogen, halo, alkyl, aryl, —OR$^4$, and —NHR$^5$;

$R^4$ and $R^5$ are each independently selected from the group consisting of hydrogen, alkyl, alkylcarbonyl, arylcarbonyl, alkylsulfonyl, and arylsulfonyl;

$R^6$ at each occurrence is independently selected from the group consisting of hydrogen, halo, haloalkyl, alkyl, aryl, alkylcarbonyl, —OR$^7$, and —NHR$^8$;

$R^7$ and $R^8$ are each independently selected from the group consisting of hydrogen, alkyl, 1-aza-bicyclo[2.2.2]oct-3-yl, amino, alkylcarbonyl, arylcarbonyl, alkylsulfonyl, and arylsulfonyl; and $R^9$, $R^{10}$, $R^{10a}$, $R^{11}$, and $R^{12}$ at each occurrence are each independently selected from the group consisting of hydrogen, alkyl, aryl, alkylcarbonyl, and arylcarbonyl.

The invention also relates to compounds of formula:

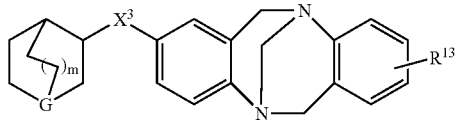

(II)

or pharmaceutically acceptable salts, esters, amides, and prodrugs thereof, wherein G is N or N$^+$—O$^-$; $X^3$ is —N($R^{14}$)—, O, or S; m is 0, 1, or 2; $R^{14}$ is hydrogen or alk $R^{13}$ is hydrogen, alkyl, or halogen.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity.

Yet another aspect of the invention relates to a method of selectively modulating to nAChR activity, for example α7 nAChR activity. The method is useful for treating and/or preventing conditions and disorders related to α7 nAChR activity modulation in mammals. More particularly, the method is useful for conditions and disorders related to attention deficit disorder, attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, among other systemic activities.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl" as used herein means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_AR_B$, ($NR_AR_B$)alkyl, ($NR_AR_B$)alkoxy, ($NR_AR_B$)carbonyl, and (N $R_AR_B$)sulfonyl.

The term "arylcarbonyl" as used herein means an aryl group, as defined herein, appended to the parent molecular moiety through a carbonyl group, as defined herein. Representative examples of alkylcarbonyl include, but are not limited to, (phenyl)carbonyl and (naphthyl)carbonyl.

The term "arylsulfonyl" as used herein means an aryl group, as defined herein, appended to the parent molecular moiety through a sulfonyl group, as defined herein. Representative examples of arylsulfonyl include, but are not limited to, phenylsulfonyl, (methylaminophenyl)sulfonyl, (dimethylaminophenyl)sulfonyl, and (naphthyl)sulfonyl.

The term "carbonyl" as used herein means a —C(O)— group.

The term "carboxy" as used herein means a —$CO_2H$ group.

The term "cyano" as used herein means a —CN group.

The term "formyl" as used herein means a —C(O)H group.

The term "halo" or "halogen" means —Cl, —Br, —I or —F.

The term "haloalkoxy" as used herein means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" as used herein means an aromatic five- or six-membered ring containing 1, 2, 3, or 4 heteroatoms independently selected from nitrogen, oxygen, or sulfur. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridinyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —$NR_AR_B$, ($NR_AR_B$)alkyl, ($NR_AR_B$)alkoxy, ($NR_AR_B$)carbonyl, and ($NR_AR_B$)sulfonyl.

The term "bicyclic heteroaryl" refers to fused aromatic nine- and ten-membered bicyclic rings containing 1, 2, 3, or 4 heteroatoms independently selected from nitrogen, oxygen, or sulfur, or a tautomer thereof. The bicyclic heteroaryl groups are connected to the parent molecular moiety through a carbon or nitrogen atom. Representative examples of bicyclic heteroaryl rings include, but are not limited to, indolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "hydroxy" as used herein means an —OH group.

The term "hydroxyalkyl" as used herein means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydrazine" as used herein means a —NH—NH$_2$ group.

The term "mercapto" as used herein means a —SH group.

The term "nitro" as used herein means a —NO$_2$ group.

The term "—NR$_A$R$_B$" as used herein means two groups, R$_A$ and R$_B$, which are appended to the parent molecular moiety through a nitrogen atom. R$_A$ and R$_B$ are each independently hydrogen, alkyl, alkylcarbonyl, or formyl. Representative examples of —NR$_A$R$_B$ include, but are not limited to, amino, methylamino, acetylamino, and acetylmethylamino.

The term "(NR$_A$R$_B$)alkyl" as used herein means a —NR$_A$R$_B$ group, as defined herein, appended to the parent molecular moiety through an alkyl group, as defined herein. Representative examples of (NR$_A$R$_B$)alkyl include, but are not limited to, (amino)methyl, (dimethylamino)methyl, and (ethylamino)methyl.

The term "(NR$_A$R$_B$)alkoxy" as used herein means a —NR$_A$R$_B$ group, as defined herein, appended to the parent molecular moiety through an alkoxy group, as defined herein. Representative examples of (NR$_A$R$_B$)alkoxy include, but are not limited to, (amino)methoxy, (dimethylamino)methoxy, and (diethylamino)ethoxy.

The term "(NR$_A$R$_B$)carbonyl" as used herein means a —NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "(NR$_A$R$_B$)sulfonyl" as used herein means a —NR$_A$R$_B$ group, as defined herein, appended to the parent molecular moiety through a sulfonyl group, as defined herein. Representative examples of (NR$_A$R$_B$)sulfonyl include, but are not limited to, aminosulfonyl, (methylamino)sulfonyl, (dimethylamino)sulfonyl, and (ethylmethylamino)sulfonyl.

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

Compounds of the Invention

Compounds of the invention can have the formula (I) as described above. More particularly, compounds of formula (I) can include, but are not limited to, compounds wherein Ar$^1$ is a group of the formula:

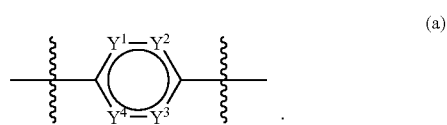

(a)

In a group of formula (a), Y$^1$, Y$^2$, Y$^3$, and Y$^4$ are each independently selected from the group consisting of N and —C(R$^3$), wherein R$^3$ at each occurrence is independently selected from the group consisting of hydrogen, halo, alkyl, aryl, —OR$^4$ and —NHR$^5$. Preferably, at least one of Y$^1$, Y$^2$, Y$^3$, and Y$^4$ is —C(R$^3$), such that group of formula (a) contains 0, 1, 2, or 3 nitrogen atoms.

Specific examples of groups for Ar$^1$ are, for example,

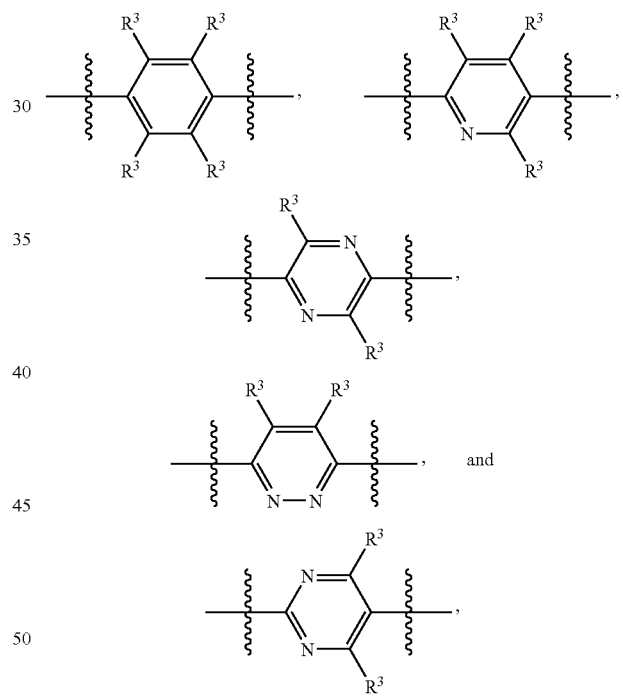

wherein R$^3$ is as previously defined for compounds of formula (I).

Compounds of the invention can include those wherein Ar$^2$ is cycloalkyl, preferably cyclohexyl, or Ar$^2$ is a group of the formula:

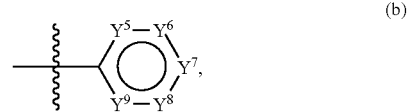

(b)

-continued

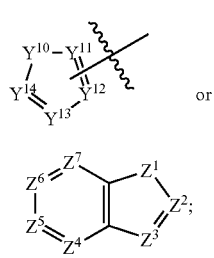
(c)

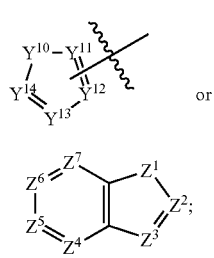 or (d)

wherein $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, $Y^{13}$, $Y^{14}$, $Z^1$, $Z^2$, $Z^3$, $Z^4$, $Z^5$, $Z^6$, and $Z^7$ are as previously described for compounds of formula (I).

Specific examples of groups for $Ar^2$ in a compound of formula (I) are, for example, cycloalkyl,

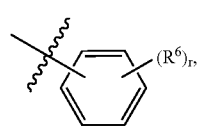
(3-i)

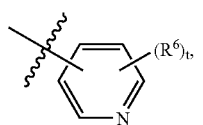
(3-ii)

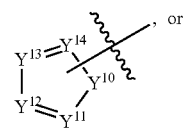
, or (3-iii)

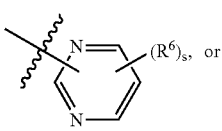
(3-iv)

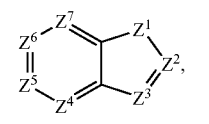
, or (3-v)

wherein:
r is 0, 1, 3, 4 or 5;
s is 0, 1, 2 or 3;
t is 0, 1, 2, 3 or 4;
$Y^{10}$ is selected from the group consisting of —N($R^9$), O and S;
one of $Y^{12}$ and $Y^{13}$ is N, C or —C($R^6$), and the other is C or —C($R^6$);
$Y^{11}$ and $Y^{14}$ are each independently selected from the group consisting of C and —C($R^6$); provided that one of $Y^{11}$ and $Y^{14}$ or one of $Y^{12}$ and $Y^{13}$ is C and formula (C) is attached to $X^2$ or the nitrogen atom of —N($Ar^2$)— through one of $Y^{11}$, $Y^{12}$, $Y^{13}$, and $Y^{14}$ that is represented by C; and
$Z^1$, $Z^2$, $Z^3$, $Z^4$, $Z^5$, $Z^6$, $Z^7$, $R^6$, and $R^9$ are as described for compounds of formula (I).

More specific examples of groups for $Ar^2$ in a compound of formula (I) are, for example, cycloalkyl, preferably cyclohexyl,

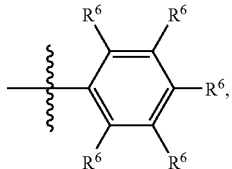
(4-i)

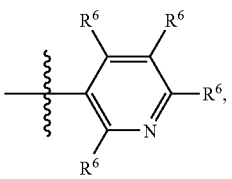
(4-ii)

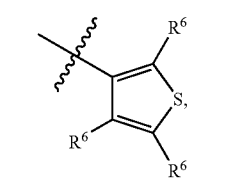
(4-iii)

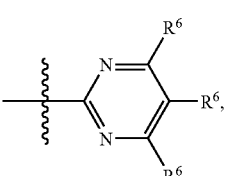
(4-iv)

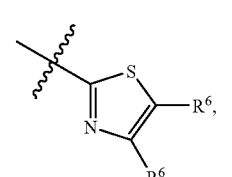
(4-v)

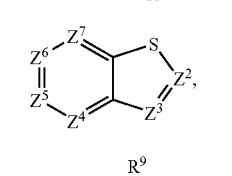
(4-vi)

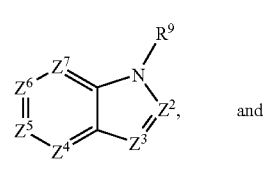
and

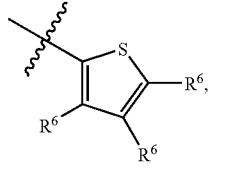
(4-viii)

wherein:
$Z^2$ and $Z^3$ are independently N, C or —C($R^{12}$); provided that zero or one of $Z^2$ and $Z^3$ is C;
$Z^4$, $Z^5$, $Z^6$, and $Z^7$ are independently selected from the group consisting of C and —C($R^{11}$); provided that zero or one of $Z^4$, $Z^5$, $Z^6$, and $Z^7$ is C; wherein
when one of $Z^4$, $Z^5$, $Z^6$, and $Z^7$ is C, then each of formulas (4-vi) and (4-vii) is attached to $X^2$ or the nitrogen atom of —N($Ar^2$)— through one of $Z^4$, $Z^5$, $Z^6$, and $Z^7$ that is represented by C, and $Z^2$ and $Z^3$ are each —C($R^{12}$); or when one of $Z^2$ or $Z^3$ is C, then each of formulas (4-vi) and (4-vii) is attached to $X^2$ or the nitrogen atom of —N($Ar^2$)— through $Z^2$ or $Z^3$ represented by C, and $Z^4$, $Z^5$, $Z^6$, and $Z^7$ are —C($R^{11}$);

$R^6$ is selected from the group consisting of hydrogen, fluoro, trifluoromethyl, hydroxy, 1-aza-bicyclo[2.2.2]oct-3-yloxy, 1-aza-bicyclo[2.2.2]oct-3-ylamino, isopropoxy, bromo, chloro, iodo, methyl, hydrazino, and amino;

$R^{12}$ is selected from the group consisting of hydrogen, methyl and phenyl; and $R^9$ and $R^{11}$ are as described for compounds of formula (I).

Specific embodiments of compounds of formula (I) contemplated as part of the invention include, but are not limited to:

3-(3-phenoxyphenoxy)quinuclidine;
3-(4-phenoxyphenoxy)quinuclidine;
(3R)-3-(4-phenoxyphenoxy)quinuclidine;
(3S)-3-(4-phenoxyphenoxy)quinuclidine;
3-{4-[4-(trifluoromethyl)phenoxy]phenoxy}quinuclidine;
3-[4-(4-fluorophenoxy)phenoxy]quinuclidine;
4-[4-(1-azabicyclo[2.2.2]oct-3-yloxy)phenoxy]phenol;
4-{4-[(3R)-1-azabicyclo[2.2.2]oct-3-yloxy]phenoxy}phenol;
4-{[4-(1-azabicyclo[2.2.2]oct-3-yloxy)phenyl]thio}phenol;
4-({4-[(3R)-1-azabicyclo[2.2.2]oct-3-yloxy]phenyl}thio)phenol;
3-{4-[(4-isopropoxyphenyl)thio]phenoxy}quinuclidine;
3-[4-(pyridin-3-yloxy)phenoxy]quinuclidine;
3-[4-(thien-3-yloxy)phenoxy]quinuclidine;
3-{4-[(5-bromopyrimidin-2-yl)oxy]phenoxy}quinuclidine;
N-[4-(1-azabicyclo[2.2.2]oct-3-yloxy)phenyl]-N-phenylamine;
N-{4-[(3R)-1-azabicyclo[2.2.2]oct-3-yloxy]phenyl}-N-phenylamine;
N-[4-(1-azabicyclo[2.2.2]oct-3-yloxy)phenyl]pyridin-3-amine;
N-[4-(1-azabicyclo[2.2.2]oct-3-yloxy)phenyl]benzamide;
N-[4-(1-azabicyclo[2.2.2]oct-3-yloxy)phenyl]-N-cyclohexylamine;
N-[4-(1-azabicyclo[2.2.2]oct-3-yloxy)phenyl]-N,N-dithien-3-ylamine;
N-[4-(1-azabicyclo[2.2.2]oct-3-yloxy)phenyl]-N-1,3-thiazol-2-yl-1,3-thiazol-2-amine
N-[4-(1-azabicyclo[2.2.2]oct-3-yloxy)phenyl]-N,N-bis(1-benzothien-3-yl)amine;
1-(5-{[4-(1-azabicyclo[2.2.2]oct-3-yloxy)phenyl]amino}thien-2-yl)ethanone;
N-[4-(1-azabicyclo[2.2.2]oct-3-yloxy)phenyl]-N-(4-methylthien-3-yl)amine;
3-[(6-phenoxypyridazin-3-yl)oxy]quinuclidine;
3-[(5-phenoxypyridin-2-yl)oxy]quinuclidine;
3-[(5-phenoxypyrimidin-2-yl)oxy]quinuclidine;
N-(4-phenoxyphenyl)quinuclidin-3-amine;
N-[4-(4-chlorophenoxy)phenyl]quinuclidin-3-amine;
N-[4-(4-methylphenoxy)phenyl]quinuclidin-3-amine;
N-[4-(4-aminophenoxy)phenyl]quinuclidin-3-amine;
N-1-azabicyclo[2.2.2]oct-3-yl-N'-phenylbenzene-1,4-diamine;
3-[(4-phenoxyphenyl)thio]quinuclidine;
N-[4-(1-azabicyclo[2.2.2]oct-3-ylthio)phenyl]-N-phenylamine;
4,4'-di(1-aza-bicyclo[2.2.2]oct-3-yloxy)-diphenyl ether;
4,4'-di[(3R)-1-aza-bicyclo[2.2.2]oct-3-yloxy]-diphenyl thioether;
4,4'-di(1-aza-bicyclo[2.2.2]oct-3-yl-amino)-diphenyl thioether;
3-[4-(4-iodo-phenoxy)-phenoxy]-1-aza-bicyclo[2.2.2]octane;
{4-[4-(1-aza-bicyclo[2.2.2]oct-3-yloxy)-phenoxy]-phenyl}-hydrazine;
3-[4-(2-methyl-3-phenyl-1H-indol-5-yloxy)-phenoxy]-1-aza-bicyclo[2.2.2]octane; and
3-[6-(4-iodo-phenoxy)-pyridazin-3-yloxy]-1-aza-bicyclo[2.2.2]octane;

or pharmaceutically acceptable salts, esters, amides, and prodrugs thereof.

The invention also relates to compounds of formula:

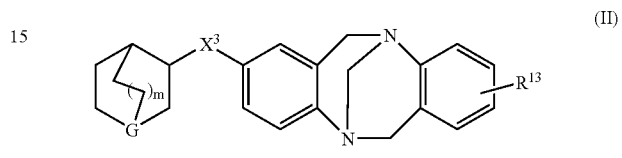

(II)

or pharmaceutically acceptable salts, esters, amides, and prodrugs thereof, wherein G is N or $N^+$—$O^-$; $X^3$ is —N($R^{14}$)—, O, or S; m is 0, 1, or 2; $R^{14}$ is hydrogen or alk $R^{13}$ is hydrogen, alkyl, or halogen. Preferably, $R^{13}$ is iodo or hydrogen.

Specific embodiments of compounds of formula (II) contemplated as part of the invention include, but are not limited to:

2-(1-aza-bicyclo[2.2.2]oct-3-yloxy)-8-iodo-6H, 1 2H-5,11-methano-dibenzo[b,f][
2-(1-aza-bicyclo[2.2.2]oct-3-yloxy)-6H, 12H-5,11-methano-dibenzo[b,f][1,5]diazo or pharmaceutically acceptable salts, esters, amides, and prodrugs thereof.

Compound names are assigned by using AutoNom naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13–30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

As used in the descriptions of the schemes and the examples, certain abbreviations are intended to have the following meanings: Ac for acetyl; Bu for butyl; dba for dibenzylidene acetone; DEAD for diethyl azodicarboxylate; DMSO for dimethylsulfoxide; EtOAc for ethyl acetate; EtOH for ethanol; Et₃N for triethylamine; Et₂O for diethyl ether; HPLC for high pressure liquid chromatography; $^i$Pr for isopropyl; Me for methyl; MeOH for methanol; NBS for N-bromosuccinimide; OAc for acetoxy; o-tol. for o-toluene; Ph for phenyl; tBu for tert-butyl; THF for tetrahydrofuran; NMP for 1-methyl-pyrrolidin-2-one; and TMHD for 2,2,6,6-tetramethylheptane-3,5-dione.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoracetyl. More particularly, the Boc protecting group may be removed by treatment with an acid such as trifluoroacetic acid or hydrochloric acid. The Cbz and Bn protecting groups may be removed by catalytic hydrogenation. The acetyl and trifluoracetyl protecting groups may be removed by a hydroxide ion.

The methods described below can entail use of various enantiomers. Where the stereochemistry is shown in the Schemes, it is intended for illustrative purposes only.

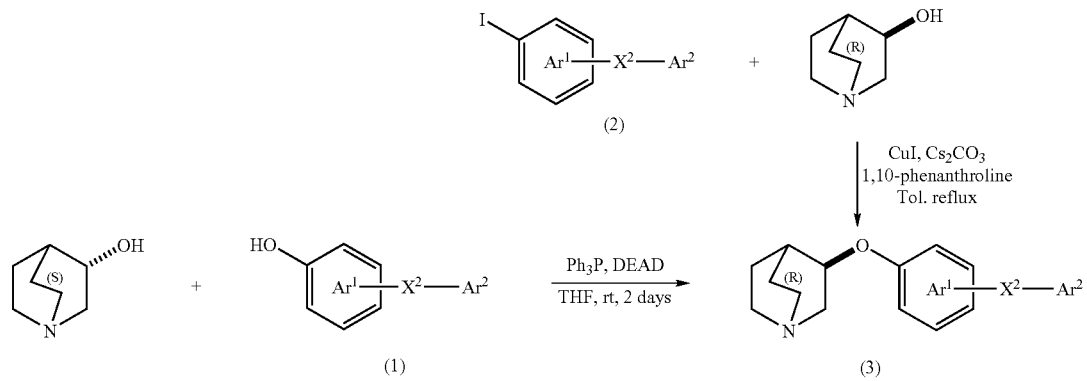

Quinuclidine ethers of formula (3), wherein Ar¹, X², and Ar² are as defined for formula (I), can be obtained by the methods described in Scheme 1. Compounds of formula (1) can be treated with 3-quinuclidinol in the presence of a phosphine, for example triphenylphosphine, and diethyl azodicarboxylate to provide compounds of formula (3). Alternatively, compounds of formula (2), wherein X² and Ar² are as defined for a compound of formula (I), can be reacted with CuI, Cs₂CO₃ and 1,10-phenanthroline as described in Org. Lett. 2002, 4, 973, to provide a desired compound of formula (3).

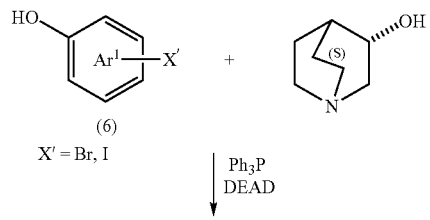

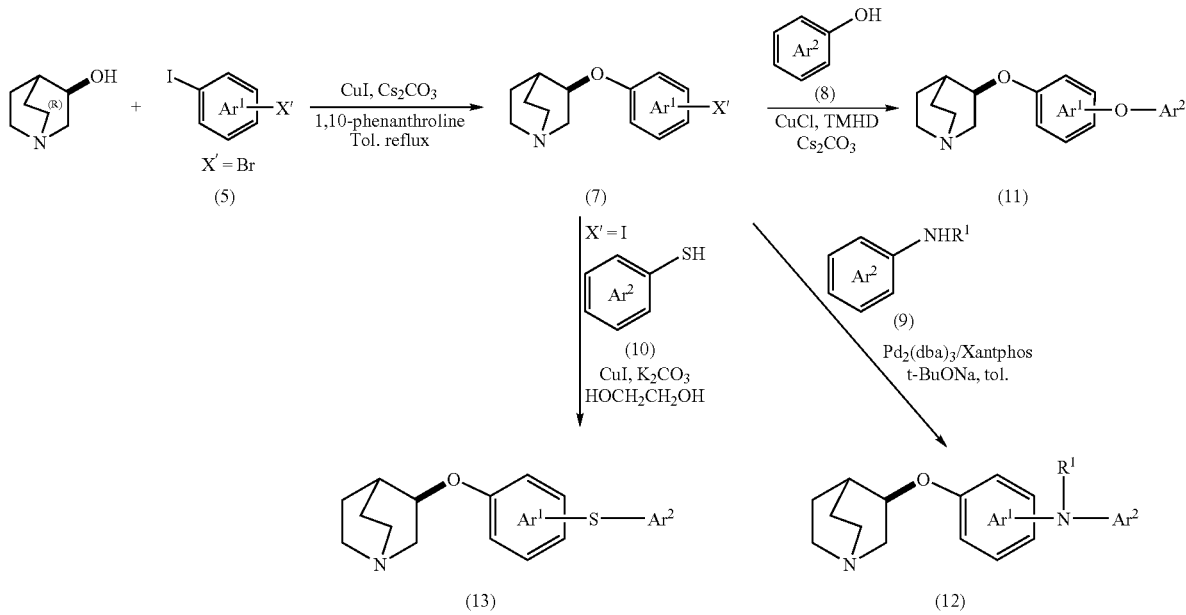

Quinuclidine ethers of general formula (11), (12), and (13), wherein Ar¹ and Ar² are as defined in formula (I), can be prepared as described in Scheme 2. 3-Quinuclidinol is treated with a halophenyl iodide of formula (5), wherein X' is bromide or iodide, with CuI, Cs₂CO₃ and 1,10-phenanthroline as described in Org. Lett., 2002, 4, 973, to obtain a halophenoxy quinuclidine of formula (7). Alternatively, a compound of formula (7) can be obtained by treating 3-quinuclidinol with a halo phenyl alcohol of formula (6), wherein X' is bromide or iodide, and diethyl azodicarboxylate in the presence of a phosphine, such as triphenylphosphine.

Compounds of formula (7), wherein X' are bromide or iodide, can be treated with the compound of formula (8) with CuCl, Cs₂CO₃ and TMHD in NMP to provide compounds of formula (11) as described in Org. Lett. 2002, 4, 1623. Compounds of formula (7), wherein X' are bromide or iodide, can be treated with an amine of a desired Ar² group of formula (9) with tris(dibenzylideneacetone)dipalladium (0) and Xantphos with sodium tert-butoxide in an organic solvent, such as toluene to provide compounds of formula (12) as described in Org. Lett. 2002, 4, 3481. Compounds of formula (7), wherein X' is iodide, can be treated with a thiol of a desired Ar² group of formula (10) with CuI, K₂CO₃ and 1,2-ethanediol to provide compounds of formula (13) as described in Org. Lett. 2002, 4, 3517.

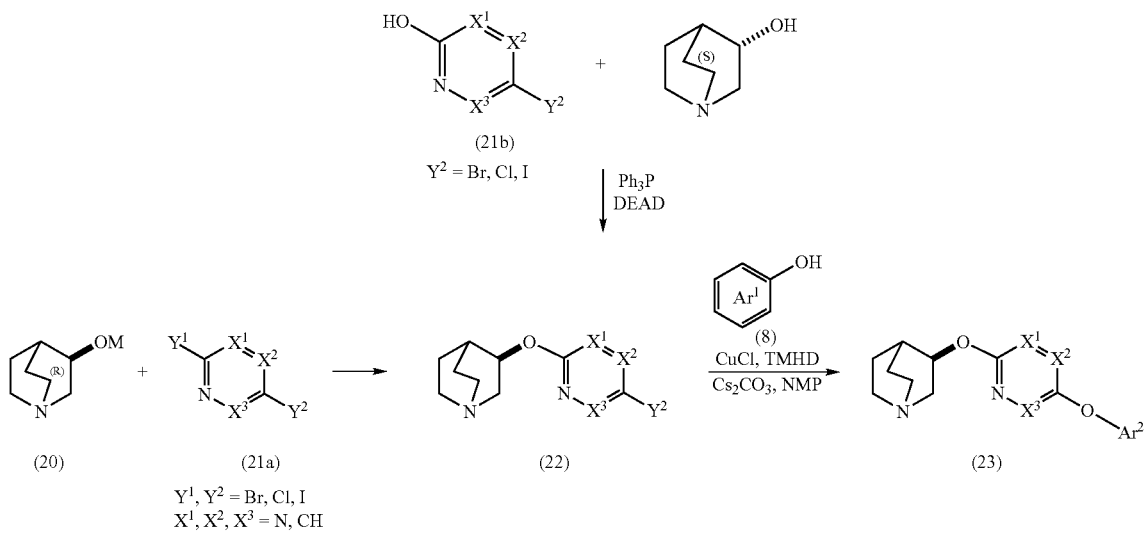

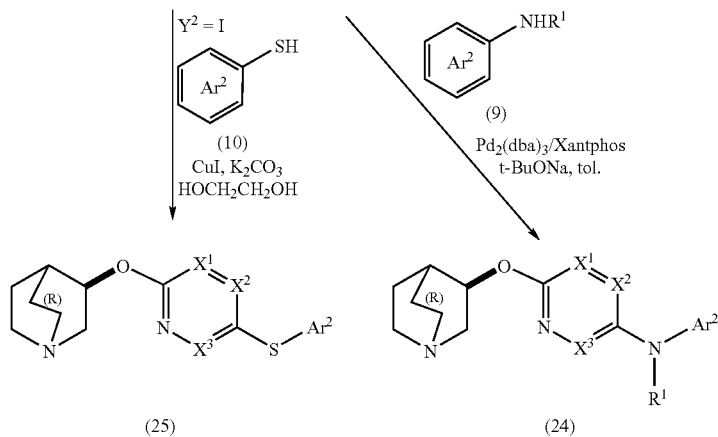

(25)    (24)

Quinuclidine ethers of formulas (23), (24), and (25), wherein Ar¹ is a nitrogen-containing heteroaryl, for example pyridazine, and Ar² is as defined for formula (I), can be prepared as shown in Scheme 3. A metal quinuclidinoxide of formula (20), wherein M is potassium or sodium, can be reacted with a dihaloaromatic ring, for example, dichloropyridazine, of formula (21a), wherein $Y^1$ and $Y^2$ are bromide, chloride, or iodide, and $X^1$, $X^2$, and $X^3$ are nitrogen or CH, to obtain a quinuclidine ether of formula (22). Alternatively, a compound of formula (22) can be obtained by treating 3-quinuclidinol with a compound of formula (21b), wherein $Y^2$ is bromide, chloride, or iodide, with diethyl azodicarboxylate in the presence of a phosphine, such as triphenylphosphine.

Compounds of formula (22), wherein $Y^2$ is bromide or iodide, can be treated with the compound of formula (8) with $Cs_2CO_3$, CuCl and TMHD in NMP to provide compounds of formula (23) as described in Org. Lett. 2002, 4, 1623. Compounds of formula (22), wherein $Y^2$ is bromide or iodide, can be treated with an amine of a desired Ar² group of formula (9) with tris(dibenzylideneacetone)dipalladium (0) and Xantphos with sodium tert-butoxide in an organic solvent, such as toluene to provide compounds of formula (24) as described in Org. Lett. 2002, 4, 3481. Compounds of formula (22), wherein $Y^2$ is iodide, can be treated with a thiol of a desired Ar² group of formula (10) with CuI, $K_2CO_3$ and 1,2-ethanediol to provide compounds of formula (25) as described in Org. Lett. 2002, 4, 3517.

Scheme 4

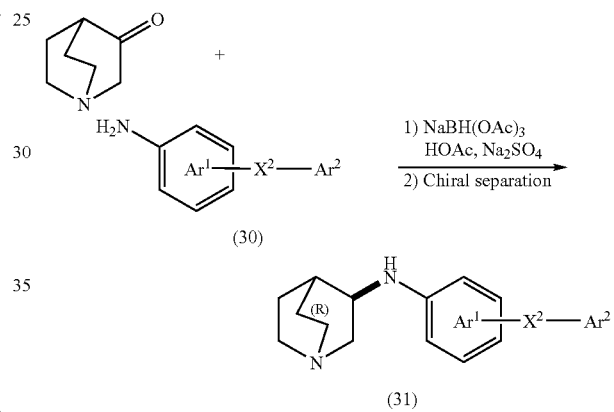

Compounds of formula (31), wherein Ar¹, $X^2$, and Ar² are as defined in compounds of formula (I), can be prepared as shown in Scheme 4. 3-Quinuclidinone and an amine of formula (30), can be treated with sodium triacetoxy borohydride and $Na_2SO_4$ in acetic acid to provide a racemic compound of formula (31) as described in Tetrahedron Lett. 1996, 37, 6045. The racemate of formula (31) can be resolved into its respective isomers by resolution with D-tartaric acid or via chiral HPLC chromatography on a Chiracel®-OD chromatography column using methods well-known in the art to provide the (R)- and (S)-isomers of formulas (31), respectively.

Scheme 5

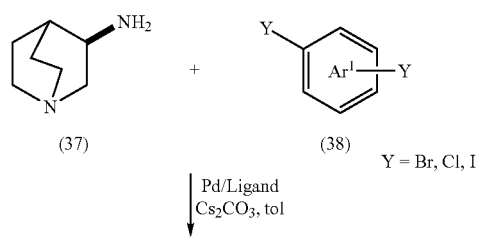

(37)    (38)    Y = Br, Cl, I

Pd/Ligand
$Cs_2CO_3$, tol

-continued

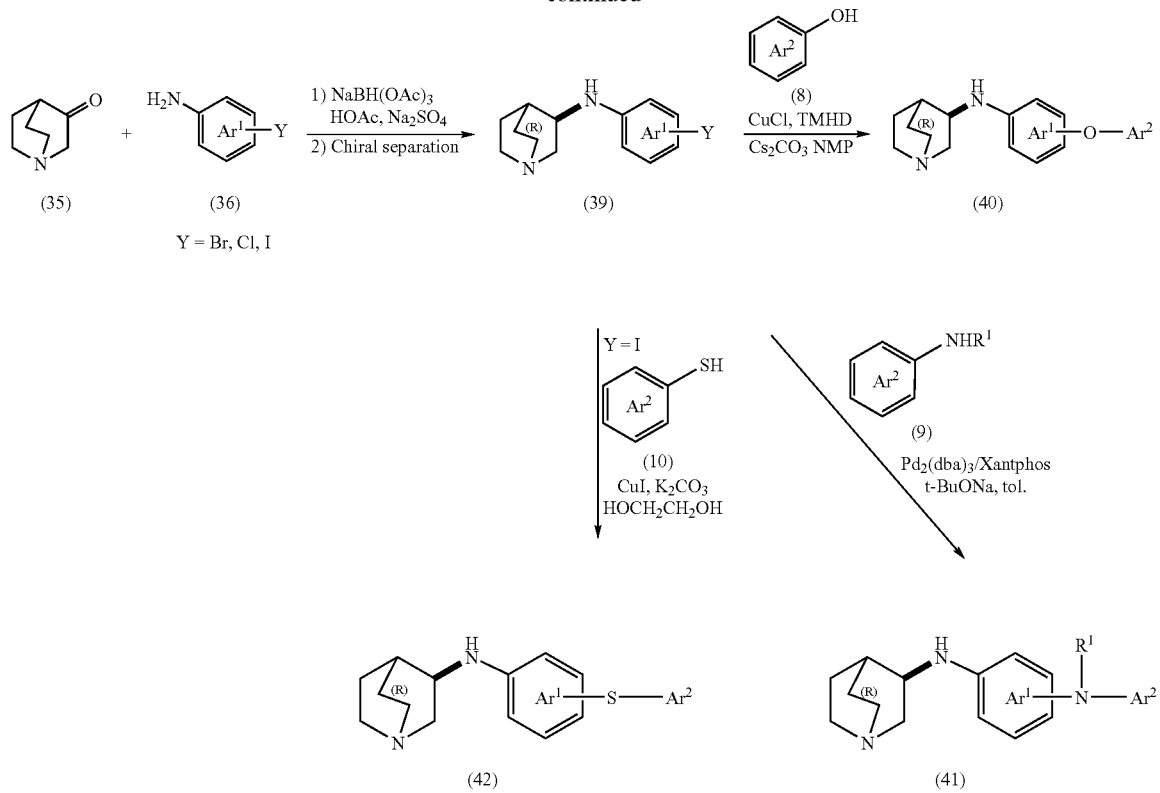

Quinuclidine amine derivatives of formulas (40), (41), and (42), wherein $Ar^1$, $Ar^2$, and $R^1$ are as defined for formula (I), can be prepared as shown in Scheme 5. 3-Quinuclidinone (35) and a haloarylamine of formula (36), wherein Y is bromide, chloride, or iodide, can be treated with sodium triacetoxy borohydride and $Na_2SO_4$ in acetic acid to provide a racemic compound of formula (39) as described in Tetrahedron Lett. 1996, 37, 6045. The racemate of formula (39) can be resolved into its respective isomers by resolution with D-tartaric acid or via chiral HPLC chromatography on a Chiracel®-OD chromatography column using methods well-known in the art to provide the (R)- and (S)-isomers of formula (39), respectively. Alternatively, a compound of formula (39) can be obtained by treating 3-aminoquinuclidine (37) with haloaromatic group as described in formula (38) in $Cs_2CO_3$ in the presence of palladium catalyst, preferably in toluene.

Compounds of formula (39), wherein Y is bromide or iodide, can be treated with a compound of formula (8) with CuCl, TMHD and $Cs_2CO_3$ in NMP to provide compounds of formula (40) as described in Org. Lett. 2002, 4, 1623. Compounds of formula (39), wherein Y is bromide or iodide, can be treated with an amine of a desired $Ar^2$ group of formula (9) with tris(dibenzylideneacetone)dipalladium (0) and Xantphos with sodium tert-butoxide in an organic solvent, such as toluene, to provide compounds of formula (41) as described in Org. Lett. 2002, 4, 3481. Compounds of formula (39), wherein X' is iodide, can be treated with a thiol of a desired $Ar^2$ group of formula (10) with CuI, $K_2CO_3$ and 1,2-ethanediol to provide compounds of formula (42) as described in Org. Lett. 2002, 4, 3517.

Scheme 6

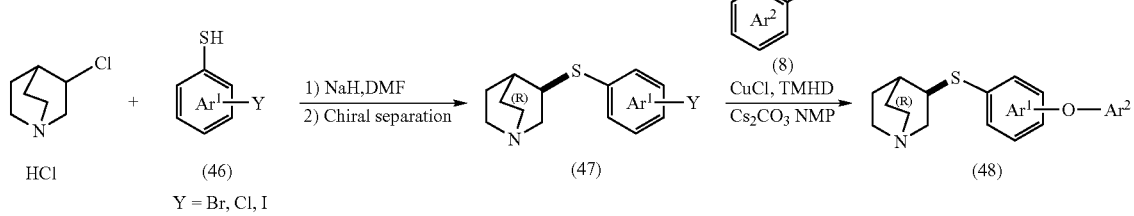

-continued

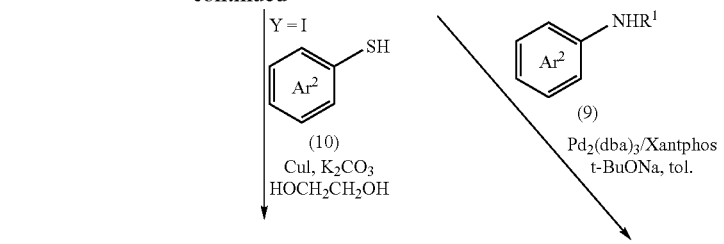

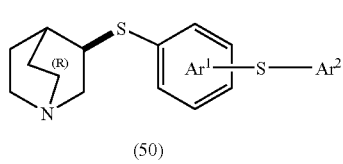
(50)

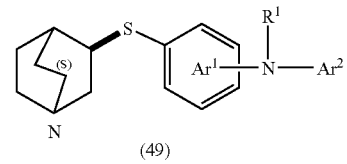
(49)

Quinuclidine sulfide derivatives of formulas (48), (49), and (50), wherein $Ar^1$, $Ar^2$, and $R^1$ are as defined for formula (I), can be prepared as shown in Scheme 6. 3-Chloroquinuclidine can be reacted with a haloarylthiol of formula (46), wherein Y is bromide, chloride, or iodide, to provide a racemic compound of formula (47) as described in J. Med. Chem. 1999, 42, 1306. The racemate of formula (47) can be resolved into its respective isomers by resolution with D-tartaric acid or via chiral HPLC chromatography on a Chiracel®-OD chromatography column using methods well-known in the art to provide the (R)- and (S)-isomers of formula (47), respectively.

Compounds of formula (47), wherein Y is bromide or iodide, can be treated with a compound of formula (8) with CuCl, TMHD and $Cs_2CO_3$ in NMP to provide compounds of formula (48) as described in Org. Lett. 2002, 4, 1623. Compounds of formula (47), wherein Y is bromide or iodide, can be treated with an amine of a desired $Ar^2$ group of formula (9) with tris(dibenzylideneacetone)dipalladium (0) and Xantphos with sodium tert-butoxide in an organic solvent, such as toluene to provide compounds of formula (49) as described in Org. Lett. 2002, 4, 3481. Compounds of formula (47), wherein Y is iodide, can be treated with a thiol of a desired $Ar^2$ group of formula (10) with CuI, $K_2CO_3$ and 1,2-ethanediol to provide compounds of formula (50) as described in Org. Lett. 2002, 4, 3517.

Scheme 7

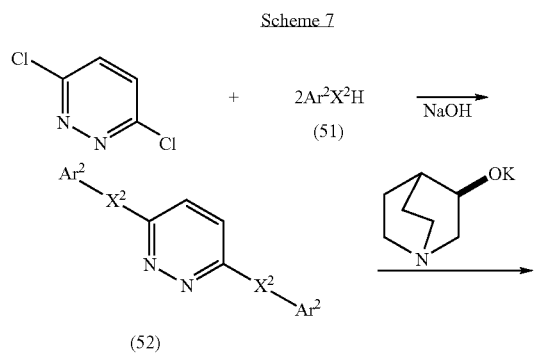

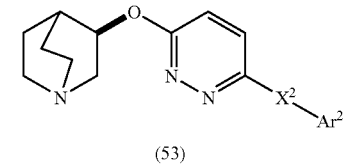
(53)

Compounds of formula (53), wherein $X^2$ and $Ar^2$ are as defined for compounds of formula (I), can be prepared as shown in Scheme 7. 3,6-Dichloropyridazine can be treated with a compound of formula (51) and sodium hydroxide to provide compounds of formula (52). Compounds of formula (52) are reacted with potassium quinuclidinoxide to provide compounds of formula (53).

Scheme 8

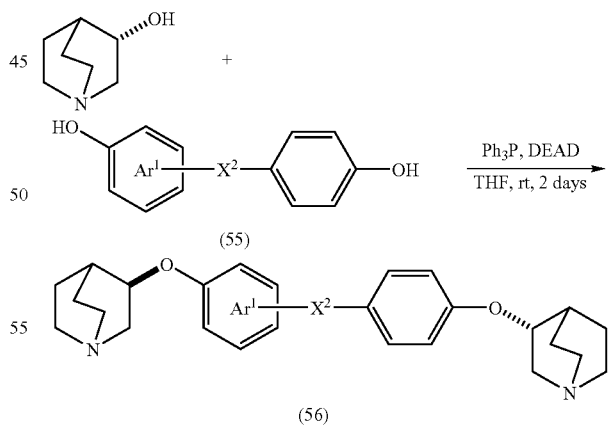

Quinuclidine ethers of general formula (56), wherein $Ar^1$ and $X^2$ are as defined in formula (I), can be prepared as described in Scheme 8. Commercially available compounds of formula (55) can be converted to compounds of formula (56) using the conditions employed in the transformation of compounds of formula (21b) to compounds of formula (22) as described in Scheme 3.

Scheme 9
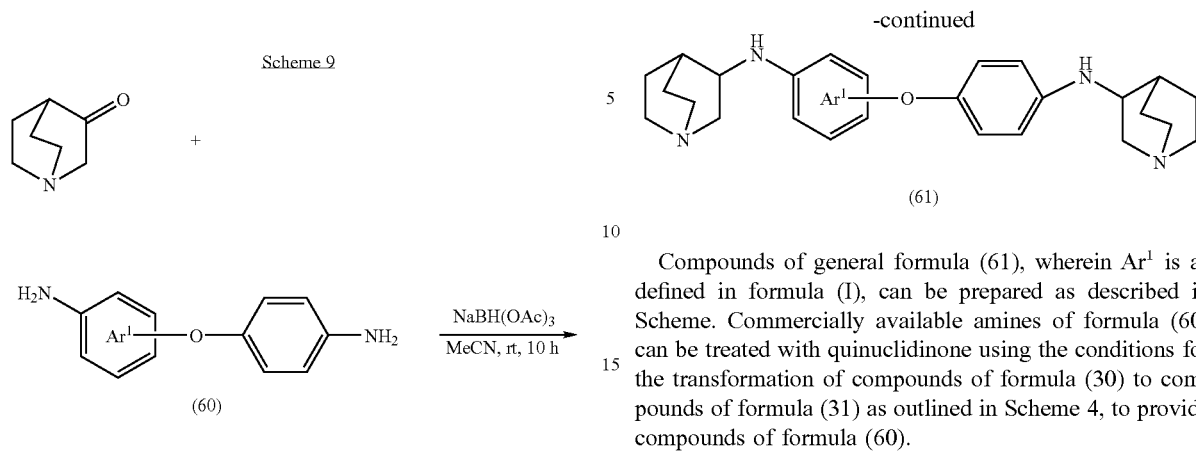
Compounds of general formula (61), wherein Ar¹ is as defined in formula (I), can be prepared as described in Scheme. Commercially available amines of formula (60) can be treated with quinuclidinone using the conditions for the transformation of compounds of formula (30) to compounds of formula (31) as outlined in Scheme 4, to provide compounds of formula (60).
Scheme 10
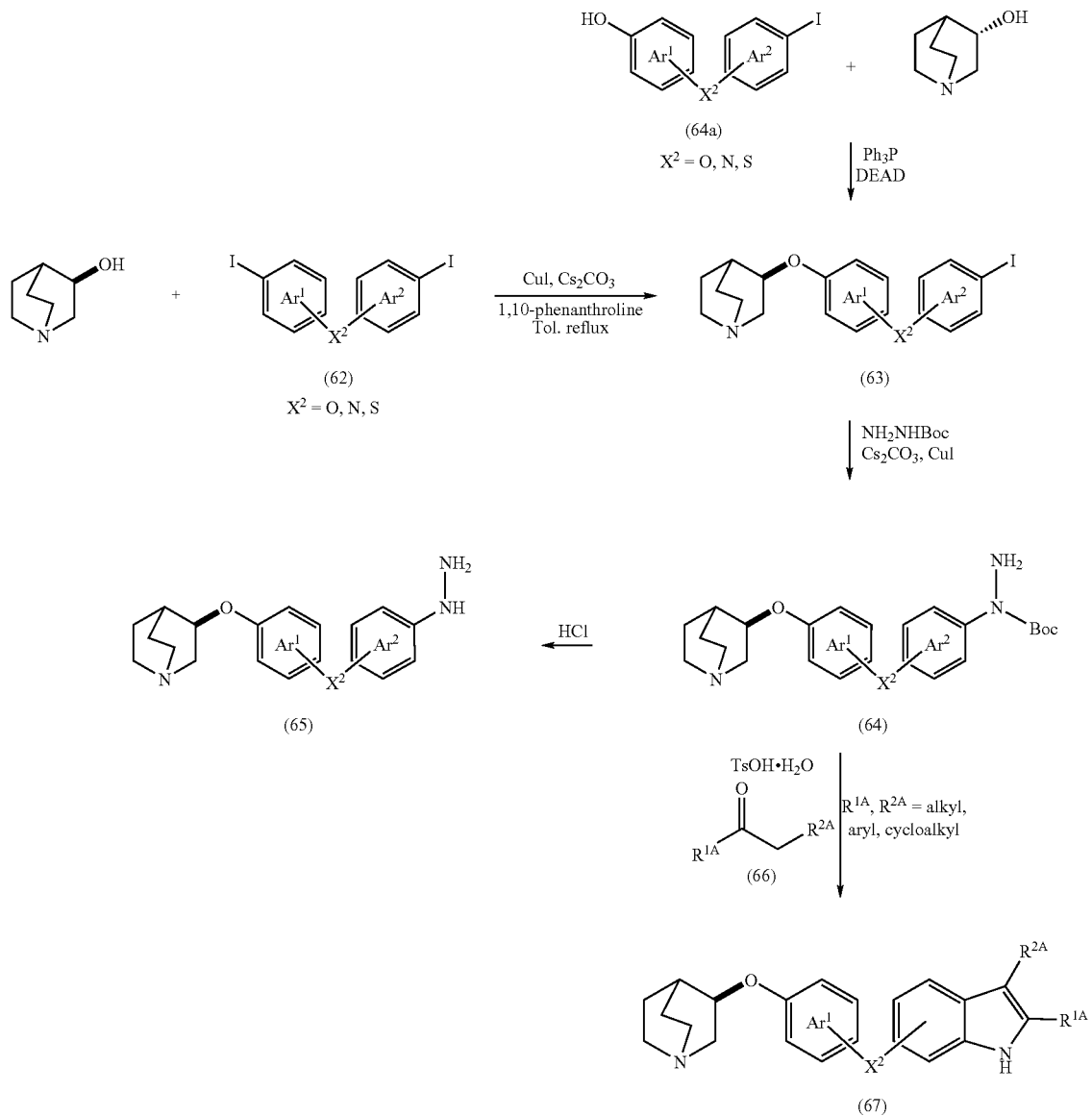

Compounds of general formulas (65) and (67) wherein Ar¹, X², Ar² are as defined in formula (I) can be obtained from compounds of formula (64) or (62) as described in Scheme 10. Compounds of formula (62) can be reacted with 3-quinuclidinol using the conditions for the transformation of compounds of formula (2) to compounds of formula (3) as described in Scheme 1, to provide compounds of formula (63). Alternatively, compounds of formula (63) can be obtained from compounds of formula (64a), using the conditions employed for the conversion of compounds of formula (1) to compounds of formula (3) as described in Scheme 1. Reacting compounds of formula (63) with a N-protected hydrazine such as hydrazinecarboxylic acid tert-butyl ester in the presence of a base such as cesium carbonate, and copper(I) iodide, provides compounds of formula (64). Deprotecting compounds of formula (64) in acidic medium such as aqueous hydrochloric acid or trifluoroacetic acid, provides compounds of formula (65). Compounds of formula (64) can be reacted with ketones of formula (66) in the presence of an acid such as toluene sulfonic acid or hydrochloric acid, followed by in situ cyclization to afford compounds of formula (67).

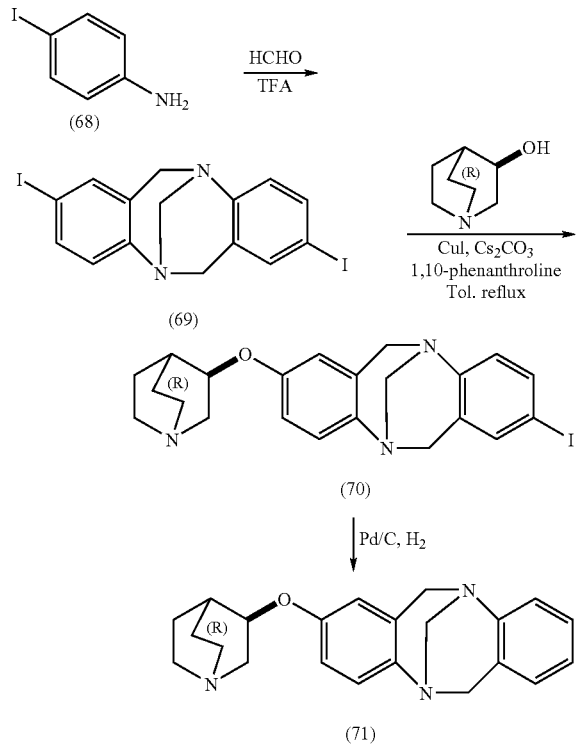

Scheme 11

Compounds of formula (71) can be obtained from compounds of formula (68) as described in Scheme 11. Reacting compounds of formula (68) with formaldehyde in the presence of trifluoroacetic acid provides compounds of formula (69). The di-iodo compounds of formula (69) can be reacted with 3-quinuclidinol using the reaction conditions used for the conversion of compounds of formula (2) to compounds of formula (3) as described in Scheme 1, to provide compounds of formula (70). De-iodonation of compounds of formula (70) with hydrogen, in the presence of palladium/carbon provides compounds of formula (71).

Compounds of formula (I) wherein A is N can be converted to compounds of formula (I) wherein A is N⁺—O⁻ by treatment with an oxidizing agent. Compounds of formula (II) wherein G is N can be converted to compounds of formula (II) wherein G is N⁺—O⁻ using the same conditions. Examples of the oxidizing agent include, but not limited to, aqueous hydrogen peroxide and m-chloroperbenzoic acid. The reaction is generally performed in a solvent such as, but not limited to, acetonitrile, water, dichloromethane, acetone or mixture thereof, preferably a mixture of acetonitrile and water, at a temperature from about room temperature to about 80° C., for a period of about 1 hour to about 4 days.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) or (II) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

Methods of the Invention

Compounds and compositions of the invention are useful for modulating the effects of nAChRs, and more particularly α7 nAChRs. In particular, the compounds and compositions of the invention can be used for treating and preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

The compounds of the invention, including but not limited to those specified in the examples, possess an affinity for nAChRs, and more particularly α7 nAChRs. As α7 nAChRs ligands, the compounds of the invention can be useful for the treatment and prevention of a number of α7 nAChR-mediated diseases or conditions.

For example, α7 nAChRs have been shown to play a significant role in enhancing cognitive function, including aspects of learning, memory and attention (Levin, E. D., J. Neurobiol. 53: 633–640, 2002). As such, α7 ligands are suitable for the treatment of cognitive disorders including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B. and Buccafusco, J. J., J. Neurosci. Res. 66: 565–572, 2001) and in vivo (Shimohama, S. et al., Brain Res. 779: 359–363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734–4739, 2001). The activation of α7 nAChRs has been shown to block this neurotoxicity (Kihara, T. et al., J. Biol. Chem. 276: 13541–13546, 2001). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 393: 237–242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189–202, 1998; Stevens, K. E. et al., Psychopharmacology 136: 320–327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833–839, 2001). Improved angiogenesis has been shown to involve activation of the α7 nAChR (Heeschen, C. et al, J. Clin. Invest. 110: 527–536, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero- Erausquin, M. and Changeux, J.-P. PNAS 98:2803–2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384–388, 2003). Therefore, selective α7 ligands demonstrate potential for treating conditions involving inflammation and pain.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348–1353 2003). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477–501, 2001). Such cognitive deficit has been linked to dysfunction of the nicotinic cholinergic system, in particular with decreased activity at α7 receptors. (Friedman, J. I. et al., Biol Psychiatry, 51: 349–357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 mg/kg body weight to about 1 g/kg body weight. More preferable doses can be in the range of from about 0.10 mg/kg body weight to about 100 mg/kg body weight. If desired, the effective daily dose can be divided into multiple doses for purposes of administration. Consequently, single dose compositions may contain such amounts or submultiples thereof to make up the daily dose.

The compounds and processes of the invention will be better understood by reference to the following examples and reference examples, which are intended as an illustration of and not a limitation upon the scope of the invention.

REFERENCE EXAMPLES

Reference Example 1

(R)-3-quinuclidinol (R)-3-Quinuclidinol hydrochloride (Aldrich, 20 g, 12.2 mmol) was treated with NaOH aqueous solution(20%, 50 mL) at ambient temperature for 10 min. It was then extracted with $CHCl_3$/PrOH (v. 10:1, 3×200 mL). The extracts were combine, washed with brine (50 mL) and dried over $MgSO_4$. The drying agents were removed by filtration and the filtrates was concentrated under reduced pressure to give the title compound as white solid (15.5 g, yield, 99%). $^1$H NMR (300 MHz, MeOH-$d_4$) δ 1.36–1.50 (m, 1H), 1.52–1.60 (m, 1H), 1.76–1.85 (m, 2H), 1.90–2.05 (m, 1H), 2.50–2.95(m, 5H), 3.10 (ddd, J=14.2, 8.4, 2.3 Hz, 1H), 3.82–3.88 (m, 1H) ppm. MS (DCl/$NH_3$): m/z 128 $(M+H)^+$.

Reference Example 2

(S)-3-quinuclidinol

Reference Example 2A (R)-1-Azabicyclo[2.2.2]oct-3-yl Benzoate (L) Tartrate

1-Azabicyclo[2.2.2]oct-3-yl benzoate (Sigma, 17.9 g, 77.5 mmol) was treated with (L)-tartaric acid (Aldrich, 99% ee, 11.63 g, 77.5 mmol) in ethanol (80%, 222 mL) at ambient temperature for 1 week. The white solid was filtered off and dried under reduced pressure to provide 6.5 g of the title compound with ~80% enantiomeric excess. Recrystallization from ethanol provided an enantiomeric excess of >98%. HPLC: chiralpak AD column 25 cm×4 mm ID; ethanol:hexanes 15:85; flow rate 1 mL/minute; uv 220 nM; Retention time 13.3 minutes. MS (DCl/$NH_3$) m/z 232 $(M+H)^+$.

Reference Example 2B

(R)-quinuclidin-3-ol

The product of Reference Example 2A (4.5 g, 11.8 mmol) in MeOH (40 mL) was treated with 15% aqueous NaOH (40 mL) and heated at 50 °C. for 10 hours. The mixture was allowed to cool to room temperature, the MeOH was removed under reduced pressure, and the residue was extracted with chloroform (4×80 mL). The extracts were combined, dried over $MgSO_4$ (anhydrous), filtered, and the filtrate was concentrated to give the title product as a white solid (1.35 g, yield, 90%). MS ($DCl/NH_3$) m/z 128 (M+H)$^+$.

Reference Example 2C

(S)-1-azabicyclo[2.2.2]oct-3-yl Benzoate (D)-Tartrate

The mother liquors of Reference Example 2A were concentrated under reduced pressure, treated with aqueous NaOH (1 N, 50 mL) at room temperature, stirred for 30 minutes, and extracted with chloroform (3×100 mL). The extracts were combined, dried ($MgSO_4$), filtered, and the filtrate was concentrated under reduced pressure. The residue (15.25 g, 66 mmol) was treated with (D)-tartaric acid (Aldrich, 97% ee, 9.9 g, 66 mmol,) in ethanol (80%, 190 ml) at room temperature and stirred for 3 days. The mixture was filtered to provide the title product, 92.3% enantiomeric excess (7.0 g, 28% yield). (HPLC: chiralpak AD column 25 cm×4 mm ID; ethanol:hexanes 15:85; flow rate 1 mL/minute; uv 220 nm; Retention time 7.87 minutes).

Reference Example 2D

(S)-quinuclidin-3-ol

The product of Reference Example 2C (7.0 g, 18.4 mmol) was treated with NaOH (aqueous) according to the procedure of Example 1 B. The title product was obtained as a white solid (2.0 g, yield, 86%). MS ($DCl/NH_3$) m/z 128 (M+H)$^+$.

EXAMPLES

Example 1

3-(3-phenoxyphenoxy)quinuclidine hydrochloride

Example 1A

3-(3-phenoxyphenoxy)quinuclidine

3-Hydroxy quinuclidine (Aldrich, 254 mg, 2 mmol) in tetrahydrofuran (anhydrous, 10 mL) was treated with 3-phenoxyphenol (Aldrich, 186 mg, 1 mmol), DIAD (diisopropyl azadicarboxylate, Aldrich, 404 mg, 2 mmol), and triphenylphosphine (Aldrich, 522 mg, 2 mmol) at ambient temperature for two days. The reaction mixture was concentrated under reduced pressure. The residue was purified by chromatography ($SiO_2$, $CH_2Cl_2$:MeOH:$NH_3.H_2O$, 90:10:1, $R_f$ 0.30) as oil (250 mg, yield, 85%). $^1$H NMR (MeOH-$d_4$, 300 MHz) δ 1.42–1.58 (m, 1H), 1.64–1.75 (m, 1H), 1.78–1.88 (m, 1H), 2.00–2.15 (m, 1H), 2.16–2.24 (m, 1H), 2.80–3.1 3.34–3.40 (m, 1H), 4.52 (m, 1H), 6.52 (m, 2H), 6.67(dd, J=2.4, 1.0 Hz, 1H), 6 2H), 7.11 (tt, J=7.5, 1.7 Hz, 1H), 7.23 (t, J=7.8 Hz, 1H), 7.35 (m, 2H) ppm. MS (DCl/$NH_3$) m/z 296 (M+H)$^+$.

Example 1B

3-(3-phenoxyphenoxy)quinuclidine hydrochloride

The product of 1A (250 mg, 0.85 mmol) in ethyl acetate (5 mL) was treated with 4M HCl in 1,4-dioxane (0.5 mL, 2 mmol) to provide title compound as a solid (165 mg, 59% yield). $^1$H NMR (MeOH-$d_4$, 300 MHz) δ 1.72–2.20 (m, 3H), 2.25–2.34 (m, 1H), 2.50 (m, 1H), 3.30–3.45 (m, 5H), 3.78 (m, 1H), 4.90 (m, 1H), 6.60(m, 6.72 (ddd, J=8.1, 2.3, 0.7 Hz, 1H), 6.99 (m, 1H), 7.13 (tt, J=7.1, 1.0 Hz, 1H), 7.25–7.39(m, 3H) ppm. MS (DCl/$NH_3$) m/z 296(M+H)$^+$. Anal. calculated for $C_{19}H_{21}NO_2$.1.0HCl.0.3$H_2O$: C, 67.67; H, 6.75; N, 4.15. Found: C, 67.56; H, 6.45 4.26.

Example 2

3-(4-phenoxyphenoxy)quinuclidine hydrochloride

Example 2A

3-(4-phenoxyphenoxy)quinuclidine

3-Hydroxy quinuclidine (Aldrich, 254 mg, 2 mmol) was treated with 1-iodo-4-phenoxy-benzene (Aldrich, 296 mg, 1 mmol), CuI (Strem Chemicals, 19 mg, 0.1 mmol), 1,10-phenanthroline (Aldrich, 36 mg, 0.2 mmol), and $Cs_2CO_3$ (660 mg, 2.0 mmol) in toluene (anhydrous, Aldrich, 10 mL) and heated at 110° C. for two days. After cooling to room temperature, the reaction mixture was diluted with ethyl acetate (50 mL) and washed with water (2×10 mL). The organic phase was concentrated and the title compound was purified by chromatography ($SiO_2$, $CH_2Cl_2$:MeOH:$NH_3H_2O$, 90:10:1, $R_f$ 0.20) as oil (220 mg, yield, 75%). $^1$H NMR (MeOH-$d_4$, 300 MHz) δ 1.45–1.58 (m, 1H), 1.64–1.85 (m, 2H), 2.00–2.15 (m, 1H), 2.20–2.30 (m, 2.70–3.10 (m, 5H), 3.34–3.40 (m, 1H), 4.52 (m, 1H), 6.83–6.98 (m, 6H), 7.03 (tt, J=7.5, 1.0 Hz, 1H), 7.20–7.41 (m, 2H) ppm. MS (DCl/$NH_3$) m/z 296 (M+H)$^+$.

Example 2B

3-(4-phenoxyphenoxy)quinuclidine hydrochloride

The product of 2A (220 mg, 0.75 mmol) in ethyl acetate (5 mL) was treated with 4M HCl in 1,4-dioxane (0.5 mL, 2 mmol) to provide the title compound as a solid (171 mg, yield, 69%). $^1$H NMR (MeOH-$d_4$, 300 MHz) δ 1.80–2.20 (m, 3H), 2.30–2.40 (m, 1H), 2.50 (m, 1H), 3.30–3.45 (m, 5H), 3.76 (m, 1H), 4.90 (m, 1H), 6.90-6H), 7.05–7.09(m, 1H) 7.20–7.42 (m, 2H) ppm. MS (DCl/$NH_3$) m/z 296(M+H)$^+$. An calculated for $C_{19}H_{21}NO_2$.1.0HCl: C, 68.77; H, 6.68; N, 4.22. Found: C, 68.56; H, 6.45; N, 4.26.

Example 3

(R)-3-(4-phenoxyphenoxy)quinuclidine hydrochloride

Example 3A

(R)-3-(4-phenoxyphenoxy)quinuclidine 3-(R)-Hydroxy-quinuclidine (the product of Reference Example 1, 152 mg, 1.2 mmol), was coupled with 1-iodo-4-phenoxy-benzene (178 mg, 0.6 mmol) according to the procedure of Example 3A. The title product was purified by chromatography (SiO$_2$, CH$_2$Cl$_2$:MeOH:NH$_3$.H$_2$O, 90:10:1, R$_f$ 0.20) as oil (25 mg, yield, 14%). $^1$H NMR (MeOH-d$_4$, 300 MHz) δ 1.45–1.58 (m, 1H), 1.64–1.85 (m, 2H), 2.00–2.15 (m, 1H), 2.20–2.30 (m, 1H), 2.70–3.10 (m, 5H), 3.34–3.40 (m, 1H), 4.52 (m, 1H), 6.83–6.98 (m, 6H), 7.03 (tt, J=7.5, 1.0 Hz, 1H), 7.30 (t, J=7.5 Hz, 2H) ppm. MS (DC m/z 296 (M+H)$^+$.

Example 3B (R)-3-(4-phenoxyphenoxy)quinuclidine hydrochloride

The product of Example 3A (20 mg, 0.07 mmol) in ethyl acetate (4 mL) was treated with 4M HCl in 1,4-dioxane (0.5 mL) to provide the title compound as a solid (20 mg, yield, 90%). $^1$H NMR (MeOH-d$_4$, 300 MHz) δ 1.80–2.20 (m, 3H), 2.30–2.40 (m, 1H), 2.50 (m, 1H), 3.30–3.45 (m, 5H), 3.76 (m, 1H), 4.90 (m, 1H), 6.90–6H), 7.05–7.09 (m, 1H), 7.20–7.42 (m, 2H) ppm. MS (DCl/NH$_3$) m/z 296(M+H)$^+$. A calculated for C$_{19}$H$_{21}$NO$_2$.1.0HCl.0.4H$_2$O: C, 67.31; H, 6.78; N, 4.13. Found: C, 67.03; H, 6.41; N, 3.93.

Example 4

(S)-3-(4-phenoxyphenoxy)quinuclidine hydrochloride

Example 4A (S)-3-(4-phenoxyphenoxy)quinuclidine 3-(R)-Hydroxy-quinuclidine (the product of Reference Example 1, 152 mg, 1.2 mmol), was treated with 1-iodo-4-phenoxy-benzene (178 mg, 0.6 mmol) according to the procedure of Example 3A to provide the title compound. (80 mg, yield, 45.2%). $^1$H NMR (MeOH-d$_4$, 300 MHz) δ 1.45–1.58 (m, 1H), 1.64–1.85 (m, 2H), 2.00–2.15 (m, 1H), 2.20–2.30 (m, 1H), 2.70–3.10 (m, 5H), 3.34–3.40 (m, 1H), 4.52 (m, 1H), 6.83–6.98 (m, 6H), 7.03 (tt, J=7.5, 1.0 Hz, 1H), 7.30 (t, J=7.5 Hz, 2H) ppm. MS (D m/z 296 (M+H)$^+$.

Example 4B (S)-3-(4-phenoxyphenoxy)quinuclidine hydrochloride

The product of Example 4A (80 mg, 0.27 mmol) in ethyl acetate (4 mL) was treated with 4M HCl in 1,4-dioxane (0.5 mL) to provide the title compound as solid (57 mg, yield, 63%). $^1$H NMR (MeOH-d$_4$, 300 MHz) δ 1.80–2.20 (m, 3H), 2.30–2.40 (m, 1H), 2.50 (m, 1H), 3.30–3.45 (m, 5H), 3.76 (m, 1H), 4.90 (m, 1H), 6.90–6H), 7.05–7.09 (m, 1H), 7.20–7.42 (m, 2H) ppm. MS (DCl/NH$_3$) m/z 296(M+H)$^+$. A calculated for C$_{19}$H$_{21}$NO$_2$. 1.0HCl: C, 68.77; H, 6.68; N, 4.22. Found: C, 68.50; H, 6.69; N, 4.12.

Example 5

3-{4-[4-(trifluoromethyl)phenoxy]phenoxy}quinuclidine hydrochloride

Example 5A

3-{4-[4-(trifluoromethyl)phenoxy]phenoxy}quinuclidine

3-Hydroxy quinuclidine (Aldrich, 254 mg, 2 mmol) was treated with 4-(4-trifluoromethyl-phenoxy)-phenol (Aldrich, 255 mg, 1 mmol) according to the procedure of Example 1A. The title compound was purified by chromatography (SiO$_2$, CH$_2$Cl$_2$:MeOH:NH$_3$.H$_2$O, 90:10:1, R$_f$ 0.50) as oil (180 mg, yield, 49%). $^1$H NMR (MeOH-d$_4$, 300 MHz) δ 1.50–1.58 (m, 1H), 1.64–1.85 (m, 2H), 2.00–2.15 (m, 1H), 2.20–2.30 (m, 1H), 2.76–3.10 (m, 5H), 3.38–3.50 (m, 1H), 4.60 (m, 1H), 6.96–7.04 (m, 6H), 7.60 (d, J=8.5 Hz, 2H) ppm. MS (DCl/NH$_3$) m/z 364 (M+H)$^+$.

Example 5B

3-{4-[4-(trifluoromethyl)phenoxy]phenoxy}quinuclidine hydrochloride

The product of 5A (180 mg, 0.49 mmol) in ethyl acetate (5 mL) was treated with 4M HCl in 1,4-dioxane (0.5 mL, 2 mmol) to provide the title compound as a solid (110 mg, yield, 56%). $^1$H NMR (MeOH-d$_4$, 300 MHz) δ 1.80–2.28 (m, 3H), 2.35–2.40 (m, 1H), 2.56 (m, 1H), 3.30–3.45 (m, 5H), 3.80 (m, 1H), 4.94 (m, 1H), 7.02–7.10 (m, 6H), 7.60 (d, J=8.4 Hz, 2H) ppm. MS (DCl/NH$_3$) m/z 364(M+H)$^+$. Anal. calculated for C$_{20}$H$_{20}$F$_3$NO$_2$.1.0HCl.0.5H$_2$O: C, 58.76; H, 5.42; N, 3.43. Found: C, 58.54; H, N, 3.35.

Example 6

3-[4-(4-fluorophenoxy)phenoxy]quinuclidine hydrochloride

Example 6A

3-[4-(4-fluorophenoxy)phenoxy]quinuclidine

3-Hydroxy quinuclidine (Aldrich, 254 mg, 2 mmol) was treated with 4-(4-fluoro-phenoxy)-phenol (Aldrich, 205 mg, 1 mmol) according to the procedure of Example 1A. The title compound was purified by chromatography (SiO$_2$, CH$_2$Cl$_2$:MeOH:NH$_3$.H$_2$O, 90:10:1, R$_f$ 0.45) as oil (230 mg, yield, 73%). $^1$H NMR (MeOH-d$_4$, 300 MHz) δ 1.40–1.52 (m, 1H), 1.64–1.87 (m, 2H), 1.98–2.15 (m, 1H), 2.20–2.25 (m, 1H), 2.66–3.00 (m, 5H), 3.30–3.40 (m, 1H), 4.48(m, 1H), 6.61 (dt, J=10.5, 2.4 Hz, 1H), 6.71(dd, J=8.1, 2.3 Hz, 1H), 6.76 (tdd, J=8.4, 2.3, 1.0 Hz, 1H), 6.87–7.00 (m, 3H), 7.22–7.32 (m, 2H) ppm. MS (DCl/NH$_3$) m/z 314 (M+H)$^+$.

Example 6B

3-[4-(4-fluorophenoxy)phenoxy]quinuclidine hydrochloride

The product of Example 6A (230 mg, 0.73 mmol) in ethyl acetate (5 mL) was treated with 4M HCl in 1,4-dioxane (0.5 mL, 2 mmol) to provide the title compound as a solid (106 mg, yield, 42%). $^1$H NMR (MeOH-d$_4$, 300 MHz) δ 1.79–2.21 (m, 3H), 30 2.32–2.40 (m, 1H), 2.56 (m, 1H), 3.30–3.48 (m, 5H), 3.80 (m, 1H), 4.90 (m, 6.62(dt, J=10.5, 2.4 Hz, 1H), 6.73(dd, J=8.1, 2.3Hz, 1H), 6.78 (tdd, J=8.5, 2.3, 1.0 Hz, 1H), 7.03 (s, 4H), 7.30 (td, J=8.2, 6.7Hz, 1H) ppm. MS (DCl/NH$_3$) m/z 314 (M+H)$^+$. Anal. calculated for C$_{19}$H$_{20}$FNO$_2$.1.0HCl: C, 65.23; H, 6.05; N, 4.00. Found: C, 64.96; H, 6.17; N, 3.96.

Example 7

4-[4-(1-azabicyclo[2.2.2]oct-3-yloxy)phenoxy]phenol hydrochloride

Example 7A

4-[4-(1-azabicyclo[2.2.2]oct-3-yloxy)phenoxy]phenol

3-Hydroxy quinuclidine (Aldrich, 254 mg, 2 mmol) was treated with 4,4'-dihydroxydiphenyl ether (TCI, 202 mg, 1 mmol) according to the procedure of Example 1A. The title compound was purified by chromatography (SiO₂, CH₂Cl₂: MeOH:NH₃ H₂O, 90:10:1, $R_f$ 0.2) as oil (210 mg, yield, 68%). ¹H NMR (MeOH-d₄, 300 MHz) δ 1.40–1.55 (m, 1H), 1.60–1.87 (m, 2H), 1.98–2.15 (m, 1H), 2.20–2.25 (m, 1H), 2.75–2.98 (m, 5H), 3.20–3.30 (m, 1H), 4.45(m, 1H), 6.62–6.96 (m, 8(DCl/NH₃) m/z 312 (M+H)⁺.

Example 7B

4-[4-(1-azabicyclo[2.2.2]oct-3-yloxy)phenoxy]phenol hydrochloride

The product of Example 7A (210 mg, 0.68 mmol) in ethyl acetate (5 mL) was treated with 4M HCl in 1,4-dioxane (0.5 mL, 2 mmol) to provide the title compound as a solid (140 mg, yield, 59%). ¹H NMR (MeOH-d₄, 300 MHz) δ 1.73–2.19 (m, 3H), 2.21–2.40 (m, 1H), 2.41–2.56 (m, 1H), 3.30–3.50 (m, 5H), 3.69–3.83 (m, 1H), 4.80 (m, 1H), 6.59–7.04 (m, 8H) ppm. MS (DCl/NH₃) m/z 312 (M+H)⁺. Anal. calculated for $C_{19}H_{21}NO_3 \cdot 1.0HCl$: C, 65.61; H, 6.37; N, 4.03. Found: C, 65.31; H, 6.32; N, 3.86.

Example 8

4,4'-di (1-aza-bicyclo[2.2.2]oct-3-yloxy)-diphenyl ether bis(hydrochloride)

3-Hydroxy quinuclidine (Aldrich, 254 mg, 2 mmol) was treated with 4,4'-dihydroxydiphenyl ether (TCl, 202 mg, 1 mmol) according to the procedure of Example 7A. The free base of title compound was purified by chromatography (SiO₂, CH₂Cl₂:MeOH:NH₃ H₂O, 90:10:1, $R_f$ 0.4) as oil (60 mg, yield, 7%). It was then treated with HCl (Aldrich, 4 M in dioxane, 0.25 mL, 1 mmol) in EtOAc (5 mL) at ambient temperature for 1 hour to give the title compound as solid (40 mg, yield, 59%) ¹H NMR (MeOH-d₄, 300 MHz) δ 1.78–2.21 (m, 3H), 2.21–2.39 (m, 1H), 2.39–2.62 (m, 1H), 3.29–3.49 (m, 5H), 3.79 (dd, J=13.7, 8.6 Hz, 1H), 4.73–4.93 (m, 1H), 6.78–7.10 (m, 4H) ppm. MS (DCl/NH₃) m/z 421 (M+H)⁺.

Example 9

4-{4-[(3R)-1-azabicyclo[2.2.2]oct-3-yloxy]phenoxy}phenol fumarate

Example 9A

4-{4-[(3R)-1-azabicyclo[2.2.2]oct-3-yloxy]phenoxy}phenol 3-(S)-Hydroxy-quinuclidine (the product of Reference Example 2D, 127 mg, 1 mmol) was treated with 4,4'-dihydroxydiphenyl ether (TCl, 202 mg, 1 mmol) according to the procedure of Example 1A. The title compound was purified by chromatography (SiO₂, CH₂Cl₂:MeOH: NH₃.H₂O, 90:10:1, $R_f$ 0.2) as oil (48 mg, yield, 15%). ¹H NMR (MeOH-d₄, 300 MHz) δ 1.40–1.55 (m, 1H), 1.60–1.87 (m, 2H), 1.98–2.15 (m, 1H), 2.20–2.25 (m, 1H), 2.75–2.98 (m, 5H), 3.20–3.30 (m, 1H), 4.45 (m, 1H), 6.62–6.96 (m, 8H) ppm. MS (DCl/NH₃) m/z 312 (M+H)⁺.

Example 9B

4-{4-[(3R)-1-azabicyclo[2.2.2]oct-3-yloxy]phenoxy}phenol fumarate

The product of Example 9A (48 mg, 0.15 mmol) in ethyl acetate:MeOH (3 mL, 10:1) was treated with fumaric acid (Aldrich, 17.4 mg, 0.15 mmol) at room temperature and stirred overnight to provide the title compound as a solid (34 mg, yield, 62%). ¹H NMR (MeOH-d₄, 300 MHz) δ 1.73–2.19 (m, 3H), 2.21–2.40 (m, 1H), 2.41–2.56 (m, 1H), 3.03–3.27 (m, 5H), 3.59–3.73 (m, 1H), 4.67 (m, 1H), 6.67 (s, 1H), 6.67–6.98 (m, 8H) ppm. MS (DCl/NH₃) m/z 312 (M+H)⁺. Anal. Calculated for $C_{19}H_{21}NO_3 \cdot 0.5C_4H_4O_4 \cdot 0.35H_2O$ C, 67.13; H, 6.36; N, 3.73. Found: C, 67.04; H, 6.46; N, 3.75.

Example 10

4-{[4-(1-azabicyclo[2.2.2]oct-3-yloxy)phenyl]thio}phenol hydrochloride

Example 10A

4-{[4-(1-azabicyclo[2.2.2]oct-3-yloxy)phenyl]thio}phenol

3-Hydroxy quinuclidine (Aldrich, 254 mg, 2 mmol) was treated with 4,4'-dihydroxydiphenyl thioether (TCl, 218 mg, 1 mmol) according to the procedure of Example 1A. The title compound was purified by chromatography (SiO₂, CH₂Cl₂:MeOH:NH₃.H₂O, 90:10:1, $R_f$ 0.2) as oil (280 mg, yield, 86%). ¹H NMR (MeOH-d₄, 300 MHz) δ 1.40–1.50 (m, 1H), 1.55–1.87 (m, 2H), 1.90–2.15 (m, 2H), 2.70-5H), 3.20–3.30 (m, 1H), 4.46(m, 1H), 6.74 (d, J=8.9 Hz, 2H), 6.83 (d, J=9. 7.17 (d, J=8.8 Hz, 2H), 7.19 (d, J=8.8 Hz, 2H) ppm. MS (DCl/NH₃) m/z 328 (M+H)⁺

Example 10B

4-{[4-(1-azabicyclo[2.2.2]oct-3-yloxy)phenyl]thio}phenol hydrochloride

The product of Example 10A (200 mg, 0.61 mmol) in ethyl acetate (5 mL) was treated with 4M HCl in 1,4-dioxane (0.5 mL, 2 mmol) to provide the title compound as a solid (140 mg, yield, 63%). ¹H NMR (MeOH-d₄, 300 MHz) δ 1.75–2.19 (m, 3H), 2.19–2.38 (m, 1H), 2.43–2.56 (m, 1H), 3.20–3.50 (m, 5H), 3.66–3.84 (m, 1H), 6.76 (d, J=8.9 Hz, 2H), 6.90 (d, J=8.9 Hz, 2H), 7.19 (d, J=8.8 Hz, 2H), 7.22 (d, J=8.8 Hz, 2H) ppm. MS (DCl/NH₃) m/z 328 (M+H)⁺. Anal. calculated for $C_{19}H_{21}NO_2S \cdot 1.0HCl \cdot 0.8H_2O$: C, 60.32; H, 6.29; N, 3.70. Found: C, 60.34; H, 6.N, 3.32.

Example 11

4-({4-[(3R)-1-azabicyclo[2.2.2]oct-3-yloxy]phenyl}thio)phenol fumarate

Example 11A 4-({4-[(3R)-1-azabicyclo[2.2.2]oct-3-yloxy]phenyl}thio)phenol 3-(S)-Hydroxy-quinuclidine (the product of Reference Example 2D, 127 mg, 1 mmol) was treated with 4,4'-dihydroxydiphenyl thioether (TCl, 202 mg, 1 mmol) according to the procedure of Example 1A. The title compound was purified by chromatography (SiO₂, CH₂Cl₂:MeOH: NH₃.H₂O, 90:10:1, $R_f$ 0.2) as oil (38 mg, yield, 12%). ¹H NMR (MeOH-d₄, 300 MHz) δ 1.40–1.50 (m, 1H), 1.55–1.87 (m, 2H), 1.90–2.15 (m, 2H), 2.70–2.98 (m, 5H), 3.20–3.30 (m, 1H), 4.47(m, 1H), 6.72 Hz, 2H), 6.83 (d, J=9.1 Hz, 2H), 7.15–7.20 (m, 4H) ppm. MS (DCl/NH₃) m/z 328 (M+H)⁺.

Example 11B

4-({4-[(3R)-1-azabicyclo[2.2.2]oct-3-yloxy]phenyl}thio)phenol fumarate

The product of Example 11A (38 mg, 0.12 mmol) in ethyl acetate:MeOH (5 mL, 10:1) was treated with fumaric acid 17.4 mg (0.15 mmol) at room temperature overnight. The title compound was obtained as a solid (30 mg, yield, 66%). $^1$H NMR (MeOH-$d_4$, 300 MHz) δ 1.75–2.19 (m, 3H), 2.19–2.38 (m, 1H), 2.33–2.46 (m, 1 3.03–3.27 (m, 5H), 3.50–3.64 (m, 1H), 4.70 (m, 1H), 6.67 (s, 1H), 6.76 (d, J=8.9 Hz, 2H), 6.87 (d, J=8.9 Hz, 2H), 7.15–7.26 (m, 4H) ppm. MS (DCl/NH$_3$) m/z 328 (M+H)$^+$. Anal. Calculated for $C_{19}H_{21}NO_2S \cdot 0.5C_4H_4O_4 \cdot 0.4H_2O$ C, 64.23; H 6.11; N, 3.57. Found: C, 64.14; H, 5.83; N, 3.49.

Example 12

4,4'-di[(3R)-1-aza-bicyclo[2.2.2]oct-3-yloxy]-diphenyl thioether tri(hydrochloride)

Example 12A

4,4'-di[(3R)-1-aza-bicyclo[2.2.2]oct-3-yloxy]-diphenyl thioether 3-(S)-Hydroxy-quinuclidine (the product of Reference Example 2D, 508 mg, 4.0 mmol) was treated with 4,4'-dihydroxydiphenyl thioether (TCl, 872 mg, 4.0 mmol) according to the procedure of Example 11A. The title compound the was purified via column chromatography (SiO$_2$,CH$_2$Cl$_2$/MeOH (v.2% NH$_3$.H$_2$O), 90/10, 10% Rf=0.08) (110 mg, yield, 6%).$^1$H NMR (MeOH-$d_4$, 300 MHz) 1.37–1.88 (m, 6H), 1.90–2.06 (m, 2H), 2.08–2.18 (m, 2H), 2.64–3.00 (m, 10H), 3.08–3.18 (m, 4.45–4.52 (m, 2H), 6.85 (d, J=8.8 Hz, 4H), 7.24 (d, J=8.8 Hz, 4H) ppm. MS (DCl/N m/z 437 (M+H)$^+$.

Example 12B

4,4'-di[(3R)-1-aza-bicyclo[2.2.2]oct-3-yloxy]-diphenyl thioether tri(hydrochloride)

The product of Example 12A (110 mg, 0.25 mmol) was treated with HCl (Aldrich, 4 M in dioxane, 0.5 mL, 2 mmol) in EtOAc (5 mL) at ambient temperature for 16 hours to give the title compound (53.3 mg, 39%). $^1$H NMR (MeOH-$d_4$, 300 MHz) 1.80–2.17 (m, 6H), 2.22–2.35 (m, 2H), 2.45–2.53 (m, 2H), 3.25–3.45 (m 10H), 3.80 (dd, J=13.7, 8.3 Hz, 2H), 4.84–4.91 (m, 2H), 6.95 (d, J=8.8 Hz, 4H), 7.29 (d, J=8.8 Hz, 4H) ppm. MS (DCl/NH$_3$) m/z 437 (M+H)$^+$. Anal. Calculated for $C_{26}H_{32}N_2O_2S \cdot 3.0$ HCl: C, 57.20; H, 6.46; N, 5.13. Found: C, 57.35; H, 6.42; N, 4.97.

Example 13

3-{4-[(4-isopropoxyphenyl)thio]phenoxy}quinuclidine fumarate

Example 13A

3-{4-[(4-isopropoxyphenyl)thio]phenoxy}quinuclidine

The product of Example 10A (80 mg, 0.24 mmol) was treated with isopropyl alcohol (60 mg, 1 mmol) according to the procedure of Example 1A. The title compound was purified by chromatography (SiO$_2$, CH$_2$Cl$_2$:MeOH: NH$_3$.H$_2$O, 90:10:1, R$_f$, 0.5) as oil (80 mg, yield, 90%). $^1$H NMR (MeOH-$d_4$, 300 MHz) δ 1.30 (d, J=6.1 Hz, 6H), 1.60–2.10 (m, 3H), 2.15–2.25 (m, 1H), 2.30–2.40 (m, 2H), 2,98–3.20 (m, 6H), 3.50–3.60 (m, 1H), 4.50–4.58(m, 1H), 7.70–4.78 (m, 1H), 6.87 (t, J =9.2 Hz), 4H), 7.23 (d, J=8.8 Hz, 2H), 7.24 (d, J=9.2 Hz, 2H) ppm. MS (DCl/NH$_3$) m/z 370 (M+H)$^+$.

Example 13B

3-{4-[(4-isopropoxyphenyl)thio]phenoxy}quinuclidine fumarate

The product of Example 13A (74 mg, 0.2 mmol) in ethyl acetate:MeOH (5 mL, 10:1) was treated with fumaric acid (Aldrich, 21 mg, 0.2 mmol). The title compound was obtained as solid (90 mg, yield, 95%): $^1$H NMR (MeOH-$d_4$, 300 MHz) δ 1.75–2.19 (m, 3H), 2.19–2.38 (m, 1H), 2.43–2.56 (m, 1H), 3.20–3.50 (m, 5H), 3.66–3.84 (m, 1H), 4.80 (m, 1H), 6.76 (d, J=8.9 Hz, 2H), 6.90 (d, J=8.9 Hz, 2H), 7.19 (d, J=8.8 Hz, 2H), 7.22 (d, J=8.8 Hz, 2H) ppm. MS (DCl/NH$_3$) m/z 370 (M+H)$^+$. Anal. Calculated for $C_{22}H_{27}NO_2S \cdot 1.0 C_4H_4O_4 \cdot 0.4H_2O$: C, 63.37; H, 6.50; N, 2.84 63.57; H, 6.20; N, 2.80.

Example 14

3-[4-(pyridin-3-yloxy)phenoxy]quinuclidine hydrochloride

Example 14A

3-(4-iodophenoxy)quinuclidine

3-Hydroxy quinuclidine (Aldrich, 2.54 g, 20 mmol) in toluene (anhydrous, Aldrich, 50 mL) was treated with 1,4-diiodobenzene (Aldrich, 7.9 g, 24 mmol), CuI (Strem Chemicals, 0.38 g, 2 mmol), 1,10-phenanthroline (Aldrich, 0.72 g, 4 mmol), and Cs$_2$CO$_3$ (Aldrich, 8.15 g, 25 mmol), heated at 110° C. for 40 hours. The reaction mixture was allowed to cool to room temperature, diluted with chloroform (100 mL), and washed with water (2×10 mL). The organic phase was concentrated and the title compound was purified by chromatography (SiO$_2$, CH$_2$Cl$_2$:MeOH: NH$_3$.H$_2$O, 90:10:1, R$_f$, 0.20) as oil (3.7 g, yield, 56%). $^1$H NMR (MeOH-$d_4$, 300 MHz) δ 1.40–1.56 (m, 1H), 1.64–1.80 (m, 2H), 1.90–2.08 (m, 1H), 2.10–2.21 (m, 1H), 2.60–3.00 (m, 5H), 3.34–3.40 (m, 1H), 4.46 (m, 1H), 6.73 (d, J=8.8 Hz, 2H), 7.56 (d, J=8.8, Hz, 2H), ppm. MS (DCl/NH$_3$) m/z 330 (M+H)$^+$.

Example 14B

3-(4-iodophenoxy)quinuclidine hydrochloride

The product of Example 14A (3.7 g, 11.2 mmol) in ethyl acetate (50 mL) was treated with 4M HCl in 1,4-dioxane (5 mL, 20 mmol). The title compound was obtained as a solid (4.0 g, yield, 98%). $^1$H NMR (MeOH-$d_4$, 300 MHz) δ 1.80–2.20 (m, 3H), 2.30–2.40 (m, 1H), 2.50 (m, 1H), 3.30–3.48 (m, 5H), 3.76 (m, 1H), 4.92 (m, 1H), 6.80 (d, J=9.1 Hz, 2H), 7.61 (d, J=8.8 Hz, 2H) ppm. MS (DCl/NH$_3$) m/z 330 (M+H)$^+$. Anal. calculated for $C_{13}H_{16}INO \cdot 1.0HCl$: C, 42.70; H, 4.69; N, 3.83. Found: C, 42.72; H, 4.61; N, 3.65.

Example 14C

3-[4-(Pyridin-3-yloxy)phenoxy]quinuclidine hydrochloride

The product of Example 14B (365 mg, 1.0 mmol) in N-methylpyrrolidin-2-one (2 mL) was treated with 3-hydroxypyridine (Aldrich, 190 mg, 2.0 mmol), CuCl (Strem Chemicals, 45 mg, 0.5 mmol), 2,2,6,6-tetramethyl-heptane-3,5-dione (Strem Chemicals, 37 mg, 0.2 mmol), $Cs_2CO_3$ (Strem Chemicals, 650 mg, 2 mmol) and heated at 160° C. for 6 hours. The mixture was allowed to cool to room temperature, diluted with $CH_2Cl_2$ (5 mL), filtered, and the filtrate was directly purified by chromatography ($SiO_2$, $CH_2Cl_2$:MeOH:$NH_3$.$H_2O$, 90:10:1, $R_f$, 0.20) to provide the title compound as an oil (230 mg, yield, 78%). The title compound in ethyl acetate (5 mL) was treated with 4M HCl in 1,4-dioxane (0.5 mL, 2 mmol) to provide the dihydrochloride salt as a solid (210 mg, yield, 74%). $^1$H NMR (MeOH-$d_4$, 300 MHz) δ 1.80–2.22 (m, 3H), 2.30–2.40 (m, 1H), 2.55–2.65 (m, 1H), 3.30–3.46 (m, 5H), 3.76–3.86 (m, 1H), 4.96 (m, 1H), 7.15 (d, J=9.2 Hz, 2H), 7.22 (d, J=9.1 Hz, 2H) 8.00(dd, J=8.5, 5.1 Hz, 1H), 8.13 (ddd, J=8.8, 2.7, 1.0 Hz, 1H), 8.55 (d, J=5.4 Hz, 1H), 8.59 (d, J=2.7 Hz, 1H) ppm. MS (DCl/$NH_3$) m/z 297 (M+H)$^+$. Anal. Calculated for $C_{18}H_{20}N_2O_2$.2.0HCl: C, 58.54; H, 6.00; N, 7.59. Found: C, 58.18; H, 6.13; N, 7.31.

Example 15

3-[4-(thien-3-yloxy)phenoxy]quinuclidine hydrochloride

Example 15A

3-[4-(benzyloxy)phenoxy]quinuclidine

3-Hydroxy quinuclidine (Aldrich, 2.54 9, 20 mmol) was treated with 1-benzyloxy-4-iodo-benzene (Aldrich, 3.10 g, 10 mmol) according to the procedure of Example 14A. The title compound was purified by chromatography ($SiO_2$, $CH_2Cl_2$:MeOH:$NH_3$.$H_2O$, 90:10:2, $R_f$, 0.40) as an oil (1.30 g, yield, 42%). $^1$H NMR (MeOH-$d_4$, 300 MHz) δ 1.45–1.56 (m, 1H), 1.64–1.80 (m, 2H), 2.00–2.10 (m, 1H), 2.15–2.24 (m, 1H), 2.76–3.10 (m, 5H), 3.40–3.46 (m, 1H), 4.48 (m, 1H), 5.10 (s, 2H), 6.73–6.96 (m 4H), 7.20–7.40 (m, 5H) ppm. MS (DCl/$NH_3$) m/z 310 (M+H)$^+$.

Example 15B

3-[4-(benzyloxy)phenoxy]quinuclidine hydrochloride

The product of Example 15A (100 mg, 0.32 mmol) in ethyl acetate (5 mL) was treated with 4M HCl in 1,4-dioxane (0.5 mL, 2.0 mmol). The title compound was obtained as a solid (80 mg, yield, 72%). $^1$H NMR (MeOH-$d_4$, 300 MHz) δ 1.80–2.16 (m, 3H), 2.25–2.40 (m, 1H), 2.46 (m, 1H), 3.30–3.46 (m, 5H), 3.76 (m, 1H), 4.75 (m, 1H), 5.02 (s, 2H), 6.80–6.95 (m, 4H), 7.28–7.40 (m, 5H) ppm. MS (DCl/$NH_3$) m/z 310 (M+H)$^+$. Anal. calculated for $C_{20}H_{23}NO_2$.1.4HCl.0.8$H_2O$: C, 64.08; H, 6.99; N, 3.74. Found: C, 64.14; H, 6.52; N, 3.86.

Example 15C

4-(1-azabicyclo[2.2.2]oct-3-yloxy)phenol

The product of Example 15A (1.20 g, 3.9 mmol) in ethanol (20 mL) was treated with Pd/C (Aldrich, 10% wt., 0.2 g) under $H_2$ at ambient temperature for 10 hours. The mixture filtered through a short column of diatomaceous earth and the filtrate was concentrated under reduced pressure to provide the title compound as a colorless oil (0.72, yield, 84%). $^1$H NMR (MeOH-$d_4$, 300 MHz) δ 1.40–1.56 (m, 1H), 1.64–1.75 (m, 1H), 1.80–1.92 (m, 1H), 2.00–2.30 (m, 2H), 2.76–3.02 (m, 5H), 3.25–3.35 (m, 1H), 4.40 (m, 1H), 6.60–6.80 (m, 4H) ppm. MS (DCl/$NH_3$) m/z 220 (M+H)$^+$.

Example 15D

4-(1-azabicyclo[2.2.2]oct-3-yloxy)phenol hydrochloride

The product of Example 15C (66 mg, 0.3 mmol) in ethyl acetate (4 mL) was treated with 4M HCl in 1,4-dioxane (0.2 mL, 0.8 mmol). The title compound was obtained as a solid (80 mg, yield, 92%). $^1$H NMR (MeOH-$d_4$, 300 MHz) δ 1.80–2.10 (m, 3H), 2.25–2.40 (m, 1H), 2.46 (m, 1H), 3.30–3.46 (m, 5H), 3.68 (m, 1H), 4.70 (m, 1H), 6.72 (dt, J=9.1, 2.4 Hz, 2H), 6.82 (dt, J=9.2, 2.7 Hz, 2H) ppm. MS (DCl/$NH_3$) m/z 220 (M+H)$^+$. Anal. Calculated for $C_{13}H_{17}NO_2$.1.0HCl.0.1$H_2O$: C, 60.63; H, 7.12; N, 5.44. Found: C, 60.66; H, 7.10; N, 5.28.

Example 15E

3-[4-(thien-3-yloxy)phenoxy]quinuclidine

The product of Example 15C (110 mg, 0.5 mmol) in N-methylpyrrolidin-2-one (2 mL) was treated with 3-iodothiophene (Aldrich, 209 mg, 1 mmol) according to the procedure of Example 14C. The title compound was purified by chromatography ($SiO_2$, $CH_2Cl_2$:MeOH:$NH_3$.$H_2O$, 90:10:2, $R_f$, 0.30) as oil (40 mg, yield, 26%). $^1$H NMR (MeOH-$d_4$, 300 MHz) δ 1.50–1.60 (m, 1H), 1.64–1.92 (m, 2H), 2.06–2.15 (m, 1H), 2.20–2.28 (m, 1H), 2.80–3.10 (m, 5H), 3.40–3.46 (m, 1H), 4.55 (m, 1H), 6.51 (dd, J=3.4, 1.4 Hz, 1H), 6.80 (dd, J=5.2, 1.5 Hz, 1H), 6.91 (dt, J=9.4, 2.7 Hz, 2H), 6.99 (dt, J=9.2, 2.8 Hz, 2H), 7.33 (dd, J=5.4, 3.1 Hz, 1H) ppm. MS (DCl/$NH_3$) m/z 302 (M+H)$^+$.

Example 15F

3-[4-(thien-3-yloxy)phenoxy]quinuclidine hydrochloride

The product of Example 15E (40 mg, 0.13 mmol) in ethyl acetate (4 mL) was treated with 4M HCl in 1,4-dioxane (0.2 mL, 0.8 mmol). The title compound was obtained as a solid (26 mg, yield, 59%). $^1$H NMR (MeOH-$d_4$, 300 MHz) δ 1.80–2.10 (m, 3H), 2.25–2.46 (m, 1H), 2.56 (m, 1H), 3.30–3.50 (m, 5H), 3.80 (m, 1H), 4.85 (m, 1H), 6.55 (dd, J=3.4, 1.7 Hz, 1H), 6.81 (dd, J=5.5, 1.7 Hz, 1H), 6.97 (dt, J=9.5, 3.0 Hz, 2H), 7.02 (dt, J=9.5, 3.1 Hz, 2H), 7.34 (dd, J=5.1, 3.1 Hz, 1H) ppm. MS (DCl/$NH_3$) m/z 302 (M+H)$^+$. Anal. Calculated for $C_{17}H_{19}NO_2S$.1.0HCl.0.5$H_2O$: C, 58.86; H, 6.10; N, 4.04. Found: C, 59.08; H, 5.88; N, 4.06.

Example 16

3-{4-[(5-bromopyrimidin-2-yl)oxy]phenoxy}quinuclidine trifluroacetate

Example 16A

3-{4-[(5-bromopyrimidin-2-yl)oxy]phenoxy}quinuclidine

The product of Example 15C (110 mg, 0.5 mmol) in tetrahydrofuran (5 mL) was treated with potassium tert-butoxide (Aldrich, 1M in THF, 0.6 mL, 0.6 mmol) at ambient temperature for 5 minutes followed by addition of 5-bromo-2-iodo-pyrimidine (Aldrich, 142 mg, 0.5 mmol) and stirred at 60° C. for 10 hours. The reaction mixture was allowed to cool to room temperature, diluted with ethyl acetate (20 mL), and washed with brine (2×5 mL). The organic phase was concentrated under reduced pressure and the title compound was purified by chromatography ($SiO_2$, $CH_2Cl_2$:MeOH:$NH_3$.$H_2O$, 90:10:2, $R_f$ 0.40) as oil (100 mg, yield, 53%). $^1$H NMR (MeOH-$d_4$, 300 MHz) δ 1.50–1.60 (m, 1H), 1.64–1.92 (m, 2H), 2.06–2.15 (m, 1H), 2.20–2.28 (m, 1H), 2.80–3.10 (m, 5H), 3.40–3.46 (m, 1H), 4.55 (m, 1H), 7.30–7.45 (m, 2H), 7.52–7.60(m, 2H), 7.70–7.82(m, 2H) ppm. MS (DCl/$NH_3$) m/z 376 (M+H)$^+$, 378 (M+H) $^+$.

Example 16B

3-{4-[(5-bromopyrimidin-2-yl)oxy]phenoxy}quinuclidine trifluroacetate

The product of Example 16A (100 mg, 0.26 mmol) in ethyl acetate (4 mL) was treated with trifluroacetic acid (113 mg, 1 mmol). The title compound was obtained as solid (100 mg, yield, 64%). $^1$H NMR (MeOH-$d_4$, 300 MHz) δ 1.85–2.16 (m, 3H), 2.25–2.46 (m, 1H), 2.56 (m, 1H), 3.30–3.53 (m, 5H), 3.80 (m, 1H), 4.95 (m, 1H), 7.04 (dt, J=9.1, 2.4 Hz, 2H), 7.14 (dt, J=9.1, 2.3 Hz, 2H), 8.60 (s, 2H) ppm. MS (DCl/$NH_3$) m/z. m/z 376 (M+H)$^+$, 378 (M+H)$^+$. Anal. Calculated for $C_{17}H_{18}BrN_3O_2$.2.0$CF_3CO_2H$.2.0$H_2O$: C, 39.39; H, 3.78; N, 6.56. Found: C, 39.19; H, 3.78; N, 6.83.

Example 17

N-[4-(1-azabicyclo[2.2.2]oct-3-yloxy)phenyl]-N-phenylamine hydrochloride

Example 17A

N-[4-(1-azabicyclo[2.2.2]oct-3-yloxy)phenyl]-N-phenylamine

The product of Example 14B (370 mg, 1.0 mmol) in toluene (10 mL) was treated with aniline (Aldrich, 140 mg, 1.5 mmol), $Pd_2(dba)_3$ (Strem Chemicals, 18.3 mg, 0.02 mmol), 1,3-bis(2,6-di-i-propylphenyl)imidazolium chloride, 95%, 26.9 mg, 0.06 mmol), sodium tert-butoxide (Aldrich, 144 mg, 1.5 mmol) and heated at 110° C. for 15 hours. The reaction mxiture was was diluted with ethyl acetate (20 mL) and washed with brine (2×5 mL). The organic phase was concentrated and the title compound was purified by chromatography ($SiO_2$, $CH_2Cl_2$:MeOH:$NH_3$.$H_2O$, 90:10:1, $R_f$ 0.20) as oil (160 mg, yield, 53%). $^1$H NMR (MeOH-$d_4$, 300 MHz) δ 1.40–1.53 (m, 1H), 1.62–1.85 (m, 2H), 1.93–2.20 (m, 2H), 2.80–2.94 (m, 5H), 3.18–3.25 (m, 1H), 4.38–4.46 (m, 1H), 6.73 (tt, J=7.5, 3.0 Hz, 1H), 6.82 (dt, J=9.1, 3.4 Hz, 2H), 6.91–6.96 (m, 2H), 7.02 (dt, J=9.1, 2.4 Hz, 2H), 7.11–7.18 (m, 2H) ppm. MS (DCl/$NH_3$) m/z 295 (M+H)$^+$.

Example 17B

[N-[4-(1-azabicyclo[2.2.21]oct-3-yloxy)phenyl]-N-phenylamine hydrochloride

The product of Example 17A (160 mg, 0.53 mmol) in ethyl acetate (5 mL) was treated with 4M HCl in 1,4-dioxane (0.5 mL, 2 mmol). The title compound was obtained as a solid (150 mg, yield, 64%). $^1$H NMR (MeOH-$d_4$, 300 MHz) δ 1.85–2.20 (m, 3H), 2.30–2.42 (m, 1H), 2.45–2.52 (m, 1H), 3.30–3.45 (m, 5H), 3.70–80(m, 1H), 4.80 (m, 1H), 6.78 (tt, J=7.5, 3.0 Hz, 1H), 6.90 (dt, J=8.8, 3.4 Hz, 2H), 6.94–699 (m, 2H), 7.07 (dt, J=8.8, 3.3 Hz, 2H), 7.12–7.20 (m, 2H) ppm. MS (DCl/$NH_3$) m/z 295 (M+H)$^+$. Anal. Calculated for $C_{19}H_{22}N_2O$.2.0HCl.0.4$H_2O$: C, 67.50; H, 7.10; N, 8.29. Found: C, 67.34; H, 6.82; N, 8.03.

Example 18

N-{4-[(3R)-1-azabicyclo[2.2.2]oct-3-yloxy]phenyl}-N-phenylamine hydrochloride

Example 18A (3R)-3-(4-iodophenoxy)quinuclidine 3-(R)-Hydroxyquinuclidine (the product of Reference Example 1, 0.64 g, 5.0 mmol) was treated with 1,4-diiodobenzene (1.98 g, 6.0 mmol) according to the procedure of Example 14A. The title compound was purified by flash chromatography ($SiO_2$, $CH_2Cl_2$:MeOH:$NH_3$.$H_2O$, 90:10:1, $R_f$ 0.30) as a solid (0.50 g, yield, 15%). $^1$H NMR (MeOH-$d_4$, 300 MHz) δ 1.41–1.54 (m, 1H), 1.59–1.73 (m, 1H), 1.73–1.86 (m, 1H), 1.92–2.05 (m, 1H), 2.09–2.17 (m, 1H), 2.71–2.97 (m, 5H), 3.24–3.34 (m, 1H), 4.44–4.52 (m, 1H), 6.72 (d, J=8.8 Hz, 2H), 7.55 (d, J=9.2 Hz, 2H) ppm. MS (DCl/NH3): m/z 330 (M+H)$^+$.

Example 18B

N-{4-[(3R)-1-azabicyclo[2.2.21]oct-3-yloxy]phenyl}-N-phenylamine

The product of Example 18A (270 mg, 0.82 mmol) was treated with aniline (Aldrich, 114 mg, 1.23 mmol) according to the procedure of Example 17A. The title compound was purified by chromatography ($SiO_2$, $CH_2Cl_2$:MeOH:$NH_3$.$H_2O$, 90:10:1, $R_f$ 0.20) as an oil (130 mg, yield, 54%). $^1$H NMR (MeOH-$d_4$, 300 MHz) δ 1.40–1.53 (m, 1H), 1.62–1.85 (m, 2H), 1.93–2.20 (m, 2H), 2.80–2.94 (m, 5H), 3.18–3.25 (m, 1H), 4.38–4.46 (m, 1H), 6.73 (tt, J=7.5, 3.0 Hz, 1H), 6.82 (dt, J=1, 3.4 Hz, 2H), 6.91–6.96 (m, 2H), 7.02 (dt, J=9.1, 2.4 Hz, 2H), 7.11–7.18 (m, 2H) ppm. MS (DCl/$NH_3$) m/z 295 (M+H)$^+$.

Example 18C

N-{4-[(3R)-1-azabicyclo[2.2.2]oct-3-yloxy]phenyl}-N-phenylamine hydrochloride

The product of Example 18B (130 mg, 0.44 mmol) in ethyl acetate (5 mL) was treated with 4M HCl in 1,4-dioxane (0.5 mL, 2 mmol). The title compound was obtained as a solid (70 mg, yield, 48%). $^1$H NMR (MeOH-$d_4$, 300 MHz) δ 1.85–2.20 (m, 3H), 2.30–2.42 (m, 1H), 2.45–2.52 (m, 1H), 3.30–3.45 (m, 5H), 3.70–80(m, 1H), 4.80 (m, 1H), 6.78 (tt, J=7.5, 3.0 Hz, 1H), 6.90 (dt, J=8.8, 3.4 Hz, 2H), 6.94–6.99 (m, 2H), 7.07 (dt, J=8.8, 3.3 Hz, 2H), 7.12–7.20 (m, 2H) ppm. MS (DCl/$NH_3$) m/z 295 (M+H)$^+$. Anal. Calculated for $C_{19}H_{22}N_2O$.2.0HCl.0.8$H_2O$: C, 59.78; H, 6.76; N, 7.34. Found: C, 59.93; H, 6.44; N, 6.85.

Example 19

N-[4-(1-azabicyclo[2.2.2]oct-3-yloxy)phenyl]pyridin-3-amine dihydrochloride

Example 19A

N-[4-(1-azabicyclo[2.2.2]oct-3-yloxy)phenyl]pyridin-3-amine

The product of Example 14B (200 mg, 0.55 mmol) was treated with 3-aminopyridine (Aldrich, 78 mg, 0.83 mmol) according to the procedure of Example 17A. The title compound was purified by chromatography (SiO$_2$, CH$_2$Cl$_2$:MeOH:NH$_3$.H$_2$O, 90:10:2, R$_f$ 0.10) as an oil (110 mg, yield, 68%). $^1$H NMR (MeOH-d$_4$, 300 MHz) δ 1.39–1.53 (m, 1H), 1.58–1.90 (m, 2H), 2.05–2.31 (m, 2H), 2.75–2.98 (m, 5H), 3.25–3.40 (m, 1H), 4.40–4.50 (m, 1H), 6.90 (tt, J=9.1, 3.4 Hz, 1H), 7.09 (dt, J=8.8, 3.4 Hz, 2H), 7.19 (dd, J=8.5, 4.7 Hz, 1H), 7.34 (ddd, J=8.5, 2.7, 1.3 Hz, 1H), 7.87 (dd, J=4.8, 1.4 Hz, 1H), 8.14 (d, J=2.7 Hz, 1H) ppm. MS (DCl/NH$_3$) m/z 296 (M+H)$^+$.

Example 19B

N-[4-(1-azabicyclo[2.2.2]oct-3-yloxy)phenyl]pyridin-3-amine dihydrochloride

The product of Example 19A (110 mg, 0.37 mmol) in ethyl acetate (5 mL) was treated with 4M HCl in 1,4-dioxane (0.5 mL, 2 mmol). The title compound was obtained as a solid (130 mg, yield, 96%). $^1$H NMR (MeOH-d$_4$, 300 MHz) δ 1.85–2.18 (m, 3H), 2.25–2.40 (m, 1H), 2.50–2.58 (m, 1H), 3.30–3.50 (m, 5H), 3.78–3.8(m, 1H), 4.92 (m, 1H), 7.08 (dt, J=8.9, 3.7 Hz, 2H), 7.26 (dt, J=9.2, 3.7 Hz, 2H), 7.78 (dd, J=8.9, 5.5 Hz, 1H), 7.93 (ddd, J=8.8, 2.7, 1.4 Hz, 1H), 8.06 (dt, J=5.4, 1.0 Hz, 1H), 8.17 (d, J=3.1 Hz, 1H) ppm. MS (DCl/NH$_3$) m/z 296 (M+H)$^+$. Anal. Calculated for C$_{18}$H$_{21}$N$_3$O.2.0HCl.1.1H$_2$O: C, 55.70; H, 6.54; N, 10.83. Found: C, 55.55; H, 6.28; N, 11.09.

Example 20

N-[4-(1-azabicyclo[2.2.2]oct-3-yloxy)phenyl]benzamide hydrochloride

Example 20A

N-[4-(1-azabicyclo[2.2.2]oct-3-yloxy)phenyl]benzamide

The product of Example 14B (260 mg, 0.70 mmol) in 1,4-dioxane (Aldrich, anhydrous, 10 mL) was treated with benzamide (Aldrich, 78 mg, 0.83 mmol), Pd$_2$(dba)$_3$ (Strem Chemical, 12.8 mg, 0.014 mmol), Xantphos (Strem Chemicals, 24.3 mg, 0.042 mmol), Cs$_2$CO$_3$ (Aldrich, 456 mg, 1.4 mmol) and heated at 80° C. for 20 hours. The mixture was allowed to cool to room temperature, diluted with ethyl acetate (20 mL), and washed with brine (2×5 mL). The organic phase was concentrated under reduced pressure and the title compound was purified by chromatography (SiO$_2$, CH$_2$Cl$_2$:MeOH:NH$_3$.H$_2$O, 90:10:2, R$_f$ 0.30) as oil (170 mg, yield, 76%). $^1$H NMR (MeOH-d$_4$, 300 MHz) δ 1.45–1.55 (m, 1H), 1.60–1.90 (m, 2H), 2.05–2.30 (m, 2H), 2.75–2.98 (m, 5H), 3.35–3.45 (m, 1H), 4.52–4.58 (m, 1 H), 6.72–6.98 (m, 2H), 7.45–7.62(m, 5H), 7.86–7.96 (m, 2H) ppm. MS (DCl/NH$_3$) m/z 323 (M+H)$^+$.

Example 20B

N-[4-(1-azabicyclo[2.2.2]oct-3-yloxy)phenyl]benzamide hydrochloride

The product of Example 20A (170 mg, 0.53 mmol) in ethyl acetate (5 mL) was treated with 4M HCl in 1,4-dioxane (0.5 mL, 2 mmol). The title compound was obtained as solid (110 mg, yield, 58%). $^1$H NMR (MeOH-d$_4$, 300 MHz) δ 1.85–1.95 (m, 1H), 1.97–2.08 (m, 1H), 2.10–2.18 (m, 1H), 2.25–2.40 (m, 1H), 2.52–2.58 (m, 1H), 3.30–3.50 (m, 5H), 3.78–3.85(m, 1H), 4.92 (m, 1H), 7.00 (d, J=9.1 Hz, 2H), 7.50 (t, J=7.8 Hz, 2H), 7.57 (t, J=7.1 Hz, 1H), 7.63 (d, J=9.0 Hz, 2H), 7.92 (d, J=7.5 Hz, 2H) ppm. MS (DCl/NH$_3$) m/z 323 (M+H)$^+$. Anal. Calculated for C$_{20}$H$_{22}$N$_2$O$_2$.1.0HCl: C, 66.94; H, 6.46; N, 7.81. Found: C, 66.73; H, 6.59; N, 7.64.

Example 21

N-[4-(1-azabicyclo[2.2.2]oct-3-yloxy)phenyl]-N-cyclohexylamine fumarate

Example 21A

3-(4-bromophenoxy)quinuclidine

3-Hydroxy quinuclidine (Aldrich, 1.27 g, 10 mmol) was treated with 4-bromo-iodobenzene (Aldrich, 2.82 g, 10 mmol) according to the procedure of Example 14A. The title compound was purified by chromatography (SiO$_2$, CH$_2$Cl$_2$:MeOH:NH$_3$.H$_2$O, 90:10:1, R$_f$ 0.20) as oil (0.85 g, yield, 30%). $^1$H NMR (MeOH-d$_4$, 300 MHz) δ 1.40–1.56 (m, 1H), 1.64–1.80 (m, 2H), 1.90–2.08 (m, 1H), 2.10–2.21 (m, 1H), 2.60–3.00 (m, 5H), 3.34–3.40 (m, 1H), 4.46 (m, 1H), 6.83 (d, J=9.5 Hz, 2H) 7.37 (d, J=9.2, Hz, 2H), ppm. MS (DCl/NH$_3$) m/z 282 (M+H)$^+$, 284 (M+H)$^+$.

Example 21 B

N-[4-(1-azabicyclo[2.2.2]oct-3-yloxy)phenyl]-N-cyclohexylamine

The product of Example 21A (281 mg, 1.0 mmol) was treated with cyclohexylamine (Aldrich, 150 mg, 1.5 mmol) according to the procedure of Example 17A. The title compound was purified by chromatography (SiO$_2$, CH$_2$Cl$_2$:MeOH:NH$_3$.H$_2$O, 90:10:2, R$_f$ 0.10) as oil (130 mg, yield, 43%). $^1$H NMR (MeOH-d$_4$, 300 MHz) δ 1.06–1.45 (m, 6H), 1.60–1.90 (m, 5H), 1.93–2.05 (m, 3H), 2.18–2.37 (m, 2H), 3.05–3.28 (m, 5H), 4.30–4.40 (m, 1H), 6.65 (d, J=8.8 Hz, 2H), 6.74 (d, J=9.2 Hz, 2H) ppm. MS (DCl/NH$_3$) m/z 301 (M+H)$^+$.

Example 21C

N-[4-(1-azabicyclo[2.2.2]oct-3-yloxy)phenyl]-N-cyclohexylamine fumarate

The product of Example 21B (130 mg, 0.43 mmol) in EtOAc/MeOH (v.10/1 1, 5 mL) was treated with fumaric acid (50 mg, 0.43 mmol) at room temperature overnight. The title compound was obtained as a solid (121 mg, yield, 75%). $^1$H NMR (MeOH-d$_4$, 300 MHz) δ 1.06–1.45 (m, 6H), 1.61–1.90 (m, 5H), 1.93–2.05 (m, 3H), 2.18–2.37 (m, 2H), 3.05–3.28 (m, 5H), 3.46–3.60 (m, 1H), 4.52–4.58 (m, 1H), 6.65 (d, J=8.8 Hz, 2H), 6.69 (s, 1H), 6.78 (d, J=9.2 Hz, 2H)

ppm. MS (DCl/NH$_3$) m/z 301 (M+H)$^+$. Anal. Calculated for C$_{19}$H$_{28}$N$_2$O.0.6C$_4$H$_4$O$_4$: C, 69.45; H 8.28; N, 7.57. Found: C, 69.53; H, 8.48; N, 7.47.

Example 22

N-[4-(1-azabicyclo[2.2.2]oct-3-yloxy)phenyl]-N, N-dithien-3-ylamine fumarate

Example 22A 3-(4-nitrophenoxy)quinuclidine

3-Hydroxy quinuclidine (Aldrich, 2.54 g, 10 mmol) was treated with 1-iodo-4-nitro-benzene (5 g, 20 mmol) according to the procedure of Example 14A. The title compound was purified by chromatography (SiO$_2$, CH$_2$Cl$_2$:MeOH: NH$_3$.H$_2$O, 90:10:1, R$_f$ 0.20) (1.02 g, yield, 21%). $^1$H NMR (MeOH-d$_4$, 300 MHz) δ 1.40–1.56 (m, 1H), 1.65–1.90 (m, 2H), 1.90–2.08 (m, 1H), 2.15–2.25 (m, 1H), 2.75–3.00 (m, 5H), 3.34–3.40 (m, 1H), 4.69 (m, 1H), 7.07 (d, J=9.5 Hz, 2H), 8.21 (d, J=9.2, Hz, 2H) ppm. MS (DCl/NH$_3$) m/z 249 (M+H)$^+$.

Example 22B 4-(1-azabicyclo[2.2.2]oct-3-yloxy)aniline

The product of Example 22A (1.02 g, 4.1 mmol) in MeOH (25 mL) was treated with Pd/C (Aldrich, 10%, 150 mg) under H$_2$ at room temperature for 1.5 hours. The mixture was filtered through a short column of diatomaceous earth and the filtrate was concentrated under reduced pressure to provide the title compound (0.92 g, yield, 100%). $^1$H NMR (MeOH-d$_4$, 300 MHz) δ 1.40–1.56 (m, 1H), 1.65–1.90 (m, 2H), 1.96–2.13 (m, 2H), 2.70–3.00 (m, 5H), 3.10–3.20 (m, 1H), 4.35 (m, 1H), 6.65–6.78 (m, 4H) ppm. MS (DCl/NH$_3$) m/z 219 (M+1)$^+$.

Example 22C

N-[4-(1-azabicyclo[2.2.21]oct-3-yloxy)phenyl]-N,N-dithien-3-ylamine

The product of Example 22B (219 mg, 1.0 mmol) in toluene (5 mL) was treated with 3-bromothiophene (Aldrich, 178 mg, 1.1 mmol), Pd$_2$(dba)$_3$ (Strem Chemicals, 24 mg, 0.025 mmol), ($^t$Bu$_3$P)$_2$ Pd (Strem Chemicals, 26 mg, 0.05 mmol), sodium tert-butoxide (Aldrich, 105 mg, 1.1 mmol) and heated at 110° C. under N$_2$ for 15 hours. The mixture was diluted with ethyl acetate (20 mL) and washed with water (2×5 mL). The organic phase was concentrated and the title compound was purified by preparative HPLC (Gilson, column, Symmetry® C-8 7 μm, 40×100 mm. Solvent, acetonitrile/H$_2$O (with 0.2% v. TFA) (v. 90/10 to 10/90 over 20 min.) Flow rate, 75 mL/min. uv, 250 nM) as an oil (102 mg, yield, 27%). $^1$H NMR (MeOH-d$_4$, 300 MHz) δ 1.40–1.50 (m, 1H), 1.60–1.85 (m, 2H), 2.00–2.19 (m, 2H), 2.71–3.00 (m, 5H), 3.25–3.34 (m, 1H), 4.40–4.50 (m, 1H), 6.54 (dd, J=3.4, 1.4 Hz, 2H), 6.80 (dd, J=1.7, 5.1 Hz, 2H), 6.86 (d, J=9.2 Hz, 2H), 7.03 (d, J=9.2 Hz, 2H), 7.29 (dd, J=3.1, 5.4 Hz 2H) ppm. MS (DCl/NH$_3$) m/z 383 (M+H)$^+$.

Example 22D

N-[4-(1-azabicyclo[2.2.2]oct-3-yloxy)phenyl]-N,N-dithien-3-ylamine fumarate

The product of Example 22C (102 mg, 0.27 mmol) in ethyl acetate:MeOH (5 mL, 10:1) was treated with fumaric acid (35 mg, 0.30 mmol) at room temperature overnight. The title compound was obtained as a solid (125 mg, yield, 89%). $^1$H NMR (MeOH-d$_4$, 300 MHz) δ 1.75–2.02 (m, 2H), 2.08–2.37 (m, 2H), 2.45–2.55 (m, 1H), 3.19–3.42 (m, 5H), 3.70–3.80 (m, 1H), 4.80 (m, 1H), 6.58 (dd, J=3.1, 1.4 Hz, 2H), 6.69 (s, 2.5H), 6.80 (dd, J=5.4, 1.4 Hz, 2H), 6.93 (d, J=8.8 Hz, 2H), 7.06 (d, J=9.2 Hz, 2H), 7.82 (dd, J=5.1, 3.1 Hz, 2H) ppm. MS (DCl/NH$_3$) m/z 383 (M+H)$^+$. Anal. Calculated. for C$_{21}$H$_{22}$N$_2$OS$_2$.1.25C$_4$H$_4$O$_4$ C, 59.19; H 5.16; N, 5.31. Found: 59.14; H, 4.91; N, 5.25.

Example 23

N-[4-(1-azabicyclo[2.2.2]oct-3-yloxy)phenyl]-N-1, 3-thiazol-2-yl-1,3-thiazol-2-amine dihydrochloride

Example 23A

N-[4-(1-azabicyclo[2.2.2]oct-3-yloxy)phenyl]-N-1, 3-thiazol-2-yl-1,3-thiazol-2-amine The product of Example 22B (219 mg, 1.0 mmol) was treated with 2-bromothiazole (Aldrich, 179 mg, 1.1 mmol) according to the procedure of Example 22C. The title compound was purified by preparative HPLC as an oil (42 mg, yield, 11%). $^1$H NMR (MeOH-d$_4$, 300 MHz) δ 1.45–1.54 (m, 1H), 1.65–1.88 (m, 2H), 2.00–225 (m, 2H), 2.75–3.03 (m, 5H), 3.35–3.42 (m, 1H), 4.60–4.66 (m, 1H), 7.02–7.06 (m, 2H), 7.10–7.17 (m, 2H), 7.33–7.39 (m, 4H) ppm. MS (DCl/NH$_3$) m/z 385 (M+H)$^+$.

Example 23B

N-[4-(1-azabicyclo[2.2.2]oct-3-yloxy)phenyl]-N-1, 3-thiazol-2-yl-1,3-thiazol-2-amine dihydrochloride The product of Example 23A (42 mg, 0.11 mmol) in ethyl acetate (3 mL) was treated with 4M HCl in 1,4-dioxane (0.2 mL, 0.8 mmol) at ambient temperature for 10 hours. The title compound was obtained as a solid (22 mg, yield, 40%). $^1$H NMR (MeOH-d$_4$, 300 MHz) δ 1.87–2.23(m, 3H), 2.30–2.40 (m, 1H), 2.55–2.64 (m, 1H 3.30–3.50 (m, 5H), 3.85–3.92 (m, 1H), 5.05 (m, 1H), 7.23 (d, J=4.1 Hz, 2H), 7.30 (d, J=8.8 Hz, 2H), 7.52 (d, J=3.7Hz, 2H), 7.60 (d, J=8.8 Hz, 2H) ppm. MS (DCl/NH$_3$) m/z 385 (M+H)$^+$. Anal. Calculated for C$_{19}$H$_{20}$N$_4$OS$_2$.2HCl.2H$_2$O: C, 46.25; H 5.31; N, 11.35. Found: C, 46.41; H, 5.06; N, 11.09.

Example 24

N-[4-(1-azabicyclo[2.2.2]oct-3-yloxy)phenyl]-N,N-bis(1-benzothien-3-yl)amine hydrochloride

Example 24A

N-[4-(1-azabicyclo[2.2.2]oct-3-yloxy)phenyl]-N,N-bis(1-benzothien-3-yl)amine

The product of Example 22B (219 mg, 1.0 mmol) was treated with 3-bromo-1-benzothiophene (Aldrich, 233 mg, 1.1 mmol) according to the procedure of Example 21C. The title compound was purified by preparative HPLC as an oil (70 mg, yield, 14%). $^1$H NMR (MeOH-d$_4$, 300 MHz) δ 1.40–1.75 (m, 3H), 1.90–2.05 (m, 2H), 2.64–296 (m, 5H), 3.10–3.20 (m, 1H), 4.20–4.28 (m, 1H), 6.57 (s, 4H), 7.23–7.42 (m, 4H), 7.58–7.68 (m, 2H), 7.81–7.98 (m, 4H) ppm. MS (DCl/NH$_3$) m/z 483 (M+1)$^+$.

Example 24B

N-[4-(1-azabicyclo[2.2.2]oct-3-yloxy)phenyl]-N,N-bis(1-benzothien-3-yl)amine hydrochloride The product of Example 24A (70 mg, 0.14 mmol) in ethyl acetate (3 mL) was treated with 4M HCl in 1,4-dioxane (0.2 mL, 0.8 mmol) at ambient temperature for 10 hours. The title compound was obtained as a solid (42 mg, yield, 53%). $^1$H NMR (MeOH-$d_4$, 300 MHz) δ 1.85–2.25(m, 3H), 2.30–2.40 (m, 1H), 3.17–3.44 (m, 6H), 3.60–3.68 (m, 1H), 4.61 (m, 1H), 6.56–6.68 (m, 4H), 7.26–7.44 (m, 5H), 7.61–7.67 (m, 2H), 7.84–7.97 (m, 3H) ppm. MS (DCl/NH$_3$) m/z 483 (M+H)$^+$. Anal. Calculated for $C_{29}H_{26}N_2OS_2 \cdot HCl \cdot 1.5H_2O$: C, 63.78; H 5.54; N, 5.13. Found: C, 63.76; H, 5.65; 4.84.

Example 25

1-(5-{[4-(1-azabicyclo[2.2.2]oct-3-yloxy)phenyl]amino}thien-2-yl)ethanone hydrochloride

Example 25A 1-(5-{[4-(1-azabicyclo[2.2.2]oct-3-yloxy)phenyl]amino}thien-2-yl)ethanone The product of Example 22B (219 mg, 1.0 mmol) was treated with 1-(5-bromothien-2-yl)ethanone (Aldrich, 227 mg, 1.1 mmol) according to the procedure of Example 22C. The title compound was purified by preparative HPLC as an oil (40 mg, yield, 12%). $^1$H NMR (MeOH-$d_4$, 300 MHz) δ 1.45–1.84 (m, 3H), 2.00–2.18 (m, 2H), 2.40 (s, 3H), 2.75–2.98 (m, 5H), 3.25–3.32 (m, 1H), 4.49 (m, 1H), 6.36 (d, J=4.4 Hz, 1H), 6.92 (d, J=8.8 Hz, 2H), 7.20 (d, J=8.8 Hz, 2H), 7.63 (d, J=4.4 Hz, 1H) ppm. MS (DCl/NH$_3$) m/z 343 (M+H)$^+$.

Example 25B 1-(5-{[4-(1-azabicyclo[2.2.2]oct-3-yloxy)phenyl]amino}thien-2-yl)ethanone hydrochloride The product of Example 25A (40 mg, 0.12 mmol) was treated with HCl (Aldrich, in dioxane, 4M, 0.2 mL, 0.8 mmol) in ethyl acetate (3 mL) at ambient temperature for 10 h. The title compound was obtained as solid (37 mg, yield, 64%). $^1$H NMR (MeOH-$d_4$, 300 MHz) δ 1.82–2.19(m, 3H), 2.30–2.38 (m, 1H), 2.41 (s, 3H), 2.46–2.55 (m, 1H), 3.23–3.47 (m, 5H), 3.76–3.84 (m, 1H), 4.78–4.85 (m, 1H), 6.40 (d, J=4.4 Hz, 1H), 7.00 (d, J=8.8 Hz, 2H), 7.25 (d, J=8.8 Hz, 2H), 7.65 (d, J=4.4 Hz, 1H) ppm. MS (DCl/NH$_3$) m/z 343 (M+H)$^+$.

Example 26

N-[4-(1-azabicyclo[2.2.2]oct-3-yloxy)phenyl]-N-(4-methylthien-3-yl)amine hydrochloride

Example 26A

N-[4-(1-azabicyclo[2.2.2]oct-3-yloxy)phenyl]-N-(4-methylthien-3-yl)amine

The product of Example 22B (219 mg, 1.0 mmol) was treated with 3-bromo-4-methylthiophene (Aldrich, 196 mg, 1.1 mmol) according to the procedure of Example 22C. The title compound was purified by preparative HPLC as an oil (180 mg, yield, 57%). $^1$H NMR (MeOH-$d_4$, 300 MHz) δ 1.45–1.84 (m, 3H), 1.97–2.15 (m, 2H), 2.70–300 (m, 5H), 3.25–3.32 (m, 1H), 4.39 (m, 1H), 6.60 (d, J=3.4 Hz, 1H), 6.75–6.83 (m, 2H), 6.87–6.96 (m, 3H) ppm. MS (DCl/NH$_3$) m/z 315 (M+H)$^+$.

Example 26B

N-[4-(1-azabicyclo[2.2.2]oct-3-yloxy)phenyl]-N-(4-methylthien-3-yl)amine hydrochloride The product of Example 26A (198 mg, 0.57 mmol) in ethyl acetate (5 mL) was treated with 4M HCl in 1,4-dioxane (0.5 mL, 2 mmol) at ambient temperature for 10 hours. The title compound was obtained as a solid (155 mg, yield, 77%). $^1$H NMR (MeOH-$d_4$, 300 MHz) δ 1.80–2.02(m, 2H), 2.03–2.16 (m, 4H), 2.30–2.38 (m, 1H), 2.46–2.55 (m, 1H), 3.20–3.47 (m, 5H), 3.72–3.80 (m, 1H), 4.68–4.75 (m, 1H), 6.66 (d, J=3.4 Hz, 1H), 6.83–6.99 (m, 5H) ppm. MS (DCl/NH$_3$) m/z 315 (M+H)$^+$. Anal. Calculated for $C_{18}H_{22}N_2OS \cdot 1.05HCl$ C, 61.29; H 6.59; N, 7.94. Found: C, 61.25; H, 6.50; N, 7.82.

Example 27

3-[(6-phenoxypyridazin-3-yl)oxy]quinuclidine hydrochloride

Example 27A 3-chloro-6-phenoxypyridazine 3,6-Dichloropyridazine (Aldrich, 4.47 g, 30 mmol) in NaOH (10%, 20 mL) was treated with phenol (Aldrich, 1.88 g, 20 mmol) at 100° C. for 15 hours. After cooling to room temperature, the mixture was extracted with ethyl acetate (2×50 mL). The extracts were combined and concentrated under reduced pressure. The title compound was purified by chromatography (SiO$_2$, Hexanes: ethyl acetate=80: 20, $R_f$ 0.5) as a solid (3.8 g, yield, 92%). $^1$H NMR (CDCl$_3$, 300 MHz) δ 7.11–7.29 (m, 3H), 7.38–7.55 (m, 4H) ppm. MS (DCl/NH$_3$) m/z 207 (M+H)$^+$, 209 (M+H)$^+$.

Example 27B 3,6-diphenoxypyridazine

Phenol (Aldrich, 1.88 g, 20 mmol) in tetrahydrofuran (50 mL) was treated with potassium tert-butoxide (Aldrich, 2.24 g, 20 mmol) at ambient temperature for 10 minutes. The product of Example 27A (3.0 g, 14.5 mmol) was then added and the reaction mixture was stirred at 60° C. for 10 hours. The mixture was allowed to cool to room temperature, diluted with ethyl acetate (100 mL), and washed with brine (2×10 mL). The organic phase was concentrated affording the title compound as a solid (3.2 g, yield, 84%). $^1$H NMR (MeOH-$d_4$, 300 MHz) δ 7.14–7.28 (m, 6H), 7.38–7.48 (m, 6H) ppm. MS (DCl/NH$_3$) m/z 265(M+H)$^+$.

Example 27C

3-[(6-phenoxypyridazin-3-yl)oxy]quinuclidine

3-Hydroxy quinuclidine (Aldrich, 160 mg, 1.25 mmol) in tetrahydrofuran was treated with potassium tert-butoxide (112 mg, 1.0 mmol) at ambient temperature for 10 minutes. The product of Example 27B (528 mg, 2 mmol) was added.

The mixture was stirred at ambient temperature for 6 hours. The mixture was diluted with ethyl acetate (20 mL) and washed with brine (2×5 mL). The organic phase was concentrated and the title compound was purified by chromatography (SiO$_2$, CH$_2$Cl$_2$:MeOH:NH$_3$.H$_2$O, 90:10:2, R$_f$ 0.20) as oil (120 mg, yield, 45%). $^1$H NMR (MeO H-d$_4$300 MHz) δ 1.48–1.58 (m, 1H), 1.60–1.90 (m, 2H), 1.96–2.10 (m, 1H), 2.24–2.30 (m, 1H), 2.77–2.98 (m, 5H), 3.40–3.50 (m, 1H), 5.10–5.20 (m, 1H), 7.11–7.16 (m, 2H), 7.20–7.26 (m, 1H), 7.25(d, J=9.5 Hz, 1H), 7.30 (d, J=9.5 Hz, 1H), 7.38–7.45 (m, 2H) ppm. MS (DCl/NH$_3$) m/z 265 (M+H)$^+$.

Example 27D

3-[(6-phenoxypyridazin-3-yl)oxy]quinuclidine hydrochloride

The product of Example 27C (120 mg, 0.45 mmol) in ethyl acetate (5 mL) was treated with 4M HCl in 1,4-dioxane (0.5 mL, 2 mmol). The title compound was obtained as a solid (120 mg, yield, 80%). $^1$H NMR (MeOH-d$_4$, 300 MHz) δ 1.85–2.18 (m, 1H), 2.30–2.45 (m, 1H), 2.56–2.64 (m, 1H), 3.35–3.50 (m, 5H), 3.85–3.9(m, 1H), 5.45 (m, 1H), 7.18–7.26 (m, 2H), 7.28–7.36 (m, 1H), 7.45–7.51 (m, 2H), 7.52 (s, 2H) ppm. MS (DCl/NH$_3$) m/z 265 (M+H)$^+$. Anal. Calculated for C$_{20}$H$_{22}$N$_2$O$_2$.2.0HCl: C, 55.14; H, 5.72; N, 11.35. Found: C, 55.03; H, 5.59; N, 11.64.

Example 28

3-[(5-phenoxypyridin-2-yl)oxy]quinuclidine hydrochloride

Example 28A

3-[(5-phenoxypyridin-2-yl)oxy]quinuclidine

3-Hydroxy quinuclidine (Aldrich, 3.2 g, 25 mmol)) in DMF (anhydrous, 30 mL) was treated with NaH (Aldrich, 99%, 1.2 g, 50 mmol) at ambient temperature for 1 hour. 2-Chloro-5-bromopyridine (7.1 g, 30 mmol) was added and the mixture was stirred at 100° C. for 6 hours. The mixture was allowed to cool to room temperature, treated with Na$_2$CO$_3$ (2M, 10 mL) at 10° C., and extracted with ethyl acetate (2×50 mL). The extracts were combined and concentrated under reduced pressure. The title compound was purified by chromatography (SiO$_2$, CH$_2$Cl$_2$:MeOH:NH$_3$.H$_2$O, 90:10:2, R$_f$ 0.20) as oil (5.3 g, yield, 75%). $^1$H NMR (MeOH-d$_4$, 300 MHz) δ 1.46–1.58 (m, 1H), 1.60–1.88 (m, 2H), 1.96–2.10 (m, 1H), 2.24–2.30 (m, 1H), 2.72–2.98 (m, 5H), 3.42–3.46 (m, 1H), 5.00–5.08 (m, 1H), 6.75 (d, J=8.8 Hz, 1H), 7.77 (dd, J=8.9, 2.4 Hz, 1H), 8.16 (d, J=2.7, 1H) ppm. MS (DCl/NH$_3$) m/z 283 (M+H)$^+$, 285 (M+H)$^+$ Example 28B 3-[(5-phenoxypyridin-2-yl)oxy]quinuclidine The product of Example 28A (283 mg, 1 mmol) was treated with phenol (Aldrich, 188 mg, 2 mmol) according the procedure of Example 14C. The title compound was purified by chromatography (SiO$_2$, CH$_2$Cl$_2$:MeOH:NH$_3$.H$_2$O, 90:10:2, R$_f$ 0.10) as an oil (210 mg, yield, 71%). $^1$H NMR (MeOH-d$_4$, 300 MHz) δ 1.46–1.58 (m, 1H), 1.60–1.88 (m, 2H), 1.96–2.10 (m, 1H), 2.24–2.30 (m, 1H), 2.75–3.02 (m, 5H), 3.46–3.50 (m, 1H), 5.10–5.15 (m, 1H), 6.75–6.84 (m, 2H), 6.90–7.00 (m, 2H), 7.25–7.42 (m, 2H), 7.78 (dd, J=8.8, 2.3 Hz, 1H), 7.86 (d, J=3.0 Hz, 1H) ppm. MS (DCl/NH$_3$) m/z 297 (M+H)$^+$.

Example 28C

3-[(5-phenoxypyridin-2-yl)oxy]quinuclidine hydrochloride

The product of Example 28B (210 mg, 0.71 mmol) in ethyl acetate (5 mL) was treated with 4M HCl in 1,4-dioxane (0.5 mL, 2 mmol). The title compound was obtained as a solid (120 mg, yield, 80%). $^1$H NMR (MeOH-d$_4$, 300 MHz) δ 1.85–2.20 (m, 3H), 2.30–2.45 (m, 1H), 2.56–2.64 (m, 1H), 3.35–3.50 (m, 5H), 3.80–3.9(m, 1H), 5.35 (m, 1H), 6.88–7.00 (m, 3H), 7.06–7.14 (m, 1H), 7.30–7.38 (m, 2H), 7.45 (dd, J=8.8, 3.0 Hz, 1H), 7.88 (d, J=2.3 Hz, 1H) ppm. MS (DCl/NH$_3$) m/z 297 (M+H)$^+$. Anal. Calculated for C$_{20}$H$_{20}$N$_2$O$_2$.1.0HCl.0.3H$_2$O: C, 63.92; H, 6.44; N, 8.28. Found: 63.97; H, 6.49; N, 8.17.

Example 29

3-[(5-phenoxypyrimidin-2-yl)oxy]quinuclidine fumarate

Example 29A

3-[(5-bromopyrimidin-2-yl)oxy]quinuclidine

3-Hydroxy quinuclidine (Aldrich, 254 mg, 2 mmol) in tetrahydrofuran (10 ml) was treated with potassium tert-butoxide (Aldrich, 224 mg, 2 mmol) at ambient temperature for 1 hour. The mixture was treated with 2-iodo-5-bromopyrimidine (TCI, 568 mg, 2 mmol), stirred at room temperature for 1 hour, treated with water (5 mL), and extracted with chloroform:isopropyl alcohol (10:1) (3×20 mL). The extracts were combined and concentrated. The title compound was purified by chromatography (SiO$_2$, CH$_2$Cl$_2$:MeOH: NH$_3$H$_2$O, 90:10:2, R$_f$ 0.20) as oil (210 mg, yield, 71%). $^1$H NMR (MeOH-d$_4$, 300 MHz) δ 1.56–1.68 (m, 1H), 1.70–1.90 (m, 2H), 2.05–2.30 (m, 2H), 2.79–3.06 (m, 5H), 3.40–3.48 (m, 1H), 5.11 (m, 1H), 8.64 (s, 2h) ppm. MS (DCl/NH$_3$) m/z 284 (M+H)$^+$, 286 (M+H)$^+$.

Example 29B

3-[(5-phenoxypyrimidin-2-yl)oxy]quinuclidine fumarate

The product of Example 29A (284 mg, 1.0 mmol) was treated with phenol (Aldrich, 188 mg, 2 mmol) according to the procedure of Example 14C. The free base of the title compound was purified by chromatography (SiO$_2$, CH$_2$Cl$_2$:MeOH:NH$_3$H$_2$O, 90:10:2, R$_f$ 0.15) as an oil (42 mg, yield, 14%). The free base of the title compound (42 mg, 0.14 mmol) in ethyl acetate:MeOH (3 mL, 10:1) was treated with fumaric acid (18 mg, 0.15 mmol) at room temperature for 10 hours. The title compound was obtained as a solid (22 mg, 36%). $^1$H NMR (MeOH-d$_4$, 300 MHz) δ 1.84–2.18 (m, 3H), 2.25–2.38 (m, 1H), 2.50–2.58 (m, 1H), 3.23–3.44 (m, 5H), 3.80–3.88 (m, 1H), 5.32 (m, 1H), 6.69 (s, 2.5H), 7.00–7.06 (m, 2H), 7.15–7.20 (m, 2H), 8.39 (s, 2H) ppm. MS (DCl/NH$_3$) m/z 298 (M+H)$^+$. Anal. Calculated for C$_{17}$H$_{19}$N$_3$O$_2$.1.26C$_4$H$_4$O$_4$: C, 59.67; H 5.46; N, 9.47. Found: C, 59.43; N, 9.51.

Example 30

N-(4-phenoxyphenyl)quinuclidin-3-amine dihydrochloride

Example 30A

N-(4-phenoxyphenyl)quinuclidin-3-amine

3-Quinuclidinone hydrochloride (Aldrich, 1.61 g, 10 mmol) in acetic acid (25 mL) was treated with 4-phenoxyaniline (Aldrich, 0.93 g, 5.0 mmol), Na$_2$SO$_4$ (anhydrous, Aldrich, 7.40 g, 50 mmol) and NaBH(OAc)$_3$ (Aldrich, 3.16 g, 15 mmol) at ambient temperature for 15 hours. The reaction mixture was slowly poured into a flask containing 75 mL of saturated NaHCO$_3$, stirred for 20 minutes, and extracted with ethyl acetate (3×100 mL). The extracts were combined and washed with brine (2×20 mL). The organic phase was concentrated under reduced pressure and the title compound was purified by chromatography (SiO$_2$, CH$_2$Cl$_2$:MeOH:NH$_3$.H$_2$O, 90:10:2, R$_f$, 0.10) as a solid (1.46 g, yield, 99%). $^1$H NMR (MeOH-d$_4$, 300 MHz) δ 1.78–1.90 (m, 1H), 2.00–2.10 (m, 2H), 2.22–2.35 (m, 2H), 3.05 (ddd, J=12.9, 4.7, 2.0 Hz, 1H) 3.20–3.40 (m, 4H), 3.78 (ddd, J=12.9, 9.5, 2.4 Hz, 1H), 3.90–3.98 (m, 1H), 6.65–6.75 (m, 2H), 6.80–6.90 (m, 4H), 6.99 (tt, J=7.5, 1.0 Hz, 1H), 7.20–7.29 (m, 2H) ppm. MS (DCl/NH$_3$) m/z 295 (M+H)$^+$.

Example 30B

N-(4-phenoxyphenyl)quinuclidin-3-amine dihydrochloride

The product of Example 30A (1.46 g, 4.9 mmol) in ethyl acetate (20 mL) was treated with 4M HCl in 1,4-dioxane (5 mL, 20 mmol). The title compound was obtained as a solid (1.40 g, yield, 77%). $^1$H NMR (MeOH-d$_4$, 300 MHz) δ 1.90–2.00 (m, 1H), 2.05–2.15 (m, 2H), 2.35–2.45 (m, 2H), 3.15 (ddd, J=12.9, 5.1, 2.4 Hz, 1H) 3.30–3.50 (m, 4H), 3.80 (ddd, J=12.9, 9.5, 2.7 Hz, 1H), 3.95–4.10 (m, 1H), 6.85–7.00 (m, 6H), 7.04 (tt, J=8.4, 1.0 Hz, 1H), 7.26–7.32 (m, 2H) ppm. MS (DCl/NH$_3$) m/z 295 (M+H)$^+$. Anal. Calculated for C$_{19}$H$_{22}$N$_2$O.2.0HCl: C, 62.13; H, 6.59; N, 7.63. Found: C, 62.01; H, 6.53; N, 7.49.

Example 31

N-[4-(4-chlorophenoxy)phenyl]quinuclidin-3-amine hydrochloride

3-Quinuclidinone hydrochloride (Aldrich, 1.61 g, 10 mmol) was treated with 4-(4-chlorophenyloxy) aniline (Aldrich, 1.10 g, 5.0 mmol) according to the procedure of Example 30A. The free base of the title compound was purified by chromatography (SiO$_2$, CH$_2$Cl$_2$:MeOH:NH$_3$.H$_2$O, 90:10:2, R$_f$, 0.10) as a solid (1.52 g, yield, 93%). MS (DCl/NH$_3$) m/z 329 (M+H)$^+$, 331 (M+H)$^+$. The free base (200 mg, 0.61 mmol) was treated with 4M HCl 1,4-dioxane (0.5 mL, 2.0 mmol) in ethyl acetate (5 mL). The hydrochloride salt of the title compound was obtained as a solid (195 mg, yield, 80%). $^1$H NMR (MeOH-d$_4$, 300 MHz) δ 1.90–2.18 (m, 3H), 2.35–2.45 (m, 2H), 3.24 (ddd, J=12.5, 5.4, 2.3 Hz, 1H) 3.30–3.50 (m, 4H), 3.82 (ddd, J=12.2, 9.8, 2.7 Hz, 1H), 3.95–4.10 (m, 1H), 6.91 (dt, J=9.1, 2.3 Hz, 2H), 6.95–7.02 (m, 4H), 7.30(dt, J=9.2, 2.4 Hz, 2H), 7.26–7.32 (m, 2H) ppm. MS (DCl/NH$_3$) m/z 329 (M+H)$^+$, 331 (M+H)$^+$. Anal Calculated for C$_{19}$H$_{21}$ClN$_2$O.2.0HCl.0.5H$_2$O: C, 55.56; H, 5.89; N, 6.82. Found: C, 55.78; H, 5.28; N, 6.62.

Example 32

N-[4-(4-methylphenoxy)phenyl]quinuclidin-3-amine hydrochloride

Example 32A

N-[4-(4-methylphenoxy)phenyl]quinuclidin-3-amine

3-Quinuclidinone hydrochloride (Aldrich, 1.61 g, 10 mmol) was treated with 4-(4-methylphenoxy)aniline (0.99 g, 5.0 mmol) according to the procedure of Example 30A. The title product was purified by chromatography (SiO$_2$, CH$_2$Cl$_2$:MeOH:NH$_3$.H$_2$O, 90:10:1, R$_f$, 0.10) as an oil (1.48 g, yield, 95%). $^1$H NMR (MeOH-d$_4$, 300 MHz) δ 1.55–1.70 (m, 1H), 1.78–1.95 (m, 2H), 2.00–2.15 (m, 2H), 2.28 (s, 3H), 2.71 (ddd, J=12.9, 5.1, 2.2 Hz, 1H), 2.95–3.10 (m, 4H), 3.46 (ddd, J=12.9, 9.5, 2.4 Hz, 1H), 3.60–3.70 (m, 1H), 6.64 (dt, J=9.0, 2.7 Hz, 2H), 6.72–6.84 (m, 4H), 7.06 (dt, J=9.1, 2.8 Hz, 2H) ppm. MS (DCl/NH$_3$) m/z 309 (M+H)$^+$.

Example 32B

N-[4-(4-methylphenoxy)phenyl]quinuclidin-3-amine hydrochloride

The product of Example 32A (200 mg, 0.65 mmol) in ethyl acetate (5 mL) was treated with 4M HCl in dioxane (0.5 mL). The title compound was obtained as a solid (180 mg, yield, 73%). $^1$H NMR (MeOH-d$_4$, 300 MHz) δ 1.96–2.17 (m, 3H), 2.31 (s, 3H), 2.34–2.41 (m, 2H), 3.26–3.54 (m, 5H), 3.81 (ddd, J=12.9, 9.5, 2.4 Hz, 1H), 4.06–4.13 (m, 1H), 6.85 (dt, J=9.0, 2.7 Hz, 2H), 6.97 (dt, J=9.1, 2.7 Hz, 2H) 7.09–7.17 (m, 4H), ppm. MS (DCl/NH$_3$) m/z 309 (M+H)$^+$. Anal. calculated for C$_{20}$H$_{24}$N$_2$O.2.0HCl.1.0H$_2$O: C, 60.15; H, 7.07; N, 7.01. Found: C, 60.34; H, 7.14; N, 6.98.

Example 33

N-[4-(4-aminophenoxy)phenyl]quinuclidin-3-amine

Example 33A

N-[4-(4-aminophenoxy)phenyl]guinuclidin-3-amine

3-Quinuclidinone hydrochloride (Aldrich, 1.61 g, 10 mmol) was treated with 4-(4-aminophenoxy)phenylamine (1.00 g, 5.0 mmol) according to the procedure of Example 30A. The title product was purified by chromatography (SiO$_2$, CH$_2$Cl$_2$:MeOH:NH$_3$.H$_2$O, 80:20:4, R$_f$, 0.20) as an oil (0.98 g, yield, 63%). $^1$H NMR (MeOH-d$_4$, 300 MHz) 61.55–1.70 (m, 1H), 1.80–1.95 (m, 2H), 1.98–2.15 (m, 2H), 2.68 (ddd, J=12.9, 5.1, 2.7 Hz, 1H), 2.88–3.11 (m, 4H), 3.42 (ddd, J=12.9, 9.5, 2.4 Hz, 1H), 3.59–3.65 (m, 1H), 6.58–6.84 (m, 8H) ppm. MS (DCl/NH$_3$) m/z 310 (M+H)$^+$.

Example 33B

N-[4-(4-aminophenoxy)phenyl]quinuclidin-3-amine hydrochloride

The product of Example 33A (150 mg, 0.48 mmol) in ethyl acetate (5 mL) was treated with 4M HCl in 1,4-dioxane (0.5 mL). The title compound was obtained as a solid (150 mg, yield, 82%). $^1$H NMR (MeOH-d$_4$, 300 MHz) δ 1.96–2.17 (m, 3H), 2.30–2.30–2.41 (m, 2H), 3.16 (ddd, J=12.9, 5.1, 2.5 Hz, 1H), 3.27–3.47 (m, 4H), 3.81 (ddd, J=12.9, 9.5, 2.4 Hz, 1H), 4.00–4.10 (m, 1H), 6.89 (dt, J=9.0, 2.7 Hz, 2H), 6.96 (dt, J=9.1, 2.7 Hz, 2H) 7.04 (dt, J=9.0, 2.8 Hz, 2H), 7.34 (dt, J=9.0, 3.0 Hz, 2H) ppm. MS (DCl/NH$_3$) m/z 310 (M+H)$^+$. Anal. calculated for C$_{19}$H$_{23}$N$_3$O.3.0HCl.0.9 H$_2$O: C, 52.46; H, 6.44; N, 9.66. Found: C, 52.77; H, 6.91; N, 9.76.

Example 34

4,4'-di(1-aza-bicyclo[2.2.2]oct-3-yl-amino)-diphenyl thioether tetra (hydrochloride)

Example 34A 4,4'-di(1-aza-bicyclo[2.2.2]oct-3-yl-amino)-diphenyl thioether

3-Quinuclidinone hydrochloride (Aldrich, 1.61 g, 10 mmol) was treated with 4-(4-aminophenoxy)phenylamine (1.00 g, 5.0 mmol) according to the procedure of Example 33A. The title product was purified by chromatography (SiO$_2$, CH$_2$Cl$_2$:MeOH:NH$_3$.H$_2$O, 80:20:4, R$_f$, 0.10) as an oil (0.26 g, yield, 12%). $^1$H NMR (MeOH-d$_4$, 300 MHz) δ 1.34–1.55 (m, 2H), 1.59–1.84 (m, 4H), 1.84–2.09 (m, 4H), 2.44–2.64 (m, 2H), 2.68–3.11 (m, 8H), 3.19–3.39 (m, 2H), 3.42–3.64 (m, 2H), 6.55–6.66 (m, 4H), 6.67–6.86 (m, 4H) ppm. MS (DCl/NH$_3$) m/z 419 (M+H)$^+$.

Example 34B 4,4'-di(1-aza-bicyclo[2.2.2]oct-3-yl-amino)-diphenyl thioether tetra(hydrochloride)

The product of Example 34A (270 mg, 0.63 mmol) was treated with HCl (Aldrich, 4 M in dioxane, 1 mL, 4 mmol) in EtOAc (10 mL) at ambient temperature for 10 hours to give the title compound as solid (260 mg, yield, 75%). $^1$H NMR (MeOH-d$_4$, 300 MHz) δ 1.82–2.18 (m, 6H) 2.21–2.48 (m, 4H) 3.17–3.59 (m, 10H) 3.75–3.86 (m, 2H) 4.01–4.19 (m, 2H) 6.87–6.99 (m, 4H) 6.99–7.10 (m, 4H) ppm. MS (DCl/NH$_3$) m/z 419 (M+H)$^+$. Anal. calculated for C$_{26}$H$_{34}$N$_4$O.4.0HCl.4.0 H$_2$O: C, 49.06; H, 7.28; N, 13.38. Found: C, 48.80; H, 6.95; N, 8.59.

Example 35

N-1-azabicyclo[2.2.2]oct-3-yl-N'-phenylbenzene-1,4-diamine hydrochloride

Example 35A

N-(4-iodophenyl)quinuclidin-3-amine

3-Quinuclidinone hydrochloride (Aldrich, 3.22 g, 20 mmol) was treated with 4-iodo-aniline (2.19 g, 10 mmol) according to the procedure of Example 30A. The title product was purified by chromatography (SiO$_2$, CH$_2$Cl$_2$:MeOH:NH$_3$.H$_2$O, 90:10:2, R$_f$, 0.10) as oil (3.24 g, yield, 98%). $^1$H NMR (MeOH-d$_4$, 300 MHz) δ 1.70–1.81 (m, 1H), 1.93–2.04 (m, 2H), 2.08–2.24 (m, 2H), 2.89 (ddd, J=12.9, 5.1, 2.7 Hz, 1H), 3.12–3.28 (m, 4H), 3.64 (ddd, J=12.9, 9.5, 2.4 Hz, 1H), 3.79–3.85 (m, 1H), 6.46 (dt, J=9.0, 2.7 Hz, 2H), 7.39 (dt, J=9.1, 2.7 Hz, 2H) ppm. MS (DCl/NH$_3$) m/z 329 (M+H)$^+$.

Example 35B

N-(4-iodophenyl)quinuclidin-3-amine hydrochloride

The product of Example 35A (100 mg, 0.30 mmol) in ethyl acetate (5 mL) was treated with 4M HCl in 1,4-dioxane (0.5 mL). The title compound was obtained as solid (90 mg, yield, 75%). $^1$H NMR (MeOH-d$_4$, 300 MHz) δ 1.80–1.92 (m, 1H), 2.00–2.10 (m, 2H), 2.18–2.32 (m, 2H), 3.03 (ddd, J=12.9, 5.1, 2.7 Hz, 1H), 3.28–3.41 (m, 4H), 3.78 (ddd, J=12.9, 9.5, 2.4 Hz, 1H), 3.90–3.96 (m, 1H), 6.49 (dt, J=9.0, 2.7 Hz, 2H), 7.42 (dt, J=9.1, 2.7 Hz, 2H) ppm. MS (DCl/NH$_3$) m/z 329 (M+H)$^+$. Anal. calculated for C$_{13}$H$_{17}$IN$_2$.2.0HCl: C, 38.93; H, 4.77; N, 6.98. Found: C, 39.07; H, 4.53; N, 6.80.

Example 35C

N-1-azabicyclo[2.2.2]oct-3-yl-N'-phenylbenzene-1,4-diamine

The product of Example 35A (200 mg, 0.61 mmol) was treated with aniline (Aldrich, 93 mg, 1 mmol) according to the procedure of Example 17A. The title product was purified by chromatography (SiO$_2$, CH$_2$Cl$_2$:MeOH:NH$_3$.H$_2$O, 90:10:2, R$_f$, 0.20) as an oil (120 mg, yield, 68%). $^1$H NMR (MeOH-d$_4$, 300 MHz) δ 1.45–1.57 (m, 1H), 1.72–1.84 (m, 2H), 1.93–2.06 (m, 2H), 2.63 (ddd, J=12.9, 5.1, 2.7 Hz, 1H), 2.82–2.99 (m, 4H), 3.30–3.40 (m, 1H), 3.56–3.64 (m, 1H), 6.56–7.13 (m, 9H) ppm. MS (DCl/NH$_3$) m/z 294 (M+H)$^+$.

Example 35D

N-1-azabicyclo[2.2.2]oct-3-yl-N'-phenylbenzene-1,4-diamine hydrochloride

The product of Example 35C (120 mg, 0.40 mmol) in ethyl acetate (5 mL) was treated with 4M HCl in 1,4-dioxane (0.5 mL). The title compound was obtained as a solid (100 mg, yield, 69%). $^1$H NMR (MeOH-d$_4$, 300 MHz) δ 1.86–2.11 (m, 3H), 2.25–2.41 (m, 2H), 3.16 (ddd, J=12.9, 5.1, 2.5 Hz, 1H), 3.27–3.47 (m, 4H), 3.80 (ddd, J=12.9, 9.5, 2.4 Hz, 1H), 4.00–4.07 (m, 1H), 6.83–6.91 (m, 4H), 7.13–7.33 (m, 5H) ppm. MS (DCl/NH$_3$) m/z 294 (M+H)$^+$. Anal. calculated for C$_{19}$H$_{23}$N$_3$.2.4HCl .1.0H$_2$O: 57.20; H, 6.92; N, 10.53. Found: C, 57.25; H, 7.00; N, 10.53.

Example 36

3-[(4-phenoxyphenyl)thio]quinuclidine hydrochloride

Example 36A

3-[(4-bromophenyl)thio]quinuclidine

4-Bromobenzenethiol (Aldrich, 2.54 g, 24 mmol) in DMF (anhydrous, Aldrich, 40 mL) was treated with NaH (Aldrich, 95%,1.27 g, 48 mmol) at ambient temperature. After stirring for 20 minutes, the mixture was treated with 3-chloroqunuclidine hydrochloride (Aldrich, 3.64 g, 20 mmol) and stiired under N$_2$ at 100° C. for 18 hours. The mixture was cooled down to room temperature, treated with water (300 mL), and extracted with ethyl acetate (3×100 mL). The extracts were combined and washed with brine (2×30 mL). The organic phase was concentrated giving the title product as a brown oil (3.40 g, yield, 57%). $^1$H NMR (MeOH-d$_4$, 300 MHz) δ 1.48–1.60 (m, 1H), 1.64–1.92 (m, 2H), 2.05–2.19 (m, 2H), 2.65 (ddd, J=13.9, 5.7, 1.7 Hz, 1H), 2.81–2.97 (m, 4H), 3.39 (ddd, J=13.9, 9.8, 2.4 Hz, 1H), 3.37–3.63 (m, 1H), 7.30 (dt, J=8.5, 2.7 Hz, 2H), 7.45 (dt, J=8.4, 2.7 Hz, 2H) ppm. MS (DCl/NH$_3$) m/z 298 (M+H)$^+$, 300 (M+H)$^+$.

Example 36B

3-[(4-phenoxyphenyl)thio]quinuclidine

The product of Example 36A (300 mg, 1.0 mmol) was treated with phenol (Aldrich, 188 mg, 2 mmol) according to the procedure of Example 2A. The title product was purified by chromatography (SiO$_2$, CH$_2$Cl$_2$:MeOH:NH$_3$.H$_2$O, 90:10:2, R$_f$ 0.20) as an oil (220 mg, yield, 71%). $^1$H NMR (MeOH-d$_4$, 300 MHz) δ 1.45–1.66 (m, 2H), 1.77–1.98 (m, 2H), 2.13–2.24 (m, 1H), 2.62 (ddd, J=13.6, 5.4, 2.0 Hz, 1H), 2.76–2.92 (m, 4H), 3.29–3.40 (m, 1H), 3.44–3.54 (m, 1H), 6.92 (dt, J=9.0, 2.7 Hz, 2H), 6.97–7.01 (m, 2H), 7.00–7.14 (m, 1H), 7.32–7.44 (m, 4H) ppm. MS (DCI/NH$_3$) m/z 312 (M+H)$^+$.

Example 36C

3-[(4-phenoxyphenyl)thio]quinuclidine hydrochloride

The product of Example 36B (220 mg, 0.71 mmol) in ethyl acetate (5 mL) was treated with 4M HCl in 1,4-dioxane (0.5 mL). The title compound was obtained as a solid (180 mg, yield, 73%). $^1$H NMR (MeOH-d$_4$, 300 MHz) δ 1.84–2.02 (m, 2H), 2.05–2.20 (m, 2H), 2.37–2.52 (m, 1H), 3.14 (ddd, J=17.6, 10.5 2.4 Hz, 1H), 3.24–3.45 (m, 4H), 3.70–3.79 (m, 2H), 6.92 (dt, J=8.9, 3.0 Hz, 2H), 6.97–7.08 (m, 2H), 7.13–7.19 (m, 1H), 7.30–7.42 (m, 2H), 7.50 (dt, J=9.0, 3.0 Hz, 2H) ppm. MS (DCI/NH$_3$) m/z 312 (M+H)$^+$. Anal. calculated for C$_{19}$H$_{21}$NOS.1.0HCl.0.9H$_2$O: C, 62.67; H, 6.59; N, 3.85 Found: C, 62.31; H, 6.31; N, 4.23.

Example 37

N-[4-(1-azabicyclo[2.2.2]oct-3-ylthio)phenyl]-N-phenylamine dihydrochloride

Example 37A

N-[4-(1-azabicyclo[2.2.2]oct-3-ylthio)phenyl]-N-phenylamine

The product of Example 36A (300 mg, 1.0 mmol), as described herein, was treated with aniline (Aldrich, 186 mg, 2 mmol) according to the procedure of Example 17A, as described herein. The title product was purified by chromatography (SiO$_2$, CH$_2$Cl$_2$:MeOH:NH$_3$.H$_2$O, 90:10:2, R$_f$ 0.10) as an oil (210 mg, yield, 68%). $^1$H NMR (MeOH-d$_4$, 300 MHz) δ 1.42–1.64 (m, 2H), 1.74–1.85 (m, 2H), 2.15–2.27 (m, 1H), 2.62 (ddd, J=13.9, 4.7, 1.7 Hz, 1H), 2.77–2.95 (m, 4H), 3.21–3.40 (m, 2H), 6.87 (tt, J=7.4, 1.0 Hz, 1H), 7.01 (dt, J=8.8, 1.7 Hz, 2H), 7.05–7.10 (m, 2H), 7.19–7.25 (m, 2H), 7.30 (dt, J=8.8, 2.0 Hz, 2H) ppm. MS (DCI/NH$_3$) m/z 311 (M+H)$^+$.

Example 37B

N-[4-(1-azabicyclo[2.2.2]oct-3-ylthio)phenyl]-N-phenylamine Dihydrochloride

The product of Example 37A (210 mg, 0.68 mmol) in ethyl acetate (5 mL) was treated with 4M HCl in 1,4-dioxane (0.5 mL). The title compound was obtained as a solid (150 mg, yield, 58%). $^1$H NMR (MeOH-d$_4$, 300 MHz) δ 1.83–1.99 (m, 2H), 2.03–2.17 (m, 2H), 2.43–2.54 (m, 1H), 3.12 (ddd, J=12.5, 5.4 2.4 Hz, 1H), 3.26–3.46 (m, 4H), 3.58–3.75 (m, 2H), 6.91 (tt, J=7.4, 1.0 Hz, 1H), 7.04 (dt, J=8.8, 2.0 Hz, 2H), 7.09–7.12 (m, 2H), 7.22–7.25 (m, 2H), 7.38 (dt, J=8.8, 2.0 Hz, 2H) ppm. MS (DCI/NH$_3$) m/z 311 (M+H)$^+$. Anal. calculated for C$_{19}$H$_{22}$N$_2$S.2.0HCl.1.5H$_2$O: C, 55.47; H, 6.86; N, 6.81. Found: C, 55.72; H, 6.67; N, 6.26.

Example 38

3-[4-(4-iodo-phenoxy)-phenoxy]-1-aza-bicyclo[2.2.2]octane Hydrochloride

Example 38A

3-[4-(4-iodo-phenoxy)-phenoxy]-1-aza-bicyclo[2.2.2]octane

3-Hydroxy quinuclidine (Aldrich, 1.27 g, 10.0 mmol) was treated with 4,4'-diiodo-diphenyl ether (Aldrich, 4.22 g, 10 mmol), CuI (Strem Chemicals, 190 mg, 1.0 mmol), 1,10-phenanthroline (Aldrich, 360 mg, 2.0 mmol) and Cs$_2$CO$_3$ (6.60 g, 20.0 mmol) in toluene (anhydrous, Aldrich, 20 mL) and heated at 110° C. for two days according to the procedure of Example 2A. The title compound was purified by chromatography (SiO$_2$, CH$_2$Cl$_2$:MeOH:NH$_3$ H$_2$O, 90:10:1, R$_f$ 0.20) as solid (570 mg, yield, 13%). $^1$H NMR (MeOH-d$_4$, 300 MHz) δ 1.77–2.20 (m, 3H), 2.23–2.39 (m, 1 H), 2.42–2.57 (m, 1H), 3.31–3.49 (m, 6 H,) 3.80 (m, 1H), 6.73 (d, J=6.8 Hz, 2H), 6.90–7.11 (m, 4H), 7.62 (d, J=6.8 Hz, 2H) ppm. MS (DCI/NH$_3$) m/z 422 (M+H)$^+$.

Example 38B

3-[4-(4-iodo-phenoxy)-phenoxy]-1-aza-bicyclo[2.2.2]octane hydrochloride

The product of 38A (50.0 mg, 0.12 mmol) in ethyl acetate (5 mL) was treated with 4M HCl in 1,4-dioxane (0.25 mL, 1.0 mmol) to provide the title compound as a solid (52.0 mg, yield, 95%). $^1$H NMR (MeOH-d$_4$, 300 MHz) δ 1.77–2.23 (m, 3H), 2.24–2.38 (m, 1H), 2.42–2.64 (m, 1H), 3.20–3.49 (m, 6H), 3.65–3.91 (m, 1H), 6.72 (d, J=6.8 Hz, 1H), 7.00 (s, 4H), 7.62 (d, J=6.8 Hz, 2H) ppm. MS (DCI/NH$_3$) m/z 422(M+H)$^+$. Anal. Calculated for C$_{19}$H$_{20}$INO$_2$.1.00HCl.0.25H$_2$O: C, 49.37; H, 4.69; N, 3.03. Found: C, 49.25; H, 4.30; N, 2.96.

Example 39

{4-[4-(1-aza-bicyclo[2.2.2]oct-3-yloxy)-phenoxy]-phenyl}-hydrazine bis(hydrochloride)

Example 39A

N-{4-[4-(1-aza-bicyclo[2.2.2]oct-3-yloxy)-phenoxy]-phenyl}-hydrazinecarboxylic acid tert-butyl ester The product of Example 38A (420 mg, 1.0 mmol) was coupled with tert-butyl carbazate (Aldrich, 158 mg, 1.2 mmol) under the catalysis of CuI (Strem Chemicals, 9.5 mg, 0.05 mmol) with Cs$_2$CO$_3$ (Strem Chemicals, 489 mg, 1.4 mmol) in DMF (anhydrous, Aldrich, 5 mL) at 80° C. overnight. The mixture was diluted with EtOAc (50 mL) and washed with water (2×10 mL). The organic solution was concentrated and the title compound was purified by chromatography (SiO$_2$, CH$_2$Cl$_2$:MeOH:NH$_3$.H$_2$O, 90:10:2, R$_f$ 0.20) as an oil (190 mg, yield, 45%). ¹H NMR (MeOH-d₄, 300 MHz) δ 1.46 (s, 9H), 1.76–2.16 (m, 3H), 2.20–2.39 (m, 1H), 2.41–2.54 (m, 1H), 3.16–3.47 (m, 5H), 3.66–3.86 (m, 1H), 4.70–4.84 (m, 1H), 6.77–6.93 (m, 2H), 6.94–7.04 (m, 4H), 7.25–7.48 (m, 2H) ppm. MS (DCl/NH₃) m/z 426 (M+H)⁺.

Example 39B

{4-[4-(1-aza-bicyclo[2.2.2]oct-3-yloxy)-phenoxy]-phenyl}-hydrazine bis(hydrochloride)

The product of Example 39A (80 mg, 0.19 mmol) was treated with HCl (Aldrich, 4 M in dioxane, 0.5 mL, 2.0 mmol) in EtOAc (5 mL) at room temperature for 10 h to give the title compound as yellow solid (60 mg, yield, 79%). ¹H NMR (MeOH-d₄, 300 MHz) δ 1.76–2.20 (m, 3H), 2.21–2.40 (m, 1H), 2.40–2.59 (m, 1H), 3.20–3.48 (m, 6H), 3.70–3.85 (m, 1H), 6.83–7.19 (m, 8H) ppm. MS (DCl/NH₃) m/z 426(M+H)⁺. Anal. Calculated for C₁₉H₂₃N₃O₂.2.40HCl.0.20H₂O.0.50EtOAc: C, 54.76; H, 6.52; N, 9.12. Found: C, 54.50; H, 6.13; N, 8.84.

Example 40

3-[4-(2-methyl-3-phenyl-1H-indol-5-yloxy)-phenoxy]-1-aza-bicyclo[2.2.2]octane hydrochloride Example 40A 3-[4-(2-methyl-3-phenyl-1H-indol-5-yloxy)-phenoxy]-1-aza-bicyclo[2.2.2]octane The product of Example 39A (105 mg, 0.25 mmol) was treated with 1-phenyl-propan-1-one (Aldrich, 67 mg, 0.5 mmol) and HCl (Aldrich, 4 M in dioxane, 0.5 mL, 2 mmol) in EtOH (3.0 mL) at 80° C. for 10 h. The mixture was concentrated and the title compound was was purified by preparative HPLC (Xterra™, column, Xterra RP-18 5 μm, 30×100 mm. Eluting Solvent, MeCN/H₂O (NH₄HCO₃, 0.1 M, pH=10) (v. 40/60 to 70/30 over 20 min.) Flow rate, 75 mL/min., uv, 250 nm) as solid (60 mg, yield, 57%). ¹H NMR (300 MHz, CD₃OD) δ 1.45–1.80 (m, 4H), 2.09–2.19 (m, 1H), 2.37 (s, 3H), 2.62–2.97 (m, 4H), 3.19–3.44 (m, 1H), 4.34–4.53 (m, 1H), 6.81 (dd, J=8.6, 2.2 Hz, 1H), 6.85–7.04 (m, 4H), 7.09 (d, J=2.4 Hz, 1H), 7.27–7.38 (m, 2H), 7.46 (t, J=7.6 Hz, 2H), 7.63 (d, J=7.1 Hz, 2H) ppm; MS (DCl/NH₃) m/z 425 (M+H)⁺.

Example 40B

3-[4-(2-methyl-3-phenyl-1H-indol-5-yloxy)-phenoxy]-1-aza-bicyclo[2.2.2]octane hydrochloride The product of Example 40A (60 mg, 0.14 mmol) was treated with HCl (Aldrich, 4 M in dioxane, 0.25 mL, 1.0 mmol) in EtOAc (5 mL) at ambient temperature for 1 hour to give the title compound as solid (25.0 mg, yield, 39%). ¹H NMR (MeOH-d₄, 300 MHz) δ 1.78–2.04 (m, 2H), 2.03–2.21 (m, 1H), 2.28–2.37 (m, 1H), 2.37 (s, 3H), 2.45–2.56 (m, 1H), 3.33–3.47 (m, 5H), 3.68–3.86 (m, 1H), 4.73–4.83 (m, 1H), 6.81 (dd, J=8.8, 2.4 Hz, 1H), 6.88–6.98 (m, 4H), 7.09 J=2.4 Hz, 1 H,) 7.25–7.38 (m, 2H), 7.42–7.52 (m, 2H), 7.59–7.69 (m, 2H)ppm. MS (DCl/NH₃) m/z 425 (M+H)⁺. Anal. Calculated for C₁₈H₂₈N₂O₂.1.40HCl.0.62H₂O: C, 69.09; H, 6.34; N, 5.76. Found: C, 69.43; H, 5.97; N, 5.43.

Example 41

3-[6-(4-iodo-phenoxy)-pyridazin-3-yloxy]-1-aza-bicyclo[2.2.2]octane tri(hydrochloride)

Example 41A

3-[6-(4-iodo-phenoxy)-pyridazin-3-yloxy]-1-aza-bicyclo[2.2.2]octane

The product of Example 27C (870 mg, 3.00 mmol) was treated trifluroacetic acid (0.46 mL, 6.0 mmol) in MeCN (Aldrich, 10.0 mL) at ambient temperature for 10 min. N-Iodosuccinimide (Aldrich, 0.742 g, 3.3 mmol) was then added and the mixture was stirred at 80° C. for 6 h. The mixture was concentrated. The title compound was purified by chromatography (SiO₂, CH₂Cl₂:MeOH:NH₃.H₂O, 90:10:1, R_f, 0.35) as solid (270 mg, yield, 21%). ¹H NMR (300 MHz, CD₃OD) δ 1.81–2.17 (m, 3H), 2.23–2.40 (m, 1H), 2.47–2.64 (m, 1H), 3.17–3.45 (m, 5H), 3.81 (dd, J=14.1, 8.3 Hz, 1 H), 5.19–5.49 (m, 1H), 7.00(dt, J=8.8, 2.1 Hz, 2H), 7.33 (d, J=9.5 Hz, 1H), 7.42 (d, J=9.5 Hz, 1H), 7.76 (dt, J=8.8, 2.1 Hz, 2H) ppm; MS (DCl/NH₃) m/z 424 (M+H)⁺.

Example 41B

3-[6-(4-iodo-phenoxy)-pyridazin-3-yloxy]-1-aza-bicyclo[2.2.2]octane tri(hydrochloride)

The product of Example 41A (20 mg, 0.05 mmol) was treated with HCl (Aldrich, 4 M in dioxane, 0.25 mL, 1.0 mmol) in EtOAc (2 mL) at ambient temperature for 1 hour to give the title compound as solid (20.0 mg, yield, 80%). ¹H NMR (MeOH-d₄, 300 MHz) δ 1.87–2.20 (m, 3H), 2.27–2.47 (m, 1H), 2.52–2.65 (m, 1H), 3.31–3.48 (m, 5H), 3.78–3.97 (m, 1H), 5.25–5.50 (m, 1H), 6.99 (dt, J=9.1, 2.3 Hz, 2H), 7.34 (d, J=9.5 Hz, 1H), 7.43 (d, J=9.5 Hz, 1H), 7.77 (dt, J=9.1, 2.0 Hz, 2H) ppm. MS (DCl/NH₃) m/z 424(M+H)⁺. Anal. Calculated for C₁₇H₁₈IN₃O₂.3.55HCl.1.80H₂O: C, 34.90; H, 4.33; N, 7.18. Found: C, 34.53; H 3.95; N, 6.83.

Example 42

2-(1-aza-bicyclo[2.2.2]oct-3-yloxy)-8-iodo-6H,12H-5,11-methano-dibenzo[b,f][1,5]diazocine fumarate Example 42A 2,8-diiodo-6H,12H-5,11-methano-dibenzo[b,f][1,5] diazocine The mixture of 4-iodo-phenylamine (Aldrich, 6.57 g, 30 mmol) and paraformaldehyde (Aldrich, 1.80 g, 60 mmol) in trifluoroacetic acid (Aldrich, 60 mL) was stirred at ambient temperature for 15 hour. It was then concentrated, dissolved in water (10 mL) and neutralized with NH₃.H₂O till pH=9. The mixture was extracted with EtOAc (3×50 mL). The extracts were combined and concentrated. The title compound was purified by chromatography (SiO₂, hexane: EtOAc, 50:50, R_f, 0.40) as solid (2.70 g, yield, 38%).¹H NMR (300 MHz, CDCl₃) δ 4.09 (d, J=17.0 Hz, 2H), 4.26 (s, 2H), 4.63 (d, J=16.6 Hz, 2H), 6.89 (d, J=8.5 Hz, 2H), 7.16–7.31 (m, 2H), 7.47 (dd, J=8.5, 2.0 Hz, 2H) ppm. MS (DCl/NH₃) 475 (M+H)⁺.

Example 42B 2-(1-aza-bicyclo[2.2.2]oct-3-yloxy)-8-iodo-6H,12H-5,11-methano-dibenzo[b,f][1, The product of example 42A (474 mg, 1.0 mmol) was coupled with the 3-hydroxy quinuclidine (Aldrich, 254 mg, 2.0 mmol) under the catalysis of CuI (Strem Chemicals, 19.0 mg, 0.1 mmol) and 1,10-phenanthroline (Aldrich, 36 mg, 0.2 mmol) with $Cs_2CO_3$ (Aldrich, 652 mg, 2.0 mmol) in toluene (5 mL) at 110° C. for 40 hours according to the procedure of Example 14A. The title compound was purified by chromatography ($SiO_2$, $CH_2Cl_2$:MeOH (with v. 2% $NH_3.H_2O$, 90:10, $R_f$, 0.30) as solid (120 mg, yield, 25%). $^1$H NMR (300 MHz, $CDCl_3$) δ 1.48–1.65 (m, 2H), 1.66–2.08 (m, 3H), 2.08–2.18 (m, 1H), 2.68–3.10 (m, 5H), 3.12–3.37 (m, 1H), 3.95–4.18 (dd, J=16.9, 6.4 Hz, 2H), 4.18–4.34 (m, 3H), 4.61 (dd, J=17.3, 11.3 Hz, 2H), 6.36 (d, J=2.7 Hz, 1H), 6.69 (dd, J=8.8, 2.7 Hz, 1H), 6.88 (d, J=8.5 Hz, 1H), 7.02 (d, J=8.8 Hz, 1H), 7.24 (d, J=2.0 Hz, 1H), 7.45 (dd, J=8.5, 1.7 Hz, 1H) ppm. MS ($DCl/NH_3$) 474 $(M+H)^+$.

Example 42C 2-(1-aza-bicyclo[2.2.2]oct-3-yloxy)-8-iodo-6H,12H-5,11-methano-dibenzo[b,f][1,5]diazocine fumarate The product of Example 42B (30 mg, 0.06 mmol) was treated with fumaric acid (11.6 mg, 0.1 mmol) in EtOH/MeOH (v. 10/1, 2 mL) at room temperature for 10 h to give the title compound (28 mg, yield, 75%). $^1$H NMR (MeOH-$d_4$, 300 MHz) δ 1.72–2.12 (m, 3H), 2.13–2.33 (m, 1H), 2.33–2.49 (m, 1H), 3.23–3.37 (m, 5H), 3.68 (dd, J=13.7, 8.3 Hz, 1H), 4.11 (t, J=19.0 Hz, 2H), 4.29 (s, 2H), 4.62 (dd, J=16.8, 12.0 Hz, 2H), 4.69–4.80 (m, 1H), 6.57 (dd, J=5.6, 2.9 Hz, 1H), 6.69 (s, 2H), 16.8, (dt, J=4.4, 2.7Hz, 1H), 6.91 (d, J=8.5 Hz, 1H), 7.09 (d, J=8.8 Hz, 1H), 7.29 (d, J=2.0 Hz, 1H), 7.47 (dd, J=8.5, 2.0 Hz, 1H) ppm. MS ($DCl/NH_3$) m/z 474$(M+H)^+$. Anal. Calculated for $C_{22}H_{24}IN_3O.1.30C_4H_4O_4.0.70H_2O$: C, 51.30; H, 4.84; N, Found: C, 51.49; H, 4.84; N, 6.22.

Example 43

2-(1-aza-bicyclo[2.2.2]oct-3-yloxy)-6H,12H-5,11-methano-dibenzo[b,f][1,5]diazoc tri(hydrochloride)

Example 43A 2-(1-aza-bicyclo[2.2.2]oct-3-yloxy)-6H,12H-5,11-methano-dibenzo[b,f][1,5]diazoc The product of example 42B (90 mg, 0.19 mmol) was hydrogenated under the catalysis of Pd/C (Aldrich, 10 wt. %, 20 mg) in EtOH (10 mL) under H2 at ambient temperature for 2 h. The catalyst was then filtered off. The ethanol solution was concentrated, treated with 1N NaOH (1 mL) and extracted with $CHCl_3$/iPrOH (v. 10:1, 3×10 mL). The extracts were combined and concentrated to give the title compound as yellow solid (60 mg, yield, 91%). $^1$H NMR (300 MHz, $CDCl_3$) δ 1.52–1.85 (m, 3H), 1.91–2.03 (m, 1H), 2.02–2.15 (m, 1H), 2.58–2.97 (m, 5H), 3.14–3.28 (m, 1H), 4.13 (t, J=16.3 Hz, 2H), 4.31 (s, 2H), 4.34–4.44 (m, 1H), 4.64 (d, J=16.6 Hz, 2H), 6.49 (s, 1H), 6.75 (dd, J=8.6, 2.9 Hz, 1H), 6.89–7.20 (m, 5H) ppm. MS ($DCl/NH_3$) 348 $(M+H)^+$.

Example 43B 2-(1-aza-bicyclo[2.2.2]oct-3-yloxy)-6H,12H-5,11-methano-dibenzo[b,f][1,5]diazoc tri(hydrochloride)

The product of Example 43A (60 mg, 0.17 mmol) was treated with HCl (Aldrich, 4 M in dioxane, 0.25 mL, 1.0 mmol) in EtOAc (5 mL) at room temperature for 10 h to give the title compound (70.0 mg, yield, 90%). $^1$H NMR (MeOH-$d_4$, 300 MHz) δ 1.72–2.28 (m, 4H), 2.36–2.57 (m, 1H), 3.19–3.43 (m, 6H), 3.79 (dd, J=14.2, 8.5 Hz, 1H), 4.50 (dd, J=15.9, 8.1 Hz, 2H), 4.88–5.15 (m, 4H), 6.86 (t, J=2.5 Hz, 1H), 7.07 (dt, J=8.8, 2.4 Hz, 1H), 7.18 (d, J=7.5 Hz, 1H), 7.22–7.32 (m, 1H), 7.36–7.45 (m, 2H), 7.48 (d, J=8.8 Hz, 1H) ppm. MS ($DCl/NH_3$) m/z 348 $(M+H)^+$. Anal. Calculated for $C_{22}H_{25}N_3O.3.35C_4H_4O_4.2.05H_2O$: C, 2.17; H, 6.46; N, 8.30. Found: C, 51.78; H, 6.06; N, 8.02.

Example 44

Determination of Biological Activity

To determine the effectiveness of representative compounds of this invention as α7 nAChRs, the compounds of the invention were evaluated according to the [3H]-methyllycaconitine (MLA) binding assay and considering the [3H]-cytisine binding assay, which were performed as described below.

[3H]-Cytisine Binding

Binding conditions were modified from the procedures described in Pabreza L A, Dhawan, S, Kellar K J, [$^3$H]-Cytisine Binding to Nicotinic Cholinergic Receptors in Brain, Mol. Pharm. 39: 9–12, 1991. Membrane enriched fractions from rat brain minus cerebellum (ABS Inc., Wilmington, Del.) were slowly thawed at 4° C. washed and resuspended in 30 volumes of BSS-Tris buffer (120 mM NaCl/5 mM KCl/2 mM $CaCl_2$/2 mM $MgCl_2$/50 mM Tris-Cl, pH 7.4, 4° C.). Samples containing 100–200 µg of protein and 0.75 nM [3H]-cytisine (30 $C_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM $CaCl_2$/2 mM $MgCl_2$). Packard MicroScint-20® scintillation cocktail (40 µL) was added to each well and radioactivity determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/1+[Ligand]/K_D]$.

[3H]-Methyllycaconitine (MLA) Binding

Binding conditions were similar to those for [3H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM $CaCl_2$, 2 mM $MgCl_2$, and 50 mM Tris-Cl, pH 7.4, 22° C.). Samples containing 100–200 µg of protein, 5 nM [3H]-MLA (25 $C_i$/mmol; Perkin Elmer/NEN Life Science Products, Boston, Mass.) and 0.1% bovine serum albumin (BSA, Millipore, Bedford, Mass.) were incubated in a final volume of 500 µL for 60 minutes at 22° C. Seven log-dilution concentrations of each compound were tested in duplicate. Non-specific binding was determined in the presence of 10 μM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 μL) was added to each well and radioactivity was determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/1+[Ligand]/K_D$.

Compounds of the invention had Ki values of from about 1 nanomolar to about 10 micromolar when tested by the MLA assay, many having a $K_i$ of less than 1 micromolar. [3H]-Cytisine binding values of compounds of the invention ranged from about 50 nanomolar to at least 100 micromolar. The determination of preferred compounds typically considered the $K_i$ value as measured by MLA assay in view of the $K_i$ value as measured by [3H]-cytisine binding, such that in the formula $D=K_{i\ 3H\text{-}cytisine}/K_{i\ MLA}$, D is about 50. Preferred compounds typically exhibited greater potency at α7 receptors compared to α4β2 receptors.

Compounds of the invention are α7 nAChRs ligands that modulate function of α7 nAChRs by altering the activity of the receptor. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula (I):

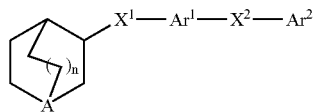
(I)

or a pharmaceutically acceptable salt, ester, or amide, thereof, wherein:
A is N or $N^+$—$O^-$;
n is 0, 1, or 2;
$X^1$ is selected from the group consisting of O, S, and —N($R^1$)—
$X^2$ is selected from the group consisting of O, S, —N($R^1$)—, —N($Ar^2$)—, and —N($R^2$)C(O)—;
$Ar^1$ is a group of the formula:

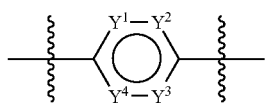
(a)

$Ar^2$ is cycloalkyl, or $Ar^2$ is a group of the formula:

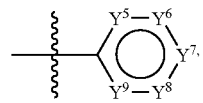
(b)

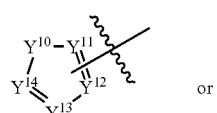
(c)

or

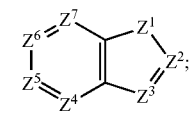
(d)

$Y^1$, $Y^2$, $Y^3$, and $Y^4$ are each independently selected from the group consisting of N and —$CR^3$;
$Y^5$, $Y^6$, $Y^7$, $Y^8$, and $Y^9$ are each independently selected from the group consisting of N and —C($R^6$);
$Y^{10}$ is selected from the group consisting of —N($R^9$), O and S;
$Y^{11}$, $Y^{12}$, $Y^{13}$, and $Y^{14}$ are each independently selected from the group consisting of N, C and —C($R^6$); provided that one of $Y^{11}$, $Y^{12}$, $Y^{13}$, and $Y^{14}$ is C and formula (c) is attached to $X^2$ or the nitrogen atom of —N($Ar^2$)— through one of $Y^{11}$, $Y^{12}$, $Y^{13}$, and $Y^{14}$ that is represented by C;
$Z^1$ is independently selected from O, S, —N($R^9$), —C($R^{10}$) and —C($R^{10}$)($R^{10a}$);
$Z^2$ and $Z^3$ are each independently selected from the group consisting of N, C and —Cis —C($R^{10}$), provided that zero or one of $Z^2$ and $Z^3$ is C; and provided that when $Z^1$ is —C($R^{10}$), then $Z^2$ and $Z^3$ are other than C; and further provided that when one of $Z^2$ or $Z^3$ is C, then $Z^1$ is other than —C($R^{10}$);
$Z^4$, $Z^5$, $Z^6$, and $Z^7$ are independently selected from the group consisting of C and —C($R^{11}$); provided that zero or one of $Z^4$, $Z^5$, $Z^6$, and $Z^7$ is C; wherein
when one of $Z^4$, $Z^5$, $Z^6$, and $Z^7$ is C, then formula (d) is attached to $X^2$ or the nitrogen atom of —N($Ar^2$)— through one of $Z^4$, $Z^5$, $Z^6$, and $Z^7$ that is represented by C; $Z^1$ is other than —C($R^{10}$); and $Z^2$ and $Z^3$ are other than C; or
when $Z^1$ is —C($R^{10}$), then formula (d) is attached to $X^2$ or the nitrogen atom of —N($Ar^2$)— through the C atom of —C($R^{10}$); $Z^4$, $Z^5$, $Z^6$, and $Z^7$ are —C($R^{11}$); and $Z^2$ and $Z^3$ are other than C; or
when one of $Z^2$ or $Z^3$ is C, then formula (d) is attached to $X^2$ or the nitrogen atom of —N($Ar^2$)— through $Z^2$ or $Z^3$ represented by C; $Z^1$ is other than —C($R^{10}$); and $Z^4$, $Z^5$, $Z^6$, and $Z^7$ are —C($R^{11}$);
$R^1$ and $R^2$ at each occurrence are each independently selected from the group consisting of hydrogen and alkyl;
$R^3$ at each occurrence is independently selected from the group consisting of hydrogen, halo, alkyl, aryl, —$OR^4$, and —$NHR^5$;
$R^4$ and $R^5$ are each independently selected from the group consisting of hydrogen, alkyl, alkylcarbonyl, arylcarbonyl, alkylsulfonyl, and arylsulfonyl;
$R^6$ at each occurrence is independently selected from the group consisting of hydrogen, halo, haloalkyl, alkyl, aryl, alkylcarbonyl, —$OR^7$, and —$NHR^8$;

R⁷ and R⁸ are each independently selected from the group consisting of hydrogen, alkyl, 1-aza-bicyclo[2.2.2]oct-3-yl, amino, alkylcarbonyl, arylcarbonyl, alkylsulfonyl, and arylsulfonyl; and R⁹, R¹⁰, R¹⁰ᵃ, R¹¹, and R¹² at each occurrence are each independently selected from the group consisting of hydrogen, alkyl, aryl, alkylcarbonyl, and arylcarbonyl.

2. The compound of claim 1, wherein Ar¹ is selected from the group consisting of:

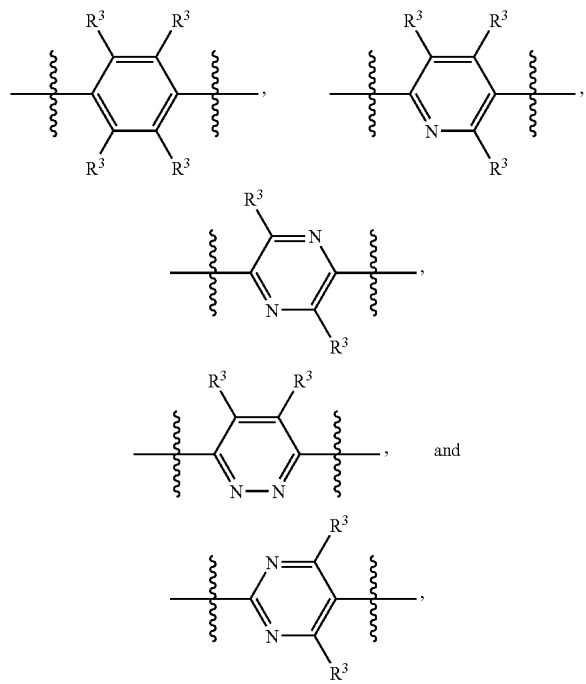

wherein R³ is as defined in claim 1.

3. The compound of claim 1, wherein Ar² is selected from the group consisting of cycloalkyl,

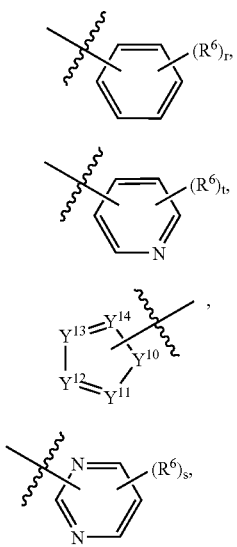

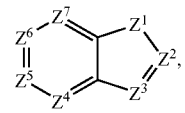

wherein r is 0, 1, 3, 4 or 5;

s is 0, 1, 2 or 3;

t is 0, 1, 2, 3 or 4;

Y¹⁰ is selected from the group consisting of —N(R⁹), O and S;

one of Y¹² and Y¹³ is N, C or —C(R⁶), and the other is C or —C(R⁶);

Y¹¹ and Y¹⁴ are each independently selected from the group consisting of C and —CR⁶; provided that one of Y¹¹ and Y¹⁴ or one of Y¹² and Y¹³ is C and formula (c) is attached to X² or the nitrogen atom of —N(Ar²)— through one of Y¹¹, Y¹², Y¹³, and Y¹⁴ that is represented by C; and Z¹, Z², Z³, Z⁴, Z⁵, Z⁶, Z⁷, R⁶, and R⁹ are as defined in claim 1.

4. The compound of claim 1, wherein Ar² is selected from the group consisting of cyclohexyl,

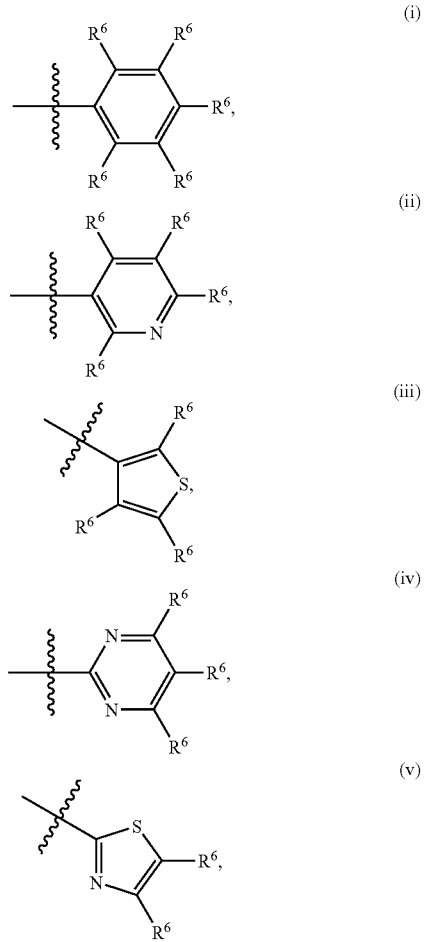

-continued (vi)

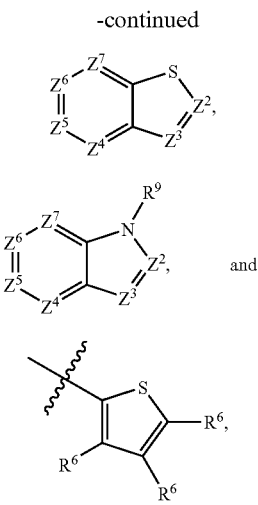

(vii)

(viii)

wherein:
$Z^2$ and $Z^3$ are independently N, C or —C($R^{12}$); provided that zero or one of $Z^2$ and $Z^3$ is C;

$Z^4$, $Z^5$, $Z^6$, and $Z^7$ are independently selected from the group consisting of C and —C($R^{11}$); provided that zero or one of $Z^4$, $Z^5$, $Z^6$, and $Z^7$ is C; wherein when one of $Z^4$, $Z^5$, $Z^6$, and $Z^7$ is C, then each of formulas (4-vi) and (4-vii) is attached to X2 or the nitrogen atom of N(Ar2)- through one of $Z^4$, $Z^5$, $Z^6$ and $Z^7$ that is represented by C, and $Z^2$ and $Z^3$ are each —C($R^{12}$); or when one of $Z^2$ or $Z^3$ is C, then each of formulas (4-vi) and (4-vii) is attached to $X^2$ or the nitrogen atom of —N(Ar²)— through $Z^2$ or $Z^3$ represented by C, and $Z^4$, $Z^5$, $Z^6$ and $Z^7$ are —C($R^{11}$);

$R^6$ is selected from the group consisting of hydrogen, fluoro, trifluoromethyl, hydroxy, 1-aza-bicyclo[2.2.2]oct-3-yloxy, 1-aza-bicyclo[2.2.2]oct-3-ylamino, isopropoxy, bromo, chloro, iodo, methyl, hydrazino, and amino;

$R^{12}$ is selected from the group consisting of hydrogen, methyl and phenyl; and $R^9$ and $R^{11}$ are as defined in claim 1.

5. The compound of claim 1, or a pharmaceutically acceptable salt, ester or amide, thereof, selected from the group consisting of:
3-(3-phenoxyphenoxy)quinuclidine;
3-(4-phenoxyphenoxy)quinuclidine;
(3R)-3-(4-phenoxyphenoxy)quinuclidine;
(3S)-3-(4-phenoxyphenoxy)quinuclidine;
3-{4-[4-(trifluoromethyl)phenoxy]phenoxy}quinuclidine;
3-[4-(4-fluorophenoxy)phenoxy]quinuclidine;
4-[4-(1-azabicyclo[2.2.2]oct-3-yloxy)phenoxy]phenol;
4-{4-[(3R)-1-azabicyclo[2.2.2]oct-3-yloxy]phenoxy}phenol;
4-{[4-(1-azabicyclo[2.2.2]oct-3-yloxy)phenyl]thio}phenol;
4-({4-[(3R)-1-azabicyclo[2.2.2]oct-3-yloxy]phenyl}thio)phenol;
3-{4-[(4-isopropoxyphenyl)thio]phenoxy}quinuclidine;
3-[4-(pyridin-3-yloxy)phenoxy]quinuclidine;
3-[4-(thien-3-yloxy)phenoxy]quinuclidine;
3-{4-[(5-bromopyrimidin-2-yl)oxy]phenoxy}quinuclidine;
N-[4-(1-azabicyclo[2.2.2]oct-3-yloxy)phenyl]-N-phenylamine;
N-{4-[(3R)-1-azabicyclo[2.2.2]oct-3-yloxy]phenyl}-N-phenylamine;
N-[4-(1-azabicyclo[2.2.2]oct-3-yloxy)phenyl]pyridin-3-amine;
N-[4-(1-azabicyclo[2.2.2]oct-3-yloxy)phenyl]benzamide;
N-[4-(1-azabicyclo[2.2.2]oct-3-yloxy)phenyl]-N-cyclohexylamine;
N-[4-(1-azabicyclo[2.2.2]oct-3-yloxy)phenyl]-N,N-dithien-3-ylamine;
N-[4-(1-azabicyclo[2.2.2]oct-3-yloxy)phenyl]-N-1,3-thiazol-2-yl-1,3-thiazol-2-amine;
N-[4-(1-azabicyclo[2.2.2]oct-3-yloxy)phenyl]-N,N-bis(1-benzothien-3-yl)amine;
1-(5-{[4-(1-azabicyclo[2.2.2]oct-3-yloxy)phenyl]amino}thien-2-yl)ethanone;
N-[4-(1-azabicyclo[2.2.2]oct-3-yloxy)phenyl]-N-(4-methylthien-3-yl)amine;
3-[(6-phenoxypyridazin-3-yl)oxy]quinuclidine;
3-[(5-phenoxypyridin-2-yl)oxy]quinuclidine;
3-[(5-phenoxypyrimidin-2-yl)oxy]quinuclidine;
N-(4-phenoxyphenyl)quinuclidin-3-amine;
N-[4-(4-chlorophenoxy)phenyl]quinuclidin-3-amine;
N-[4-(4-methylphenoxy)phenyl]quinuclidin-3-amine;
N-[4-(4-aminophenoxy)phenyl]quinuclidin-3-amine
N-1-azabicyclo[2.2.2]oct-3-yl-N'-phenylbenzene-1,4-diamine;
3-[(4-phenoxyphenyl)thio]quinuclidine;
N-[4-(1-azabicyclo[2.2.2]oct-3-ylthio)phenyl]-N-phenylamine;
4,4'-di(1-aza-bicyclo[2.2.2]oct-3-yloxy)-diphenyl ether;
4,4'-di[(3R)-1-aza-bicyclo[2.2.2]oct-3-yloxy]-diphenyl thioether;
4,4'-di(1-aza-bicyclo[2.2.2]oct-3-yl-amino)-diphenyl thioether;
3-[4-(4-iodo-phenoxy)-phenoxy]-1-aza-bicyclo[2.2.2]octane;
{4-[4-(1-aza-bicyclo[2.2.2]oct-3-yloxy)-phenoxy]-phenyl}-hydrazine;
3-[4-(2-methyl-3-phenyl-1H-indol-5-yloxy)-phenoxy]-1-aza-bicyclo[2.2.2]octane; and
3-[6-(4-iodo-phenoxy)-pyridazin-3-yloxy]-1-aza-bicyclo[2.2.2]octane.

6. A compound of the formula (II):

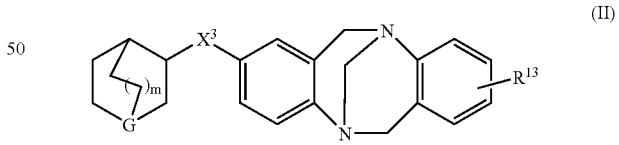

(II)

or a pharmaceutically acceptabel salt, ester, or amide, thereof, wherein:
G is N or $N^+$—$O^{31}$ ;
$X^3$ is —N($R^{14}$)—, O, or S;
m is 0, 1, or 2;
$R^{14}$ is hydrogen or alkyl; and
$R^{13}$ is hydrogen alkyl, or halogen.

7. The compund of claim 6, or a pharmaceutically acceptable salt, ester, or amide, thereof, selected from the group consisting of:
2-(1-aza-bicyclo[2.2.2]oct-3-yloxy)-8-iodo-6H, 12H-5,11-methano-dibanzo[b,f][1,5]diazocine; and 2-(1-aza-bicyclo[2.2.2]oct-3-yloxy)-6H, 12H-5,11-methano-dibenzo[b,f][1,5]diazocine.

8. A pharmaceutical composition comprising a therapeutically effective amount of a compound of claim 1 in combination with a pharmaceutically acceptable carrier.

9. A method of treating a condition or disorder selected from the group consisting of attention deficit disorder, attention deficit hyperactivity disorder (ADHD), Alzheimer's disease (AD), mild cognitive impairment, senile dementia, AIDS dementia, dementia associated with Lewy bodies, dementia associated with Down's syndrome, diminished CNS function associated with traumatic brain injury, comprising the step of administering a compound of claim 1.

10. The method according to claim 9, wherein the condition or disorder is a cognitive disorder.

11. The method according to claim 9, in combination with an atypical antipsychotic.

12. The method of treating schizophrenia, comprising the step of administering a compound of claim 1.

* * * * *